(12) United States Patent
Chan et al.

(10) Patent No.: US 7,700,601 B2
(45) Date of Patent: Apr. 20, 2010

(54) SUBSTITUTED INDAZOLES OF FORMULA 1.0 THAT ARE KINASE INHIBITORS

(75) Inventors: Tin-Yau Chan, Edison, NJ (US); Brian A. McKittrick, New Vernon, NJ (US); Haiyan Pu, Livingston, NJ (US); Liwu Hong, Edison, NJ (US); Andrew J. Prongay, Stewartsville, NJ (US); Li Xiao, Cranbury, NJ (US); Mark A. McCoy, Randolph, NJ (US)

(73) Assignee: Schering Corporation, Kenilworth, NJ (US)

( * ) Notice: Subject to any disclaimer, the term of this patent is extended or adjusted under 35 U.S.C. 154(b) by 28 days.

(21) Appl. No.: 11/729,020

(22) Filed: Mar. 28, 2007

(65) Prior Publication Data

US 2008/0021019 A1 Jan. 24, 2008

Related U.S. Application Data

(60) Provisional application No. 60/788,465, filed on Mar. 31, 2006.

(51) Int. Cl.
*A61K 31/4965* (2006.01)
(52) U.S. Cl. .................. 514/255.05; 544/359; 544/405; 548/361.1
(58) Field of Classification Search ............ 514/255.05; 544/359, 405; 548/361.1
See application file for complete search history.

(56) References Cited

U.S. PATENT DOCUMENTS

| 2003/0187026 A1 | 10/2003 | Li et al. |
| 2003/0199511 A1 | 10/2003 | Li et al. |

FOREIGN PATENT DOCUMENTS

| EP | 1 380 576 | 1/2004 |
| WO | WO 02/060492 | 8/2002 |
| WO | WO 03/045924 | 6/2003 |
| WO | WO 03/051366 | 6/2003 |
| WO | WO 2005/016862 | 2/2005 |
| WO | WO 2005/058876 | 6/2005 |
| WO | WO 2005/085227 | 9/2005 |
| WO | WO 2006/071548 | 7/2006 |
| WO | WO 2006/081230 | 8/2006 |
| WO | WO 2006/086705 | 8/2006 |
| WO | WO 2007/032936 | 3/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Patani, et al. Chem. Rev., 96, 1996, pp. 3147-3176.*
PCT International Search Report dated Oct. 23, 2007 for corresponding PCT Application No. PCT/US2007/007779.

* cited by examiner

*Primary Examiner*—James O Wilson
*Assistant Examiner*—Douglas M Willis
(74) *Attorney, Agent, or Firm*—Henry C. Jeanette

(57) ABSTRACT

Disclosed is a compound of the formula:

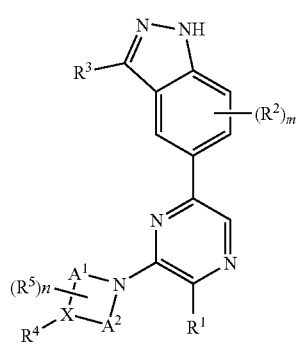

and the pharmaceutically acceptable salts thereof. Also disclosed are methods of treating protein kinase mediated diseases using the compound of formula 1.0. Also disclosed are methods of treating cancer using a compound of formula 1.0. The disclosed methods also include combination therapies wherein the compound of formula 1.0 is administered in combination with at least one addition pharmaceutically active ingredient.

14 Claims, No Drawings

SUBSTITUTED INDAZOLES OF FORMULA 1.0 THAT ARE KINASE INHIBITORS

REFERENCE TO RELATED APPLICATION

This Application claims the benefit of U.S. Provisional Application Ser. No. 60/788,465 filed Mar. 31, 2006.

FIELD OF THE INVENTION

The present invention relates to indazolylpyrazinyl compounds useful as protein kinase inhibitors, pharmaceutical compositions comprising such compounds, and methods of treatment using the compounds and compositions to treat conditions such as cancer and proliferative diseases.

BACKGROUND

Kinases are essential cellular signaling molecules. Mutations in kinases can lead to diseases or conditions including immunodeficiencies, cancers, cardiovascular diseases and endocrine disorders, such as Parkinson's disease, metabolic diseases, tumorigenesis, Alzheimer's disease, heart disease, diabetes, neurodegeneration, inflammation, kidney disease, atherosclerosis and airway disease.

Cancers result from deregulated signaling pathways that mediate cell growth and programmed cell death (apoptosis). Protein kinases are a large family of proteins that play an important role in signaling pathways that regulate a number of different cellular functions, such as cell growth, differentiation, and death (e.g., Kumar et al., *Expert Opin. Emerging Drugs* (2001) 6(2) pp. 1-13; U.S. Pat. Publ. No. 2003/0199511, WO 2004/030671, WO 2004/094386, WO 2004/096130, WO 2004/041162, WO 2004/022562, WO 2004/048343, and references cited therein). Protein kinases include those classified as tyrosine, serine/threonine (e.g., Akt or PKB), or dual specific, based on acceptor residue. Protein tyrosine kinases include intracellular domains of transmembrane growth factor receptors such as EGF receptor (EGFR), PDGF receptor (PDGFR), VEGF receptor (VEGFR), and FGF receptor (FGFR), and cytosolic kinases such as src, abl, and lck. Serine/threonine kinases include, for example, MAP kinase, MAPK kinase (MEK), Akt/PKB, Jun kinase (JNK), CDKs, protein kinase A (PKA) and protein kinase C (PKC).

Hyperactivity of protein kinases is implicated in a variety of human cancers. For example, the Akt2 kinase has been found to be over-expressed in ovarian tumors (J. Q. Cheung et al., *Proc. Natl. Acad. Sci. U.S.A.* 89: 9267-9271 (1992)) and pancreatic cancers (J. Q. Cheung et al., *Proc. Natl. Acad. Sci. U.S.A.* 93: 3636-3641 (1996)), and the Akt3 kinase was found to be over-expressed in breast and prostate cancer cell lines (Nakatani et al., *J. Biol. Chem.* 274: 21528-21532 (1999)).

Various protein kinase inhibitors have been shown to effectively treat certain cancers. For example, Gleevec™ (imantinib, Novartis), can be used to treat chronic myeloid leukemia (CML) (Kumar et al.), flavopiridol (Aventis) has been evaluated for treating mantle cell lymphoma and fludar refractory chronic lymphocytic leukemia, and a Raf kinase inhibitor (BAY-43-9006) has been evaluated for treating solid tumors and myeloid leukemia (WO 2004/022562).

Thus, drugs targeted against protein kinases represent a new generation of chemotherapy agents directed toward specific molecular targets, and thus have the potential for greater efficacy in treating various cancers, with fewer side effects than conventional chemotherapeutic agents.

U.S. Pat. No. 6,831,175 B2, issued Dec. 14, 2004 discloses compounds useful for inhibiting protein kinases. This patent discloses (see for example Columns 1-3) compounds of the formula (I):

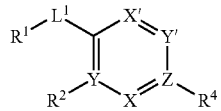

wherein, amongst other possibilities:

X is selected from the group consisting of $C(R^8)$ and N; wherein $R^8$ is selected from the group consisting of hydrogen, alkyl, amino, carboxy, cyano, halo, hydroxyl, and amido;

X' is selected from the group consisting of C and N;

Y is selected from the group consisting of C and N;

Y' is selected from the group consisting of $C(R^9)$ and N; wherein $R^9$ is selected from the group consisting of hydrogen and $-L^2-L^3(R^3)(R^6)$;

Z is selected from the group consisting of C and N;

provided that 0, 1, or 2 of X, X', Y, Y' and Z are N;

$L^1$ is, amongst other possibilities, a bond or $-C(R^{12})-$;

$L^2$ is, amongst other possibilities, a bond or $-C(R^{12})-$;

$L^3$ is, amongst other possibilities, a bond, alkylidene or alkylene;

$R^1$ is selected from the group consisting of aryl, heteroaryl, and heterocycle;

$R^2$ and $R^4$ are independently absent or selected from, amongst other possibilities, heteroaryl and heterocycle;

$R^3$ is absent or selected from, amongst other possibilities, heteroaryl or heterocycle;

$R^6$ is selected from, amongst other possibilities, heteroaryl or heterocycle; and $R^7$ is absent or selected from the group consisting of hydrogen, alkyl, cyanoalkenyl, and $-L^2-L^3(R^3)(R^6)$.

U.S. Pat. No. 6,831,175 B2 defines heteroaryl in Columns 17 to 18 and indazolyl is one of the exemplified heteroaryl groups (see line 3 in Column 18). U.S. Pat. No. 6,831,175 B2 defines heterocycle in the paragraph bridging Columns 18 to 19 and piperazinyl and piperidinyl are two of the exemplified heterocycle groups.

WO 2005/058876, published Jun. 30, 2005, discloses pyrazine derivatives as effective compounds against infectious diseases. The compounds disclosed are:

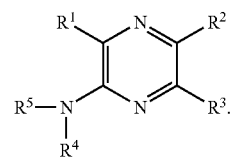

$R^3$ can be, amongst other possibilities, a substituted or unsubstituted heteroaryl. $R^4$ and $R^5$ amongst other possibilities, can be taken together to form a ring system (see page 3, for example). Indazolyl is one of the exemplified heteroaryl groups (see page 10, for example).

GB 2,400,101 A1 published Oct. 6, 2004, discloses compounds of the formula:

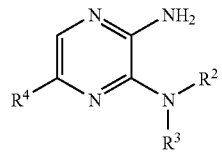

(see page 91, for example). $R^2$ and $R^3$, amongst other possibilities, may be joined to form the same ring system. $R^4$, amongst other possibilities, can be heteroaryl. Examples of the —$NR^2R^3$ are disclosed in Box 3 on page 101. Examples of the $R^4$ group are disclosed in Box 4 on page 101. Indazolyl is not amongst the exemplified $R^4$ groups in Box 4.

WO 02/060492, published Aug. 8, 2002, discloses methods of inhibiting protein tyrosine kinases including members of the JAK family. The methods disclose the administration of di-substituted pyrazines or disubstituted pyridines (see page 6, for example). Also disclosed are methods using substituted imidazo[1,2-a]pyrazines (see page 10, for example).

Various pharmaceutically active [1,2,4]triazines are known. For example, U.S. Pat. No. 4,560,687 and U.S. Pat. No. 4,311,701 provide 3,5-diamino-6-aryl-[1,2,4]triazines useful for treating CNS disorders; EP 0021121 provides 3-amino-6-aryl-[1,2,4]triazines useful for treating CNS disorders; U.S. Pat. No. 4,190,725 provides anti-inflammatory 5,6-diaryl-[1,2,4]triazines; U.S. Pat. No. 3,948,894 provides anti-inflammatory 3-amino-5,6-diaryl-[1,2,4]triazines; U.S. 2004/0102436 provides various 2-amino-5,6-diaryl-[1,2,4] triazine $PGI_2$ receptor agonists; WO 00/66568 provides various 3-aryl-[1,2,4]triazine pesticides; WO 2004/074266 provides various 3-phenylamino- or 3-halo-[1,2,4]triazine HIV replication inhibitors; WO 97/20827 provides various 3,5-diamino-6-fluorophenyl-[1,2,4]triazine as inhibitors of glutamate release from the central nervous system; U.S. Pat. No. 4,649,139 provides 3,5-diamino-6-aryl-[1,2,4]triazines useful as cardiovascular agents; WO 2004/096129 provides 5,6-diaryl-[1,2,4]triazines useful for inhibiting Akt; U.S. Pat. No. 6,159,974 and WO 98/42686 provide 3-pyridyl-6-aryl-[1,2,4]triazine LDL receptor gene expression promoters; WO 03/077921 provides various 5-amino-[1,2,4]triazines useful as protein kinase inhibitors; EP 0088593 and U.S. Pat. No. 4,585,861 provide various 3-heterocyclo-5,6-diaryl-[1,2,4] triazines useful as activators of gamma-aminobutyric acid and benzodiazepine binding in the central nervous system; DD 248363 provides ampicillin derivatives having a 1,2,4-triazinyl moiety; GB 759014 describes improved methods of preparing 3,5-diamino-6-aryl-[1,2,4]triazines; Abdel-Rahman et al., *Bollettino Chimico Farmaceutico* (1999), 138(4), 176-185, describe the synthesis of (triazinyl)triazines; Dinakaran et al., *Biological & Pharmaceutical Bulletin* (2003), 26(9), 1278-1282, describe the synthesis of 3-quinazolinone-[1,2,4]triazines; Heinisch, *Journal fuer Praktische Chemie (Leipzig)* (1969), 311(3), 438-444 describe the synthesis of morpholine-[1,2,4]triazines; Yoneda et al., *Chemical & Pharmaceutical Bulletin* (1978), 26(10), 3154-3160, describe the synthesis of 3-aryl-5,6-diamino-[1, 2,4]triazines; Yondea et al., *Chemical & Pharmaceutical Bulletin* (1973), 21(5), 926-930, describe the synthesis of [1,2, 4]triazine-6-carbothioamides; Li et al., *Huaxue Xuebao* (1980), 38(6), 581-583 describe 3-substituted-5-hydroxy-6-methyl-[1,2,4]triazines; Neunhoeffer et al., *Liebigs Annalen der Chemie* (1990), (7), 631-640 describe 3-pyridyl-5-alkynyloxy-[1,2,4]triazines; Pochat, *Tetrahedron Letters* (1981), 22(37), 3595-3596 describes 3,6-diaryl-5-hydroxy-[1,2,4] triazines; Heinisch, *Journal fuer Praktische Chemie (Leipzig)* (1987), 329(2), 290-300 describes [1,2,4]triazine-6-carboxylic acids; Li, *J. Org. Chem.* (1993), 58, 516-519 describes pyrrolyl [1,2,4]triazines; Paudler et al., *J. Org. Chem.* (1966), 31, 1720-1722 describe the synthesis of various [1,2,4]triazines; Benson et al., *J. Org. Chem.*, (1992), 57, 5285-5287 describe intramolecular cycloadditions of indole and [1,2,4] triazine; and Limanto et al., *Organic Letters* (2003), 5(13), 2271-2274 describe 5-substituted-3-amino-1,2,4,-triazines.

U.S. Pat. No. 6,982,274 discloses compounds that have JNK inhibitory action, said compounds having the formula:

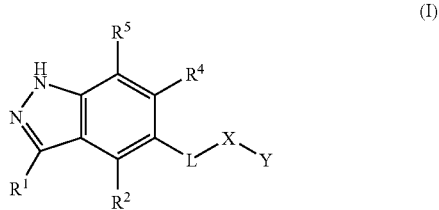

(I)

wherein:

$R^1$ is a $C_6$ to $C_{14}$ aromatic cyclic hydrocarbon group which may be substituted or a 5 to 14 membered aromatic heterocyclic group which may be substituted;

$R^2$, $R^4$, and $R^5$ each independently represent, a hydrogen atom, a halogen atom, a hydroxyl group, a cyano group, a nitro group, a carboxyl group, a $C_1$-$C_6$ alkyl group which may be substituted, a $C_1$-$C_6$ alkoxy group which may be substituted, a $C_2$-$C_7$ acyl group which may be substituted, a $C_2$-$C_7$ acyl group which may be substituted, —CO—$NR^{2a}R^{2b}$, —$NR^{2b}$CO—$R^{2a}$ or —$NR^{2a}R^{2b}$ (wherein $R^{2a}$ and $R^{2b}$ each independently represent a hydrogen atom or a $C_1$-$C_6$ alkyl group which may be substituted);

L, amongst other possibilities, can be a single bond (see Column 8);

X, amongst other possibilities, can be a single bond (see Column 8);

Y, amongst other possibilities, can be a 5- to 14-membered aromatic heterocyclic group which may be substituted (see Column 8).

U.S. Pat. No. 6,982,274 defines the 5- to 14-membered aromatic heterocyclic group in the paragraph bridging Columns 16 and 17. The examples of the 5- to 14-membered aromatic heterocyclic group includes, amongst others, pyrazinyl.

SUMMARY OF THE INVENTION

This invention provides substituted pyrazines that are kinase inhibitors. The substituted pyrazines of this invention are substituted with: (a) an indazolyl ring wherein the benzo moiety of said indazolyl ring is bonded to a carbon atom of said pyrazinyl ring, said indazolyl ring being optionally substituted; and (b) a heterocycloalkyl ring comprising at least one nitrogen atom, wherein said heterocycloalkyl ring is bonded to a carbon of said pyrazinyl ring through a ring nitrogen in said heterocycloalkyl ring, and wherein said heterocycloalkyl ring is bonded to the carbon of the pyrazinyl ring that is adjacent to the nitrogen that is adjacent to the carbon that said indazolyl ring is bonded to, and wherein said heterocycloalkyl ring is optionally substituted; and wherein the carbon on said pyrazinyl ring that is adjacent to said heterocycloalkyl ring is optionally substituted.

Thus, this invention provides compounds of formula 1.0:

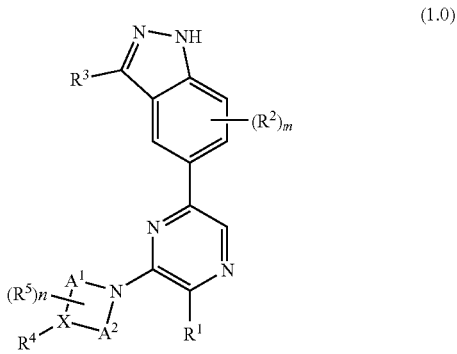

(1.0)

or the pharmaceutically acceptable salts thereof; wherein $R^1$, $R^2$, $R^3$, $R^4$, $R^5$, $A^1$, $A^2$, X, m and n are as defined below.

This invention also provides a compound selected from the group consisting of the final compounds of Examples 1 to 50, or a pharmaceutically acceptable salt thereof.

This invention also provides a compound selected from the group consisting of the final compounds of Examples 1, 2, 5, 8, 12, 18, 27, 29, 30, 31, 34, 35, 38, 41, 42, 43 and 50.

This invention also provides a compound that is the final compound of Example 2.

This invention also provides a compound that is the final compound of Example 18.

This invention also provides a compound that is the final compound of Example 42.

This invention also provides compounds of formula 1.0 in pure and isolated form.

This invention also provides the final compounds of Examples 1 to 50 in pure and isolated form.

This invention also provides a pharmaceutical composition comprising at least one (e.g., 1, 2, or 3, and preferably 1) compound of formula 1.0, or a pharmaceutically acceptable salt thereof, and a pharmaceutically acceptable carrier.

This invention also provides a pharmaceutical composition comprising a compound of formula 1.0, or a pharmaceutically acceptable salt thereof, and a pharmaceutically acceptable carrier.

This invention also provides a pharmaceutical composition comprising at least one (e.g., 1, 2, or 3, and preferably 1) final compound selected from the group consisting of the final compounds of Examples 1 to 50, or a pharmaceutically acceptable salt thereof, and a pharmaceutically acceptable carrier.

This invention also provides a pharmaceutical composition comprising a final compound selected from the group consisting of the final compounds of Examples 1 to 50, or a pharmaceutically acceptable salt thereof, and a pharmaceutically acceptable carrier.

This invention also provides a method of inhibiting protein kinases (such as, for example, a protein kinase selected from the group consisting of: AKT1, AKT2, and AKT3) in a patient in need of such treatment, said treatment comprising administering an effective amount of at least one compound (e.g., 1, 2, or 3, and preferably 1) of formula 1.0 to said patient.

This invention also provides a method of inhibiting protein kinases (such as, for example, a protein kinase selected from the group consisting of: AKT1, AKT2, and AKT3) in a patient in need of such treatment, said treatment comprising administering an effective amount of a compound of formula 1.0 to said patient.

This invention is also provides a method of inhibiting protein kinases (such as, for example, a protein kinase selected from the group consisting of: AKT1, AKT2, and AKT3) in a patient in need of such treatment, said treatment comprising administering an effective amount of at least one compound (e.g., 1, 2, or 3, and preferably 1), selected from the group consisting of the final compounds of Examples 1 to 50, to said patient.

This invention is also provides a method of inhibiting protein kinases (such as, for example, a protein kinase selected from the group consisting of: AKT1, AKT2, and AKT3) in a patient in need of such treatment, said treatment comprising administering an effective amount of a compound, selected from the group consisting of the final compounds of Examples 1 to 50, to said patient.

This invention also provides a method of treating a protein kinase mediated disease or disorder (e.g., a disease) in a patient in need of such treatment, said treatment comprising administering at least one compound (e.g., 1, 2, or 3, and preferably 1) of formula 1.0 to said patient.

This invention also provides a method of treating a protein kinase mediated disease or disorder (e.g., a disease) in a patient in need of such treatment, said treatment comprising administering a compound of formula 1.0 to said patient.

This invention also provides a method of treating a protein kinase mediated disease or disorder (e.g., a disease) in a patient in need of such treatment, said treatment comprising administering at least one compound (e.g., 1, 2, or 3, and preferably 1) selected from the group consisting of the final compounds of Examples 1 to 50 to said patient.

This invention also provides a method of treating a protein kinase mediated disease or disorder (e.g., a disease) in a patient in need of such treatment, said treatment comprising administering a compound selected from the group consisting of the final compounds of Examples 1 to 50 said patient.

This invention also provides a method of treating a proliferative disease (e.g., cancer) in a patient in need of such treatment, said treatment comprising administering at least one compound (e.g., 1, 2, or 3, and preferably 1) of formula 1.0 to said patient.

This invention also provides a method of treating a proliferative disease (e.g., cancer) in a patient in need of such treatment, said treatment comprising administering a compound of formula 1.0 to said patient.

This invention also provides a method of treating a proliferative disease (e.g., cancer) in a patient in need of such treatment, said treatment comprising administering at least one compound (e.g., 1, 2, or 3, and preferably 1) selected from the group consisting of the final compounds of Examples 1 to 50 to said patient.

This invention also provides a method of treating a proliferative disease (e.g., cancer) in a patient in need of such treatment, said treatment comprising administering a compound selected from the group consisting of the final compounds of Examples 1 to 50 to said patient.

This invention also provides methods of treating kinase mediated diseases or conditions, and methods of treating proliferative diseases (e.g., cancer), as described herein, wherein said treatment comprises the administration of the compounds of this invention (e.g., the compounds of formula 1.0, and the compounds of Examples 1 to 50) in combination with the administration (e.g., concurrently or sequentially) of at least one (e.g., 1, 2, or 3, or 1 or 2, or 1) addition pharmaceutically active ingredient. Examples of said pharmaceutically active ingredients include, but are not limited to: chemotherapeutic agents (also known as antineoplastic agents, the cytotoxic agents herein are chemotherapeutic agents), second kinase inhibitors (i.e., kinase inhibitors in addition to the compounds of this invention), estrogen receptor modulators, androgen receptor modulators, retinoid receptor modulators, cyctotoxic agents, prenyl-protein transferase inhibitors (e.g., farnesyl protein transferase inhibitors), HMG-CoA reductase inhibitors, HIV protease inhibitors, reverse transcriptase inhibitors, angiogenesis inhibitors, inhibitors of inherent multidrug resistance, anti-emetic agents, agents useful in the treatment of anemia, agents useful in the treatment of neutropenia, and immunologic-enhancing drugs.

Thus, this invention also provides a method of treating a proliferative disease (e.g., cancer) in a patient in need of such treatment, said treatment comprising administering at least one compound (e.g., 1, 2, or 3, and preferably 1) of formula 1.0 to said patient in combination (e.g., concurrently or sequentially) with at least one (e.g., 1, 2, or 3, or 1 or 2, or 1) other pharmaceutically active ingredient selected from the group consisting of: chemotherapeutic agents (also known as antineoplastic agents, the cytotoxic agents herein are chemotherapeutic agents), second kinase inhibitors (i.e., kinase inhibitors in addition to the compounds of this invention), estrogen receptor modulators, androgen receptor modulators, retinoid receptor modulators, cyctotoxic agents, prenyl-protein transferase inhibitors (e.g., farnesyl protein transferase inhibitors), HMG-COA reductase inhibitors, HIV protease inhibitors, reverse transcriptase inhibitors, angiogenesis inhibitors, inhibitors of inherent multidrug resistance, anti-emetic agents, agents useful in the treatment of anemia, agents useful in the treatment of neutropenia, and immunologic-enhancing drugs.

This invention also provides a method of treating a proliferative disease (e.g., cancer) in a patient in need of such treatment, said treatment comprising administering a compound of formula 1.0 to said patient in combination (e.g., concurrently or sequentially) with at least one (e.g., 1, 2, or 3, or 1 or 2, or 1) other pharmaceutically active ingredient selected from the group consisting of: chemotherapeutic agents (also known as antineoplastic agents, the cytotoxic agents herein are chemotherapeutic agents), second kinase inhibitors (i.e., kinase inhibitors in addition to the compounds of this invention), estrogen receptor modulators, androgen receptor modulators, retinoid receptor modulators, cyctotoxic agents, prenyl-protein transferase inhibitors (e.g., farnesyl protein transferase inhibitors), HMG-COA reductase inhibitors, HIV protease inhibitors, reverse transcriptase inhibitors, angiogenesis inhibitors, inhibitors of inherent multidrug resistance, anti-emetic agents, agents useful in the treatment of anemia, agents useful in the treatment of neutropenia, and immunologic-enhancing drugs.

This invention also provides a method of treating a proliferative disease (e.g., cancer) in a patient in need of such treatment, said treatment comprising administering at least one compound (e.g., 1, 2, or 3, and preferably 1) selected from the group consisting of the final compounds of Examples 1 to 50 to said patient in combination (e.g., concurrently or sequentially) with at least one (e.g., 1, 2, or 3, or 1 or 2, or 1) other pharmaceutically active ingredient selected from the group consisting of: chemotherapeutic agents (also known as antineoplastic agents, the cytotoxic agents herein are chemotherapeutic agents), second kinase inhibitors (i.e., kinase inhibitors in addition to the compounds of this invention), estrogen receptor modulators, androgen receptor modulators, retinoid receptor modulators, cyctotoxic agents, prenyl-protein transferase inhibitors (e.g., farnesyl protein transferase inhibitors), HMG-COA reductase inhibitors, HIV protease inhibitors, reverse transcriptase inhibitors, angiogenesis inhibitors, inhibitors of inherent multidrug resistance, anti-emetic agents, agents useful in the treatment of anemia, agents useful in the treatment of neutropenia, and immunologic-enhancing drugs.

This invention also provides a method of treating a proliferative disease (e.g., cancer) in a patient in need of such treatment, said treatment comprising administering a compound selected from the group consisting of the final compounds of Examples 1 to 50 to said patient in combination (e.g., concurrently or sequentially) with at least one (e.g., 1, 2, or 3, or 1 or 2, or 1) other pharmaceutically active ingredient selected from the group consisting of: chemotherapeutic agents (also known as antineoplastic agents, the cytotoxic agents herein are chemotherapeutic agents), second kinase inhibitors (i.e., kinase inhibitors in addition to the compounds of this invention), estrogen receptor modulators, androgen receptor modulators, retinoid receptor modulators, cyctotoxic agents, prenyl-protein transferase inhibitors (e.g., farnesyl protein transferase inhibitors), HMG-COA reductase inhibitors, HIV protease inhibitors, reverse transcriptase inhibitors, angiogenesis inhibitors, inhibitors of inherent multidrug resistance, anti-emetic agents, agents useful in the treatment of anemia, agents useful in the treatment of neutropenia, and immunologic-enhancing drugs.

Those skilled in the art will appreciate that in the above described methods include the administration of the compounds of formula 1.0, and the compounds of Examples 1 to 50, as a pharmaceutical composition comprising the compound (or compounds) and a pharmaceutically acceptable carrier.

DETAILED DESCRIPTION OF THE INVENTION

As used above, and throughout this disclosure, the following terms, unless otherwise indicated, shall be understood to have the following meanings:

"Chemotherapeutic agents" are also known as antineoplastic agents, and the cytotoxic agents herein are chemotherapeutic agents).

"One or more" means 1, or more than 1, for example, 1, 2, or 3, or 1 or 2, or 1.

"At least one" means 1, or more than 1, for example, 1, 2, or 3, or 1 or 2, or 1.

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkynylene" means a difunctional group obtained by removal of a hydrogen from an alkynyl group that is defined above. Non-limiting examples of alkenylene include —C≡C— and —CH$_2$C≡C—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" ("cyclyl") means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Cycloalkylene" means a difunctional group obtained by removal of a hydrogen atom from a cycloalkyl group that is defined above. Non-limiting examples of cycloalkylene include:

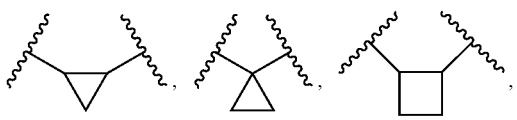

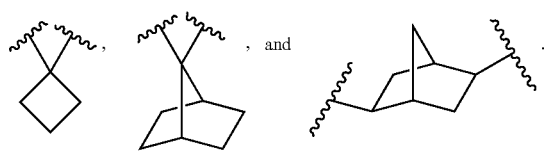

"Halogen" means fluorine, chlorine, bromine, or iodine. Preferred are fluorine, chlorine and bromine.

"Halo" means fluoro, chloro, bromo, or iodo. Preferred are fluoro, chloro and bromo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and SO$_2$Y$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

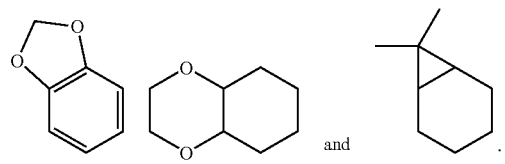

"Ring system substituent" also includes substituents off of an heterocyclyl ring, wherein said substituents on adjacent carbon atoms, on a carbon atom and an adjacent heteroatom, or on a single carbon atom, together with the carbon atom(s) and/or the combination of the carbon atom and the adjacent heteroatom to which said substituents are attached, form a four to seven-membered cycloalkyl, cycloalkenyl, heterocyclyl, aryl or heteroaryl ring. Non-limiting examples of such ring-system substituent together with the heterocyclyl ring from which the substituents are derived include:

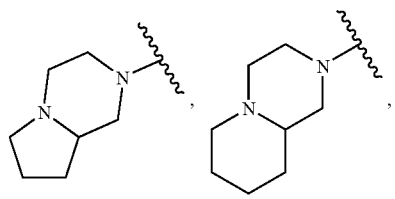

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" ("heteroalkyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of partially unsaturated monocyclic heterocyclyl rings include, for example, thiazolinyl, and the like.

"Heterocyclyl" may also mean a ring system, as described above, that is substituted with a single moiety (e.g., oxo) which replaces two available hydrogens on the same carbon atom on a ring system." An example of such moiety is pyrrolidone:

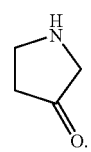

"Heterocyclylalkyl" means a heterocyclyl moiety as defined above linked via an alkyl moiety (defined above) to a parent core. Non-limiting examples of suitable heterocycylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond.

There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

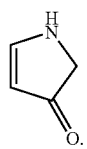

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

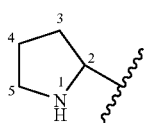

there is no —OH attached directly to carbons marked 2 and 5.

It should also be noted that tautomeric forms such as, for example, the moieties:

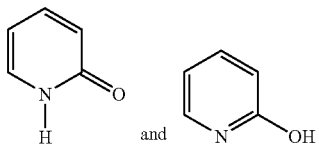

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Haloalkyl" means an alkyl group, as defined above, that is substituted with one or more halo atoms, as defined above. An examples include, but are not limited to, —$CF_3$.

"heteroarylalkylene-" means a heteroaryl group, as defined above, that is bound to an alkylene group, as defined above, wherein said alkylene group is bound to the rest of the molecule.

"cyclylalkylene-" means a cyclyl group, as defined above, that is bound to an alkylene group, as defined above, wherein said alkylene group is bound to the rest of the molecule.

"arylalkylene-" means an aryl group, as defined above, that is bound to an alkylene group, as defined above, wherein said alkylene group is bound to the rest of the molecule.

"heterocyclylalkylene-" means a heterocyclyl group, as defined above, that is bound to an alkylene group, as defined above, wherein said alkylene group is bound to the rest of the molecule.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula 1.0 or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino) ethyl having from 4 to 10 carbon atoms, 3-phthalidyl, 4-crotonol-actonyl, gamma-butyrolacton-4-yl, di-N,N-$(C_1-C_2)$ alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino $(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxy-carbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O) $(OH)_2$, —P(O)(O$(C_1-C_6)$alkyl$)_2$ or glycosyl (the radical resulting from the removal of a hydroxyl group of the hemiacetal form of a carbohydrate), and the like.

If a compound of Formula 1.0 incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N- or di-N,N-$(C_1-C_6)$alkylaminoalkyl, —C($Y^4$)$Y^5$ wherein $Y^4$ is H or methyl and $Y^5$ is mono-N- or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates.

Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula 1.0 can form salts which are also within the scope of this invention. Reference to a compound of Formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1.0 may be formed, for example, by reacting a compound of Formula 1.0 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1)1-19; P. Gould, *International J. of Pharmaceutics* (1986), 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula 1.0, and salts, solvates, esters and prodrugs thereof, may exist in their tautomeric form (for example, as an amide or imino ether). All such tautomeric forms are contemplated herein as part of the present invention.

The compounds of Formula 1.0 may contain asymmetric or chiral centers, and, therefore, exist in different stereoisomeric forms. It is intended that all stereoisomeric forms of the compounds of Formula 1.0 as well as mixtures thereof, including racemic mixtures, form part of the present invention. In addition, the present invention embraces all geometric and positional isomers. For example, if a compound of Formula 1.0 incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula 1.0 may be atropisomers (e.g., substituted biaryls) and are considered as part of this invention. Enantiomers can also be separated by use of chiral HPLC column.

It is also possible that the compounds of Formula 1.0) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula 1.0 incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula 1.0) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula 1.0 can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula 1.0, and of the salts, solvates, esters and prodrugs of the compounds of Formula 1.0, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

The compounds of Formula 1.0, or pharmaceutically acceptable salts, solvates, or esters thereof, according to the invention have pharmacological properties; in particular, the compounds of Formula 1.0 can be kinase inhibitors, including but not limited to inhibitors of tyrosine protein kinases, inhibitors of serine/threonine protein kinases, and inhibitors of dual specific protein kinases.

The compounds of Formula 1.0 of the present invention, or pharmaceutically acceptable salts, solvates, or esters thereof, are useful in treating diseases or conditions including immunodeficiencies, cancers, cardiovascular diseases and endocrine disorders, such as Parkinson's disease, metabolic diseases, tumorigenesis, Alzheimer's disease, heart disease, diabetes, neurodegeneration, proliferative disorders, inflammation, kidney disease, atherosclerosis and airway disease, particularly cancers and proliferative disorders. Such diseases are examples of protein kinase mediated diseases.

Examples of the cancers treatable in the methods of this invention include, for example, melanoma, pancreatic cancer, thryroid cancer, colorectal cancer, lung cancer (such as, for example, non small cell lung cancer), breast cancer, ovarian cancer, colon cancer (e.g., colorectal cancer), myeloid leukemias (e.g., AML, CML, and CMML), myelodysplastic syndrome (MDS), bladder carcinoma, epidermal carcinoma, prostate cancer, head and neck cancers (e.g., squamous cell cancer of the head and neck), brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, and anaplastic thyroid carcinoma In one embodiment the methods of this invention, the cancer being treated is selected from the group consisting of: lung cancer, pancreatic cancer, colon cancer, breast cancer, ovarian cancer, brain cancer (e.g., gliomas), and prostate cancer.

The compounds of Formula 1.0, or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of Formula 1.0, or pharmaceutically acceptable salts, solvates, or esters thereof, can be administered orally or parenterally, including intravenous, intramuscular, interperitoneal, subcutaneous, rectal, or topical routes of administration.

Pharmaceutical compositions comprising at least one compound of Formula 1.0, or a pharmaceutically acceptable salt, solvate, or ester thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of Formula 1.0, or a pharmaceutically acceptable salt, solvate, or ester thereof, administered to a patient can be determined by a physician based on the age, weight, and response of the patient, as well as by the severity of the condition treated. For example, the amount of compound of Formula 1.0, or a pharmaceutically acceptable salt, solvate, or ester thereof, administered to the patient can range from about 0.1 mg/kg body weight per day to about 60 mg/kg/d, preferably about 0.5 mg/kg/d to about 40 mg/kg/d.

The compounds of Formula 1.0, or pharmaceutically acceptable salts, solvates, or esters thereof, can also be administered in combination with other therapeutic agents. For example one or more compounds of Formula 1.0, or pharmaceutically acceptable salts, solvates, or esters thereof, can be administered with one or more additional active ingredients selected from the group consisting of a second kinase inhibitor, an estrogen receptor modulator, an androgen receptor modulator, a retinoid receptor modulator, a chemotherapeutic agent (e.g., a cyctotoxic agent), a prenyl-protein transferase inhibitor, aromatase inhibitors, antiestrogens, LHRH analogues, an HMG-COA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing drug. Examples of such additional active ingredients may be found in *Cancer Principles and Practice of Oncology*, V. T. Devita and S. Hellman (Eds.), 6$^{th}$ Ed. (Feb. 15, 2001), Lippincott Williams & Wilkins, Publ.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCI, such as Tarceva), Bevacizumab (e.g., Avastin), Cetuximab (e.g., Erbitux), and Bortezomib (e.g., Velcade)."

Thus, one embodiment of this invention is directed to a method of treating breast cancer in a patient in need of such treatment, said treatment comprising administering to said patient at least one compound of formula 1.0 in combination with (e.g., concurrently or sequentially) an antihormonal agent selected from the group consisting of: (a) aromatase inhibitors, (b) antiestrogens, and (c) LHRH analogues; and said treatment optionally including the administration of at least one chemotherapeutic agent (see, for example, WO 2005/046691 published May 26, 2005).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include but are not limited to finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include but are not limited to bexarotene, tretinoin, 13-cis-retinoic acid, 9-cis-retinoic acid, α-difluoromethylornithine, ILX23-7553,trans-N-(4'-hydroxyphenyl) retinamide, and N-4-carboxyphenylretinamide.

"Cytotoxic/cytostatic agents" refer to compounds which cause cell death or inhibit cell proliferation primarily by interfering directly with the cell's functioning or inhibit or interfere with cell myosis, including but not limited to alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro (2-methyl-pyridine) platinum, benzylguanine, glufosfamide, GPX100, (trans,trans,trans)-bis-mu-(hexane-1,6-diamine)-mu-[diamine-platinum(H)]bis[diamine(chloro) platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Antiproliferative agents" include but are not limited to antisense RNA and DNA oligonucleotides such as G3139, ODN698, RVASKRAS, GEM231, and INX3001, and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine,N-[5-(2,3-dihydro-benzofuryl)sulfonyl]-N'-(3,4-dichlorophenyl) urea, N6-[4-deoxy-4-[N2-[2(E),4(E)-tetradecadienoyl] glycylamino]-L-glycero-B-L-manno-heptopyranosyl] adenine, aplidine, ecteinascidin, troxacitabine, 4-[2-amino-4-oxo-4, 6,7,8-tetrahydro-3H-pyrimidino[5,4-b][1,4] thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabinofuranosyl cytosine, 3-aminopyridine-2-carboxaldehydethiosemicarbazone and trastuzumab.

"Prenyl-protein transferase inhibitor" refers to a compound which inhibits any one or any combination of the prenyl-protein transferase enzymes, including but not limited to farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (+)-6-[amino(4-chlorophenyl)(1-methyl-1H-imidazol-5-yl)methyl]4-(3-chlorophenyl)-I-methyl-2(1H)-quinolinone, (−)-6-[amino(4-chlorophenyl)(1-methyl-(1H)-imidazol-5-yl)methyl]4-(3-chlorophenyl)-1-methyl-2(1H)-quinolinone, (+)-6-[amino(4-chlorophenyl) (1-methyl-IH-imidazol-5-yl)methyl]-4-(3-chlorophenyl)-I-methyl-2(IH)-quinolinone, 5(S)-n-butyl-1-(2,3- dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)4-[1-(4-cyanobenzyl)-2-methyl-5-imidazolylmethyl]-2-piperazinone, 1-(2,2-diphenylethyl)-3-[N-(1-(4-cyanobenzyl)-IH-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-15-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-6, 10-metheno-22H-benzo[d]imidazo[4,3-k][1,6,9,12] oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and ( )-19,20-dihydro-3-methyl-19-oxo-5H-18, 21-ethano-12,14-etheno-6,10-metheno-22H-benzo[d] imidazo[4,3-k][1,6,9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO95/25086, WO96/05529, WO 96/06138, WO 96/06193, WO 96/16443, WO96/21701, WO 96/21456, WO96/22278, WO 96/24611, WO 96/24612, WO 96/05168, WO 96/05169, WO 96/00736, U.S. Pat. No. 5,571,792, WO 96/17861, WO 96/33159, WO96/34850, WO96/34851, WO 96/30017, WO 96/30018, WO 96/30362, WO 96/30363, WO 96/31111, WO 96/31477, WO 96/31478, WO 96/31501, WO 97/00252, WO97/03047, WO97/03050, WO97/04785, WO97/02920, WO97/17070, WO97/23478, WO97/26246, WO97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"HMG-COA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-COA reductase inhibitor" and "inhibitor of HMG-CoA reductase" have the same meaning when used herein. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180, 589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885, 314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention. In HMG-CoA reductase inhibitors where an open-acid form can exist, salt and ester forms may preferably be formed from the open-acid and all such forms are included within the meaning of the term "HMG-CoA reductase inhibitor".

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-I/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475(1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105: 141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in Clin. Chem. La. Med. 38: 679-692 (2000)). Examples of such agents that modulate or inhibit the coagulation and fibrinolysis pathways include, but are not limited to, heparin (see Thromb. Haemost. 80:10-23 (1998)), low molecular weight heparin and carboxypeptidase U inhibitors (also known as inhibitors of active thrombin activatable fibrinolysis inhibitor [TAFIa]) (see Thrombosis Res. 101: 329-354 (2001)). TAFIa inhibitors have been described in U.S. Ser. Nos. 60/310,927 (filed Aug. 8, 2001) and 60/349,925 (filed Jan. 18,2002).

An "inhibitor of inherent multidrug resistance" (MDR), in particular MDR associated with high levels of expression of transporter proteins. Can include, for example, inhibitors of p-glycoprotein (P-gp), such as LY335979, XR9576, OC144-093, R101922, VX853 and PSC833 (valspodar).

"Anti-emetic agents" may include, for example, neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an anti-dopaminergic, such as the phenothiazines (for example prochlorperazine, fluphenazine, thioridazine and mesoridazine), metoclopramide or dronabinol.

"Anemia treatment agents" include, for example, a continuous erythropoiesis receptor activator (such as epoetin alfa).

An "agent useful in the treatment of neutropenia" can include, for example, a hematopoietic growth factor which regulates the production and function of neutrophils such as a human granulocyte colony stimulating factor, (G-CSF). Examples of a G-CSF include filgrastim.

An "immunologic-enhancing drug" can include, for example, levamisole, isoprinosine and Zadaxin.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Predniso-lone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

Methods for the safe and effective administration of most of the "additional pharmaceutically active ingredients" (e.g., the cytotoxic agents or chemotherapeutic agents) are known to those skilled in the art. In addition, their administration is described in the standard literature. For example, the administration of many of the chemotherapeutic agents is described in the "Physicians' Desk Reference" (PDR), see for example the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), the Physician's Desk Reference, 57th Edition, 2003 (published by Thompson PDR, Montvale, N.J. 07645-1742), and the Physician's Desk Reference, 60$^{th}$ Edition, 2006 (published by Thompson PDR, Montvale, N.J. 07645-1742); the disclosures of each being incorporated herein by reference thereto.

For example, the compound of formula 1.0 (e.g., a pharmaceutical composition comprising the compound of formula 1.0); can be administered orally (e.g., in one embodiment as a capsule, and in another embodiment a tablet), and the chemotherapeutic agents (e.g., cytotoxic agents) can be administered intravenously, usually as an IV solution. The use of a pharmaceutical composition comprising more than one drug is within the scope of this invention.

The compound of formula 1.0 and the "additional pharmaceutically active ingredient" (e.g., chemotherapeutic agents) are administered in therapeutically effective dosages to obtain clinically acceptable results, e.g., reduction or elimination of symptoms or of the tumor. Thus, the compound of formula 1.0 and chemotherapeutic agents can be administered concurrently or consecutively in a treatment protocol. The administration of the "additional pharmaceutically active ingredient" (e.g., chemotherapeutic agents) can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment.

Those skilled in the art will appreciate that treatment protocols can be varied according to the needs of the patient. The methods of this invention include continuous and discontinuous treatment protocols well known in the art. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of this invention can be administered orally, preferably as a solid dosage form (e.g., in one embodiment as a capsule, and in another as a table), and while the total therapeutically effective daily dose can be administered in one to four, or one to two divided doses per day, generally, the therapeutically effective dose is given once or twice a day, and in one embodiment twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be continuously dosed or used until releapse or toxicity. See for example Mitsiades et al., "Apoptotic signaling induced by immunomodulatory thalidomide analoqs in human multiple myeloma cells;therapeutic implications", Blood, 99(12):4525-30, Jun. 15, 2002, the disclosure of which is incorporated herein by reference thereto.

The FPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®), for example, can be administered once per week in an amount of about 50 to about 100 mg/m$^2$ and in another example about 60 to about 80 mg/m$^2$. In another example Paclitaxel (e.g., Taxol®) can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m².

In another example Carboplatin can be administered once per week in an amount to provide an AUC of about 2 to about 3. In another example Carboplatin can be administered once every three weeks in an amount to provide an AUC of about 5 to about 8.

This invention provides compounds of formula 1.0:

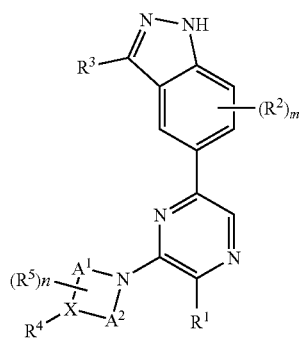

(1.0)

or the pharmaceutically acceptable salts thereof; wherein:
m is 0, 1, 2, or 3 (preferably, 0);
n is 0, 1, 2, 3 or 4 (preferably 1);
$A^1$ represents a one, two, three, or four carbon chain;
$A^2$ represents a one, two, three, or four carbon chain;
X is CH or N, provided that when X is N, then $R^4$ is not —$N(R^6)_2$, —$OR^6$, —$N(R^6)C(O)R^6$ or —$N(R^6)S(O)_2R^6$;
$R^1$ is selected from the group consisting of:
(1) H,
(2) —$NR^{20}R^{22}$,
(3) —$C(O)NR^{20}R^{22}$,
(4) —$C(O)OR^{41}$,
(5) -alkylene-aryl,
(6) -alkylene-heteroaryl,
(7) -alkylene-heterocyclyl,
(8) alkyl (e.g., $C_1$ to $C_6$ alkyl),
(9) substituted -alkylene-aryl,
(10) substituted -alkylene-heteroaryl,
(11) substituted -alkylene-heterocyclyl,
(12) substituted alkyl (e.g., substituted $C_1$ to $C_6$ alkyl),
(13) aryl,
(14) heteroaryl,
(15) heterocyclyl,
(16) substituted aryl,
(17) substituted heteroaryl, and
(18) substituted heterocyclyl; and
wherein examples of said alkylene moiety of said $R^1$ substituent include, for example, —$(CH_2)_3$—, —$(CH_2)_2$—, and —$CH_2$—, and in one example —$(CH_2)_2$—, and in another example —$CH_2$—; and
wherein:
(A) said substituted $R^1$ substituents (9), (10), (11), (16), (17) and (18) are substituted with 1 to 3 substituents independently selected from the group consisting of: (1) alkyl (e.g., $C_1$ to $C_6$ alkyl), (2) haloalkyl (e.g., halo($C_1$ to $C_6$)alkyl, such as, for example, a halo($C_1$ to $C_6$)alkyl having one or more halo moieties independently selected from the group consisting of F, Cl and Br), (3) halo (e.g., F, Cl and Br), (4) alkoxy (e.g., $C_1$ to $C_6$ alkoxy, e.g., —$OCH_3$), and (5) CN, and wherein said substituted $R^1$ substituents include, for example:

(a) substituents wherein the alkylene moiety is substituted and the remainder of the $R^1$ substituent is unsubstituted,
(b) substituents wherein the alkylene moiety is unsubstituted and the remainder of the $R^1$ substituent is substituted, and
(c) substituents wherein the alkylene moiety and the remainder of the $R^1$ substituent are both substituted with independently selected substituents);
(B) said substituted alkyl $R^1$ substituent (12) is substituted with 1 to 3 substituents selected from the group consisting of: (1) alkoxy (e.g., $C_1$ to $C_6$ alkoxy, e.g., —$OCH_3$), (2) halo (e.g., F, Cl and Br), (3) haloalkyl (e.g., halo($C_1$ to $C_6$)alkyl, such as, for example, a halo($C_1$ to $C_6$)alkyl having one or more halo moieities independently selected from the group consisting of F, Cl and Br), and (4) CN; and
(C) $R^{41}$ is selected from the group consisting of: (1) alkyl (e.g., $C_1$ to $C_6$ alkyl), (2) aryl, (3) heteroaryl, (4) cycloalkyl (e.g., $C_3$ to $C_6$ cycloalkyl), (5) substituted alkyl (e.g., substituted $C_1$ to $C_6$ alkyl), (6) substituted aryl, (7) substituted heteroaryl, and (8) substituted cycloalkyl (e.g., substituted $C_3$ to $C_6$ cycloalkyl); and wherein said substituted $R^{41}$ substituents are substituted with 1 to 3 substituents independently selected from the group consisting of: (1) alkyl (e.g., $C_1$ to $C_6$ alkyl), (2) haloalkyl (e.g., halo($C_1$ to $C_6$)alkyl, such as, for example, a halo($C_1$ to $C_6$)alkyl having one or more halo moieities independently selected from the group consisting of F, Cl and Br), (3) halo (e.g., F, Cl and Br), and (4) alkoxy (e.g., $C_1$ to $C_6$ alkoxy, e.g., —$OCH_3$);
$R^2$ is selected from the group consisting of:
(1) halo (e.g., F, Cl and Br, and in one example F),
(2) alkyl (e.g., $C_1$ to $C_6$alkyl, such as, for example, $C_1$ to $C_3$alkyl, such as, for example, methyl),
(3) substituted alkyl (e.g., substituted $C_1$ to $C_6$alkyl, such as, for example, substituted $C_1$ to $C_3$alkyl),
(4) haloalkyl (e.g., halo($C_1$ to $C_6$)alkyl, such as, for example, a halo($C_1$ to $C_6$)alkyl having one or more halo moieities independently selected from the group consisting of F, Cl and Br),
(5) —CN,
(6) —$NH_2$,
(7) —NH(alkyl) (e.g., —NH($C_1$ to $C_6$)alkyl),
(8) —$N(alkyl)_2$ (e.g., —$N((C_1$ to $C_6)alkyl)_2$) wherein each alkyl moiety is independently selected,
(9) —OH, and
(10) alkoxy (e.g., $C_1$ to $C_6$ alkoxy, e.g., —$OCH_3$); and wherein said substituted alkyl $R^2$ substituent (3) is substituted with 1 to 3 substituents selected from the group consisting of: (a) alkoxy (e.g., $C_1$ to $C_6$ alkoxy, e.g., —$OCH_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieities independently selected from the group consisting of F, Cl and Br), and (d) CN;
$R^3$ is selected from the group consisting of:
(1) halo (e.g., F, Cl and Br, and in one example F),
(2) alkyl (e.g., $C_1$ to $C_6$alkyl, such as, for example, $C_1$ to $C_2$alkyl, such as, for example, methyl),
(3) substituted alkyl (e.g., substituted $C_1$ to $C_6$alkyl, such as, for example, substituted $C_1$ to $C_2$alkyl),
(4) aryl,
(5) substituted aryl,
(6) heteroaryl,
(7) substituted heteroaryl, (8) haloalkyl (e.g., halo($C_1$ to $C_6$)alkyl, such as, for example, a halo($C_1$ to $C_6$)alkyl having one or more halo moieities independently selected from the group consisting of F, Cl and Br),
(9) alkenyl (e.g., $C_2$ to $C_6$alkenyl, such as, for example, $C_2$ to $C_3$alkenyl),
(10) alkynyl (e.g., $C_2$ to $C_6$alkynyl, such as, for example, $C_2$ to $C_3$alkynyl),
(11) heterocyclyl,
(12) substituted heterocyclyl,
(13) —$NH_2$,
(14) —NH(alkyl) (e.g., —NH($C_1$ to $C_6$)alkyl), and
(15) —$N(alkyl)_2$ (e.g., —N(($C_1$ to $C_6$)alkyl)$_2$) wherein each alkyl moiety is independently selected; and wherein:
(A) said substituted alkyl $R^3$ substituent (3) is substituted with 1 to 3 substituents selected from the group consisting of: (a) alkoxy (e.g., $C_1$ to $C_6$ alkoxy, e.g., —$OCH_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieities independently selected from the group consisting of F, Cl and Br), and (d) CN, and
(B) said substituted $R^3$ substituents (5), (6), and (12) are substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieities independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN;

$R^4$ is selected from the group consisting of:
(1) H,
(2) alkyl (e.g., $C_1$ to $C_6$alkyl, such as, for example, $C_1$ to $C_4$ alkyl, such as, for example, —$CH_3$),
(3) substituted alkyl (e.g., substituted $C_1$ to $C_6$ alkyl),
(4) alkenyl (e.g., $C_2$ to $C_6$alkenyl, such as, for example, —$CH_2$—CH=$CH_2$),
(5) alkynyl (e.g., $C_2$ to $C_6$alkynyl, such as, for example, —$CH_2$—C≡CH),
(6) —$N(R^6)_2$ (such as, for example, —$NH_2$),
(7) —$OR^6$ (such as, for example, —OH),
(8) $N(R^6)_2$alkylene- (e.g., $N(R^6)_2$($C_1$ to $C_6$)alkylene-, such as, for example, —$CH_2NH_2$, and —$(CH_2)_2NH_2$), provided that when X is N then said alkylene moiety is at least 2 (e.g., 2-6, and preferably 2) carbons in length (examples include —$CH_2NH_2$ when X is CH, and —$(CH_2)_2NH_2$ when X is N),
(9) $N(R^6)_2$-(substituted alkylene)- (e.g., $N(R^6)_2$(substituted $C_1$ to $C_6$)alkylene-), provided that when X is N then said alkylene moiety is at least 2 (e.g., 2-6, and preferably 2) carbons in length,
(10) $R^6$O-alkylene- (e.g., $R^6$O-($C_1$ to $C_6$)alkylene, such as, for example, —$CH_2OH$, and —$(CH_2)_2OH$), provided that when X is N then said alkylene moiety is at least 2 (e.g., 2-6, and preferably 2) carbons in length, (examples include —$CH_2OH$ when X is CH, and —$(CH_2)_2OH$ when X is N),
(11) $R^6$O-(substituted alkylene)- (e.g., $R^6$O-(substituted $C_1$ to $C_6$)alkylene), provided that when X is N then said alkylene moiety is at least 2 (e.g., 2-6, and preferably 2) carbons in length,
(12) aryl (e.g., phenyl),
(13) substituted aryl (e.g., substituted phenyl),
(14) arylalkylene- (e.g., aryl($C_1$ to C6)alkylene-, such as, for example, aryl-$CH_2$—, such as, for example, phenyl-$CH_2$— (i.e., benzyl)),
(15) substituted arylalkylene- (e.g., substituted aryl($C_1$ to $C_6$)alkylene-, such as, for example, substituted benzyl),
(16) cyclyl (i.e., cycloalkyl, such as $C_3$ to $C_{20}$ cycloalkyl, and preferably $C_3$ to $C_{10}$ cycloalkyl), said cyclyl (cycloalkyl) substituent comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine,
(17) substituted cyclyl (i.e., substituted cycloalkyl, such as substituted $C_3$ to $C_{20}$ cycloalkyl, and preferably substituted $C_3$ to $C_{10}$ cycloalkyl), said substituted cycylyl (substituted cycloalkyl) substituent comprising substituted monocyclic and substituted polycyclic (e.g., substituted bicyclic) rings, said substituted monocyclic rings generally comprising a $C_3$ to $C_8$ monocyclic ring (e.g., substituted cyclohexyl), and said substituted polycyclic (e.g., substituted bicyclic) rings generally comprising a $C_6$ to $C_{10}$ bicyclic ring, examples of said substituted polycyclic rings include, for example, substituted decaline and substituted adamantine,
(18) heterocyclyl (i.e., heterocycloalkyl, such as a 3 to 10 membered ring), comprising at least one (e.g., 1 to 3, or 1 to 2, or 1) heteroatom selected from the group consisting of: O, S, and N, such as, for example, piperdinyl,
(19) substituted heterocyclyl (i.e., substituted heterocycloalkyl, such as a substituted 3 to 10 membered ring), comprising at least one (e.g., 1 to 3, or 1 to 2, or 1) heteroatom selected from the group consisting of: O, S, and N, such as, for example, substituted piperdinyl,
(20) cyclyl-alkylene- (i.e., cycloalkyl-alkylene-, such as ($C_3$ to $C_{20}$)cycloalkyl-$C_1$ to $C_8$)alkylene-, such as, for example, ($C_3$ to $C_{10}$)cycloalkyl-$C_1$ to $C_8$)alkylene-), said cyclyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said cyclyl-alkylene- substituent include, for example, cyclohexyl-$CH_2$—,
(21) substituted (cyclyl-alkylene)- (i.e., substituted (cycloalkyl-alkylene)-, such as substituted (($C_3$ to $C_{20}$)cycloalkyl-($C_1$ to $C_8$)alkylene)-, such as, for example, substituted (($C_3$ to $C_{10}$)cycloalkyl-$C_1$ to $C_8$)alkylene)-), said cycylyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said substituted (cyclyl-alkylene)- substituent include, for example, substituted cyclohexyl-$CH_2$—,
(22) heterocyclyl-alkylene- (i.e., heterocycloalkyl-alkylene-, such as (4 to 20 membered)heterocycloalkyl-($C_1$ to $C_8$)alkylene-, such as, for example, piperidinyl-$CH_2$—),
(23) substituted heterocyclyl-alkylene- (i.e., substituted heterocycloalkyl-alkylene-, such as substituted (4 to 20 membered)heterocycloalkyl-($C_1$ to $C_8$)-alkylene-, such as, for example, substituted piperidinyl-$CH_2$—),

(24) —C(O)N($R^6$)$_2$ (e.g., —C(O)NH$_2$, —C(O)NHCH$_3$, and —C(O)N(CH$_3$)$_2$),
(25) —S(O)$_2$N($R^6$)$_2$ (e.g., —S(O)$_2$NH$_2$, —S(O)$_2$NHCH$_3$, and —S(O)$_2$N(CH$_3$)$_2$),
(26) -alkylene-C(O)N($R^6$)$_2$ (e.g., —(C$_1$ to C$_6$)alkylene-C(O)N($R^6$)$_2$, such as, for example, —CH$_2$—C(O)N(CH$_3$)$_2$),
(27) substituted -alkylene-C(O)N($R^6$)$_2$ (e.g., substituted —(C$_1$ to C$_6$)alkylene-C(O)N($R^6$)$_2$),
(28) -alkylene-S(O)$_2$N($R^6$)$_2$ (e.g., —(C$_1$ to C$_6$)alkylene-S(O)$_2$N($R^6$)$_2$, such as, for example, —CH$_2$—S(O)$_2$—NHC$_6$H$_5$ (i.e., —CH$_2$—S(O)$_2$—NH-phenyl)),
(29) substituted -alkylene-S(O)$_2$N($R^6$)$_2$ (e.g., substituted —(C$_1$ to C$_6$)-alkylene-S(O)$_2$N($R^6$)$_2$, such as, for example, substituted —CH$_2$—S(O)$_2$—NHC$_6$H$_5$ (i.e., substituted —CH$_2$—S(O)$_2$—NH-phenyl)),
(30) $R^6$C(O)N($R^6$)-alkylene- (e.g., $R^6$C(O)N($R^6$)—(C$_1$ to C$_6$)alkylene-, such as, for example, —CH$_2$—NH—C(O)—CH$_3$),
(31) substituted $R^6$C(O)N($R^6$)-alkylene- (e.g., substituted $R^6$C(O)N($R^6$)—(C$_1$ to C$_6$)alkylene-),
(32) $R^6$S(O)$_2$N($R^6$)-alkylene- (e.g., $R^6$S(O)$_2$N($R^6$)—(C$_1$ to C$_6$)alkylene-, such as, for example, —CH$_2$—NH—S(O)$_2$—CH$_3$),
(33) substituted $R^6$S(O)$_2$N($R^6$)-alkylene- (e.g., substituted $R^6$S(O)$_2$N($R^6$)—(C$_1$ to C$_6$)alkylene-),
(34) arylheterocyclenyl (arylheterocycloalkenyl) wherein the aryl moiety is fused to the heterocycloalkenyl moiety, wherein, for example said aryl moiety is phenyl and said heterocyclenyl moiety is a 3 to 6 membered ring comprising at least one (e.g., 1 to 3, or 1 to 2, or 1) heteroatom selected from the group consisting of: O, S and N, examples include, but are not limited to, indolyl,
(35) arylheterocyclyl (arylheterocycloalkyl) wherein the aryl moiety is fused to the heterocycloalkyl moiety, and wherein two hydrogens on a carbon of the heterocyclyl moiety are replaced by a single divalent moiety (such as, for example, =O), and wherein, for example, said aryl moiety is phenyl and said heterocyclyl moiety is a 3 to 6 membered ring comprising at least one (e.g., 1 to 3, or 1 to 2, or 1) heteroatom selected from the group consisting of: O, S and N, examples include, but are not limited to, oxindolyl,
(36) substituted arylheterocyclenyl (substituted arylheterocycloalkenyl) wherein the aryl moiety is fused to the heterocycloalkenyl moiety, wherein, for example said aryl moiety is phenyl and said heterocyclenyl moiety is a 3 to 6 membered ring comprising at least one (e.g., 1 to 3, or 1 to 2, or 1) heteroatom selected from the group consisting of: O, S and N, examples include, but are not limited to, substituted indole,
(37) substituted arylheterocyclyl (substituted arylheterocycloalkyl) wherein the aryl moiety is fused to the heterocycloalkyl moiety, and wherein two hydrogens on a carbon of the heterocyclyl moiety are replaced by a single divalent moiety (such as, for example, =O), and wherein, for example, said aryl moiety is phenyl and said heterocyclyl moiety is a 3 to 6 membered ring comprising at least one (e.g., 1 to 3, or 1 to 2, or 1) heteroatom selected from the group consisting of: O, S and N, examples include, but are not limited to, substituted oxindolyl,
(38) —N($R^6$)C(O)$R^6$ (such as, for example —NH—C(O)—CH$_3$),
(39) —N($R^6$)S(O)$_2$$R^6$ (such as, for example, —NH—S(O)$_2$- phenyl),
(40) —C(O)$R^6$ (such as, for example, —C(O)-phenyl),
(41) —S(O)$_2$$R^6$ (such as, for example, —S(O)$_2$CH$_3$),
(42) heteroaryl,
(43) substituted heteroaryl,
(44) heteroaryl-alkylene-, and
(45) substituted heteroaryl-alkylene-; and
wherein:
 (A) said substituted $R^4$ substituents (9), (11), (13), (15), (17), (19), (21), (23), (27), (29), (31), (33), (36), (37), (43) and (45) are substituted with 1 to 3 substituents independently selected from the group consisting of: (a) alkyl (e.g., C$_1$ to C$_6$ alkyl), (b) haloalkyl (e.g., halo(C$_1$ to C$_6$)alkyl, such as, for example, a halo(C$_1$ to C$_6$)alkyl having one or more halo moieities independently selected from the group consisting of F, Cl and Br), (c) halo (e.g., F, Cl and Br), (d) alkoxy (e.g., C$_1$ to C$_6$ alkoxy, e.g., —OCH$_3$), and (e) CN, and wherein said substituted $R^4$ substituents include, for example:
  (1) substituents wherein the alkylene moiety in the $R^4$ substituent (15) is substituted and the aryl moiety of the $R^4$ substituent (15) is unsubstituted,
  (2) substituents wherein the alkylene moiety in the $R^4$ substituent (15) is unsubstituted and the aryl moiety of the $R^4$ substituent (15) is substituted,
  (3) substituents wherein the alkylene moiety in the $R^4$ substituent (15) is substituted and the aryl moiety of the $R^4$ substituent (15) is substituted, wherein the substituents on the substituted aryl and alkylene moieties are independently selected,
  (4) substituents wherein the alkylene moiety in the $R^4$ substituent (21) is substituted and the cyclyl moiety of the $R^4$ substituent (21) is unsubstituted,
  (5) substituents wherein the alkylene moiety in the $R^4$ substituent (21) is unsubstituted and the cyclyl moiety of the $R^4$ substituent (21) is substituted,
  (6) substituents wherein the alkylene moiety in the $R^4$ substituent (21) is substituted and the cyclyl moiety of the $R^4$ substituent (21) is substituted, wherein the substituents on the substituted cyclyl and alkylene moieties are independently selected,
  (7) substituents wherein the alkylene moiety in the $R^4$ substituent (23) is substituted and the heterocyclyl moiety of the $R^4$ substituent (23) is unsubstituted,
  (8) substituents wherein the alkylene moiety in the $R^4$ substituent (23) is unsubstituted and the heterocyclyl moiety of the $R^4$ substituent (23) is substituted,
  (9) substituents wherein the alkylene moiety in the $R^4$ substituent (23) is substituted and the heterocyclyl moiety of the $R^4$ substituent (23) is substituted, wherein the substituents on the substituted cyclyl and alkylene moieties are independently selected,
  (10) substituents wherein the aryl moiety in the $R^4$ substituent (36) is substituted and the heterocyclenyl moiety of the $R^4$ substituent (36) is unsubstituted,
  (11) substituents wherein the aryl moiety in the $R^4$ substituent (36) is unsubstituted and the heterocyclenyl moiety of the $R^4$ substituent (36) is substituted,
  (12) substituents wherein the aryl moiety in the $R^4$ substituent (36) is substituted and the heterocyclenyl moiety of the $R^4$ substituent (36) is substituted, wherein the substituents on the substituted aryl and heterocyclenyl moieties are independently selected,
  (13) substituents wherein the aryl moiety in the $R^4$ substituent (37) is substituted and the heterocyclyl moiety of the $R^4$ substituent (37) is unsubstituted,

35

(14) substituents wherein the aryl moiety in the $R^4$ substituent (37) is unsubstituted and the heterocyclyl moiety of the $R^4$ substituent (37) is substituted,
(15) substituents wherein the aryl moiety in the $R^4$ substituent (37) is substituted and the heterocyclyl moiety of the $R^4$ substituent (37) is substituted, wherein the substituents on the substituted aryl and heterocyclyl moieties are independently selected,
(16) substituents wherein the alkylene moiety in the $R^4$ substituent (45) is substituted and the heteroaryl moiety of the $R^4$ substituent (45) is unsubstituted,
(17) substituents wherein the alkylene moiety in the $R^4$ substituent (45) is unsubstituted and the heteroaryl moiety of the $R^4$ substituent (45) is substituted, and
(18) substituents wherein the alkylene moiety in the $R^4$ substituent (45) is substituted and the heteroaryl moiety of the $R^4$ substituent (45) is substituted, wherein the substituents on the substituted aryl and alkylene moieties are independently selected, and
(B) said substituted alkyl $R^4$ substituent (3) is substituted with 1 to 3 substituents selected from the group consisting of: (a) alkoxy (e.g., $C_1$ to $C_6$ alkoxy, e.g., —$OCH_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieities independently selected from the group consisting of F, Cl and Br), and (d) CN;

$R^5$ is selected from the group consisting of:
(1) arylalkylene- (e.g., aryl($C_1$ to $C_6$)alkylene-, such as, for example, aryl-$CH_2$—, such as, for example, phenyl-$CH_2$— (i.e., benzyl)),
(2) substituted arylalkylene- (e.g., substituted (aryl($C_1$ to $C_6$)alkylene)-, such as, for example, substituted benzyl),
(3) arylheterocyclyl (arylheterocycloalkyl) wherein the aryl moiety is fused to the heterocycloalkyl moiety, wherein, for example said aryl moiety is phenyl and said heterocyclenyl moiety is a 3 to 6 membered ring comprising at least one (e.g., 1 to 3, or 1 to 2, or 1) heteroatom selected from the group consisting of: O, S and N, examples include, but are not limited to, indolyl,
(4) arylheterocyclenyl (arylheterocycloalkenyl) wherein the aryl moiety is fused to the heterocycloalkenyl moiety, and wherein two hydrogens on a carbon of the heterocyclyl moiety are replaced by a single divalent moiety (such as, for example, =O), and wherein, for example, said aryl moiety is phenyl and said heterocyclyl moiety is a 3 to 6 membered ring comprising at least one (e.g., 1 to 3, or 1 to 2, or 1) heteroatom selected from the group consisting of: O, S and N, examples include, but are not limited to, oxindolyl,
(5) substituted arylheterocyclenyl (substituted arylheterocycloalkenyl) wherein the aryl moiety is fused to the heterocycloalkenyl moiety, wherein, for example said aryl moiety is phenyl and said heterocyclyl moiety is a 3 to 6 membered ring comprising at least one (e.g., 1 to 3, or 1 to 2, or 1) heteroatom selected from the group consisting of: O, S and N, examples include, but are not limited to, substituted indole,
(6) substituted arylheterocyclyl (substituted arylheterocycloalkyl) wherein the aryl moiety is fused to the heterocycloalkyl moiety, and wherein two hydrogens on a carbon of the heterocyclyl moiety are replaced by a single divalent moiety (such as, for example, =O), and wherein, for example, said aryl moiety is phenyl and said heterocyclyl moiety is a 3 to 6 membered ring comprising at least one (e.g., 1 to 3, or 1 to 2, or 1) heteroatom

36 selected from the group consisting of: O, S and N, examples include, but are not limited to, substituted oxindolyl,
(7) aryl (e.g., phenyl),
(8) substituted aryl (e.g., substituted phenyl),
(9) —C(O)O$R^{26}$ (e.g., —C(O)O$CH_3$),
(10) —$R^{28}$—O—$R^{30}$ (e.g., —$CH_2$—O—$CH_2$-phenyl),
(11) alkyl (e.g., $C_1$ to $C_6$alkyl, such as, for example, $C_1$ to $C_4$ alkyl, such as, for example, —$CH_3$, i-propyl and i-butyl),
(12) substituted alkyl (e.g., substituted $C_1$ to $C_6$ alkyl),
(13) alkenyl (e.g., $C_2$ to $C_6$alkenyl, such as, for example, —$CH_2$—CH=$CH_2$),
(14) alkynyl (e.g., $C_2$ to $C_6$alkynyl, such as, for example, —$CH_2$—C≡CH),
(15) —N($R^6$)$_2$ (such as, for example, —$NH_2$) provided that when X is N then said —N($R^6$)$_2$ substituent is not bonded to a carbon atom that is adjacent to X (i.e., when X is N, said —N($R^6$)$_2$ substituent is bonded to a carbon that is at least two carbons from X's N),
(16) —O$R^6$ (such as, for example, —OH), provided that when X is N then said —O$R^6$ substituent is not bonded to a carbon atom that is adjacent to X (i.e., when X is N, said —OR substituent is bonded to a carbon that is at least two carbons from X's N),
(17) =O,
(18) N($R^6$)$_2$alkylene- (e.g., N($R^6$)$_2$($C_1$ to $C_6$)alkylene-, such as, for example, —$CH_2NH_2$, and —($CH_2$)$_2NH_2$),
(19) N($R^6$)$_2$-(substituted alkylene)- (e.g., N($R^6$)$_2$(substituted $C_1$ to $C_6$)alkylene-),
(20) $R^6$O-alkylene- (e.g., $R^6$O-($C_1$ to $C_6$)alkylene, such as, for example, —$CH_2$OH, and —($CH_2$)$_2$OH),
(21) $R^6$O-(substituted alkylene)- (e.g., $R^6$O-(substituted $C_1$ to $C_6$)alkylene),
(22) cyclyl (i.e., cycloalkyl, such as $C_3$ to $C_{20}$ cycloalkyl, and preferably $C_3$ to $C_{10}$ cycloalkyl), said cyclyl (cycloalkyl) substituent comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine,
(23) substituted cyclyl (i.e., substituted cycloalkyl, such as substituted $C_3$ to $C_{20}$ cycloalkyl, and preferably substituted $C_3$ to $C_{10}$ cycloalkyl), said substituted cyclyl (substituted cycloalkyl) substituent comprising substituted monocyclic and substituted polycyclic (e.g., substituted bicyclic) rings, said substituted monocyclic rings generally comprising a $C_3$ to $C_8$ monocyclic ring (e.g., substituted cyclohexyl), and said substituted polycyclic (e.g., substituted bicyclic) rings generally comprising a $C_6$ to $C_{10}$ bicyclic ring, examples of said substituted polycyclic rings include, for example, substituted decaline and substituted adamantine,
(24) heterocyclyl (i.e., heterocycloalkyl, such as a 3 to 10 membered ring), comprising at least one (e.g., 1 to 3, or 1 to 2, or 1) heteroatom selected from the group consisting of: O, S, and N, such as, for example, piperdinyl,
(25) substituted heterocyclyl (i.e., substituted heterocycloalkyl, such as a substituted 3 to 10 membered ring), comprising at least one (e.g., 1 to 3, or 1 to 2, or 1) heteroatom selected from the group consisting of: O, S, and N, such as, for example, substituted piperdinyl,
(26) cyclyl-alkylene- (i.e., cycloalkyl-alkylene-, such as ($C_3$ to $C_{20}$)cycloalkyl-$C_1$ to $C_8$)alkylene-, such as, for example, ($C_3$ to $C_{10}$)cycloalkyl-$C_1$ to $C_8$)alkylene-), said cyclyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said cyclyl-alkylene- substituent include, for example, cyclohexyl-$CH_2$—),

(27) substituted (cyclyl-alkylene)- (i.e., substituted (cycloalkyl-alkylene)-, such as substituted (($C_3$ to $C_{20}$)cycloalkyl-($C_1$ to $C_8$)alkylene)-, such as, for example, substituted (($C_3$ to $C_{10}$)cycloalkyl-$C_1$ to $C_8$)alkylene)-), said cycylyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said substituted (cyclyl-alkylene)- substituent include, for example, substituted cyclohexyl-$CH_2$—),

(28) heterocyclyl-alkylene- (i.e., heterocycloalkyl-alkylene-, such as (4 to 20 membered)heterocycloalkyl-($C_1$ to $C_8$)alkylene-, such as, for example, piperidinyl-$CH_2$—),

(29) substituted heterocyclyl-alkylene- (i.e., substituted heterocycloalkyl-alkylene-, such as substituted (4 to 20 membered)heterocycloalkyl-($C_1$ to $C_8$)-alkylene-, such as, for example, substituted piperidinyl-$CH_2$—),

(30) —$C(O)N(R^6)_2$ (e.g., —$C(O)NH_2$, —$C(O)NHCH_3$, and —$C(O)N(CH_3)_2$),

(31) —$S(O)_2N(R^6)_2$ (e.g., —$S(O)_2NH_2$, —$S(O)_2NHCH_3$, and —$S(O)_2N(CH_3)_2$),

(32) -alkylene-$C(O)N(R^6)_2$ (e.g., —($C_1$ to $C_6$)alkylene-$C(O)N(R^6)_2$, such as, for example, —$CH_2$—$C(O)N(CH_3)_2$),

(33) substituted -alkylene-$C(O)N(R^6)_2$ (e.g., substituted —($C_1$ to $C_6$)alkylene-$C(O)N(R^1)_2$),

(34) -alkylene-$S(O)_2N(R^6)_2$ (e.g., —($C_1$ to $C_6$)alkylene-$S(O)_2N(R^6)_2$, such as, for example, —$CH_2$—$S(O)_2$—$NHC_6H_5$ (i.e., —$CH_2$—$S(O)_2$—NH-phenyl)),

(35) substituted -alkylene-$S(O)_2N(R^6)_2$ (e.g., substituted -($C_1$ to $C_6$)-alkylene-$S(O)_2N(R^6)_2$, such as, for example, substituted —$CH_2$—$S(O)_2$—$NHC_6H_5$ (i.e., substituted —$CH_2$—$S(O)_2$—NH-phenyl)),

(36) $R^6C(O)N(R^6)$-alkylene- (e.g., $R^6C(O)N(R^6)$—($C_1$ to $C_6$)alkylene-, such as, for example, —$CH_2$—NH—$C(O)$—$CH_3$),

(37) substituted $R^6C(O)N(R^6)$-alkylene- (e.g., substituted $R^6C(O)N(R^6)$—($C_1$ to $C_6$)alkylene-),

(38) $R^6S(O)_2N(R^6)$-alkylene- (e.g., $R^6S(O)_2N(R^6)$—($C_1$ to $C_6$)alkylene-, such as, for example, —$CH_2$—NH—$S(O)_2$—$CH_3$),

(39) substituted $R^6S(O)_2N(R^6)$-alkylene- (e.g., substituted $R^6S(O)_2N(R^6)$—($C_1$ to $C_6$)alkylene-),

(40) —$N(R^6)C(O)R^6$ (such as, for example —NH—$C(O)$—$CH_3$),

(41) —$N(R^6)S(O)_2R^6$ (such as, for example, —NH—$S(O)_2$-phenyl),

(42) —$C(O)R^6$ (such as, for example, —$C(O)$-phenyl), and

(43) —$S(O)_2R^6$ (such as, for example, —$S(O)_2CH_3$); and wherein:

(A) said substituted $R^4$ substituents (2), (5), (6), (8), (19), (21), (23), (25), (27), (29), (33), (35), (37), and (39) are substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieties independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN and wherein said substituted $R^4$ substituents include, for example:

(1) substituents wherein the alkylene moiety in the $R^4$ substituent
(2) is substituted and the aryl moiety of the $R^4$ substituent (2) is unsubstituted,
(2) substituents wherein the alkylene moiety in the $R^4$ substituent (2) is unsubstituted and the aryl moiety of the $R^4$ substituent (2) is substituted,
(3) substituents wherein the alkylene moiety in the $R^4$ substituent (2) is substituted and the aryl moiety of the $R^4$ substituent (2) is substituted, wherein the substituents on the substituted aryl and alkylene moieties are independently selected,
(4) substituents wherein the aryl moiety in the $R^4$ substituent (5) is substituted and the heterocyclenyl moiety of the $R^4$ substituent (5) is unsubstituted,
(5) substituents wherein the aryl moiety in the $R^4$ substituent (5) is unsubstituted and the heterocyclenyl moiety of the $R^4$ substituent (5) is substituted,
(6) substituents wherein the aryl moiety in the $R^4$ substituent (5) is substituted and the heterocyclenyl moiety of the $R^4$ substituent (5) is substituted, wherein the substituents on the substituted aryl and heterocyclenyl moieties are independently selected,
(7) substituents wherein the aryl moiety in the $R^4$ substituent (6) is substituted and the heterocyclyl moiety of the $R^4$ substituent (6) is unsubstituted,
(8) substituents wherein the aryl moiety in the $R^4$ substituent (6) is unsubstituted and the heterocyclyl moiety of the $R^4$ substituent (6) is substituted, and
(9) substituents wherein the aryl moiety in the $R^4$ substituent (6) is substituted and the heterocyclyl moiety of the $R^4$ substituent (6) is substituted, wherein the substituents on the substituted aryl and heterocyclyl moieties are independently selected,
(10) substituents wherein the alkylene moiety in the $R^4$ substituent (27) is substituted and the cyclyl moiety of the $R^4$ substituent (27) is unsubstituted,
(11) substituents wherein the alkylene moiety in the $R^4$ substituent (27) is unsubstituted and the cyclyl moiety of the $R^4$ substituent (27) is substituted,
(12) substituents wherein the alkylene moiety in the $R^4$ substituent (27) is substituted and the cyclyl moiety of the $R^4$ substituent (27) is substituted, wherein the substituents on the substituted cyclyl and alkylene moieties are independently selected,
(13) substituents wherein the alkylene moiety in the $R^4$ substituent (29) is substituted and the heterocyclyl moiety of the $R^4$ substituent (29) is unsubstituted,
(14) substituents wherein the alkylene moiety in the $R^4$ substituent (29) is unsubstituted and the heterocyclyl moiety of the $R^4$ substituent (29) is substituted, and
(15) substituents wherein the alkylene moiety in the $R^4$ substituent (29) is substituted and the heterocyclyl moiety of the $R^4$ substituent (29) is substituted, wherein the substituents on the substituted cyclyl and alkylene moieties are independently selected, and (B) said substituted alkyl $R^4$ substituent (12) is substituted with 1 to 3 substituents selected from the group consisting of: (a) alkoxy (e.g., $C_1$ to $C_6$ alkoxy, e.g., —$OCH_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieities independently selected from the group consisting of F, Cl and Br), and (d) CN;

Each $R^6$ is independently selected from the group consisting of:

(1) H, provided that R is not H when $R^6$ is bonded to a S atom, (2) alkyl (e.g., $C_1$ to $C_6$alkyl, such as, for example, $C_1$ to $C_4$ alkyl, such as, for example, —$CH_3$), (3) substituted alkyl (e.g., substituted $C_1$ to $C_6$ alkyl), (4) cyclyl (i.e., cycloalkyl, such as $C_3$ to $C_{20}$ cycloalkyl, and preferably $C_3$ to $C_{10}$ cycloalkyl), said cyclyl (cycloalkyl) substituent comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, (5) substituted cyclyl (i.e., substituted cycloalkyl, such as substituted $C_3$ to $C_{20}$ cycloalkyl, and preferably substituted $C_3$ to $C_{10}$ cycloalkyl), said substituted cycylyl (substituted cycloalkyl) substituent comprising substituted monocyclic and substituted polycyclic (e.g., substituted bicyclic) rings, said substituted monocyclic rings generally comprising a $C_3$ to $C_8$ monocyclic ring (e.g., substituted cyclohexyl), and said substituted polycyclic (e.g., substituted bicyclic) rings generally comprising a $C_6$ to $C_{10}$ bicyclic ring, examples of said substituted polycyclic rings include, for example, substituted decaline and substituted adamantine, (6) aryl (e.g., phenyl), (7) substituted aryl (e.g., substituted phenyl), (8) heteroaryl, (9) substituted heteroaryl,

(10) heterocyclyl (i.e., heterocycloalkyl, such as a 3 to 10 membered ring), comprising at least one (e.g., 1 to 3, or 1 to 2, or 1) heteroatom selected from the group consisting of: O, S, and N, such as, for example, piperdinyl),

(11) substituted heterocyclyl (i.e., substituted heterocyloalkyl, such as a substituted 3 to 10 membered ring), comprising at least one (e.g., 1 to 3, or 1 to 2, or 1) heteroatom selected from the group consisting of: O, S, and N, such as, for example, substituted piperdinyl),

(12) cyclyl-alkylene- (i.e., cycloalkyl-alkylene-, such as ($C_3$ to $C_{20}$)cycloalkyl-$C_1$ to $C_8$)alkylene-, such as, for example, ($C_3$ to $C_{10}$)cycloalkyl-$C_1$ to $C_8$)alkylene-), said cyclyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said cyclyl-alkylene- substituent include, for example, cyclohexyl-$CH_2$—),

(13) substituted (cyclyl-alkylene)- (i.e., substituted (cycloalkyl-alkylene)-, such as substituted (($C_3$ to $C_{20}$)cycloalkyl-($C_1$ to $C_8$)alkylene)-, such as, for example, substituted (($C_3$ to $C_{10}$)cycloalkyl-$C_1$ to $C_8$)alkylene)-), said cycylyl (cycloalkyl) moiety comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, examples of said substituted (cyclyl-alkylene)- substituent include, for example, substituted cyclohexyl-$CH_2$—),

(14) arylalkylene- (e.g., aryl($C_1$ to $C_6$)alkylene-, such as, for example, aryl-$CH_2$—, such as, for example, phenyl-$CH_2$— (i.e., benzyl)),

(15) substituted arylalkylene- (e.g., substituted aryl($C_1$ to $C_6$)alkylene-, such as, for example, substituted benzyl),

(16) heteroarylalkylene- (e.g., heteroaryl($C_1$ to $C_6$)alkylene-),

(17) substituted heteroarylalkylene- (e.g., substituted heteroaryl($C_1$ to $C_6$)alkylene-),

(18) heterocyclyl-alkylene- (i.e., heterocycloalkyl-alkylene-, such as (4 to 20 membered)heterocycloalkyl-($C_1$ to $C_8$)alkylene-, such as, for example, piperidinyl-$CH_2$—), and

(19) substituted heterocyclyl-alkylene- (i.e., substituted heterocycloalkyl-alkylene-, such as substituted (4 to 20 membered)heterocycloalkyl-($C_1$ to $C_8$)-alkylene-, such as, for example, substituted piperidinyl-$CH_2$—), and wherein:

(A) said substituted $R^6$ substituents (5), (7), (9), (11), (13), (15), (17), and (19) are substituted with 1 to 3 substituents independently selected from the group consisting of: (a) alkyl, (b) haloalkyl, (c) alkenyl, (d) alkynyl, (e) aryl, (f) heteroaryl, (g) aralkyl, (h) alkylaryl, (i) heteroaralkyl, (j) heteroarylalkenyl, (k) heteroarylalkynyl, (l) alkylheteroaryl, (m) hydroxy, (n) hydroxyalkyl, (o) alkoxy, (p) aryloxy, (q) aralkoxy, (r) acyl, (s) aroyl, (t) halo, (u) nitro, (v) cyano, (w) carboxy, (x) alkoxycarbonyl, (y) aryloxycarbonyl, (z) aralkoxycarbonyl, (aa) alkylsulfonyl, (ab) arylsulfonyl, (ac) heteroaryl-sulfonyl, (ad) alkylthio, (ae) arylthio, (af) heteroarylthio, (ag) aralkylthio, (ah) heteroaralkylthio, (ai) cycloalkyl, (aj) heterocyclyl, (ak) —C(=N—CN)—$NH_2$, (al) —C(=NH)—$NH_2$, (am) —C(=NH)—NH(alkyl), (an) $Y_1Y_2$N—, (ao) $Y_1Y_2$N-alkyl-, (ap) $Y_1Y_2$NC(O)—, (aq) $Y_1Y_2$$NSO_2$—, (ar) —$SO_2NY_1Y_2$, (as) a moiety that simultaneously replaces one H on each of two adjacent carbon atoms (e.g., methylene dioxy, ethylene dioxy, —C($CH_3$)$_2$—), and (at) a moiety that forms a four to seven-membered cycloalkyl, cycloalkenyl, heterocyclyl, aryl or heteroaryl ring when: (i) taken together with two adjacent carbon atoms (i.e., a fused ring is formed), or (ii) taken together with a carbon atom and an adjacent heteroatom (i.e., a fused ring is formed), or (iii) taken together with a single carbon atom (i.e., a spiro ring is formed), and wherein $Y_1$ and $Y_2$ are the same or different and are independently selected from the group consisting of hydrogen, alkyl, aryl, cycloalkyl, and aralkyl; and preferably said substituted $R^6$ substituents (5), (7), (9), (11), (13), (15), (17), and (19) are substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieities independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN and wherein said substituted $R^6$ substituents include, for example:

(1) substituents wherein the alkylene moiety in the $R^6$ substituent (13) is substituted and the cyclyl moiety of the $R^6$ substituent (13) is unsubstituted,
(2) substituents wherein the alkylene moiety in the $R^6$ substituent (13) is unsubstituted and the cyclyl moiety of the $R^6$ substituent (13) is substituted,
(3) substituents wherein the alkylene moiety in the $R^6$ substituent (13) is substituted and the cyclyl moiety of the $R^6$ substituent (13) is substituted, wherein the substituents on the substituted cyclyl and alkylene moieties are independently selected,
(4) substituents wherein the aryl moiety in the $R^6$ substituent (15) is substituted and the alkylene moiety of the $R^6$ substituent (15) is unsubstituted,
(5) substituents wherein the aryl moiety in the $R^6$ substituent (15) is unsubstituted and the alkylene moiety of the $R^6$ substituent (15) is substituted,
(6) substituents wherein the aryl moiety in the $R^6$ substituent (15) is substituted and the alkylene moiety of the $R^6$ substituent (15) is substituted, wherein the substituents on the substituted aryl and heterocyclenyl moieties are independently selected,
(7) substituents wherein the heteroaryl moiety in the $R^6$ substituent (17) is substituted and the alkylene moiety of the $R^6$ substituent (17) is unsubstituted,
(8) substituents wherein the heteroaryl moiety in the $R^6$ substituent (17) is unsubstituted and the alkylene moiety of the $R^6$ substituent (17) is substituted, and
(9) substituents wherein the heteroaryl moiety in the $R^6$ substituent (17) is substituted and the alkylene moiety of the $R^6$ substituent (17) is substituted, wherein the substituents on the substituted aryl and heterocyclyl moieties are independently selected,
(10) substituents wherein the alkylene moiety in the $R^6$ substituent (19) is substituted and the heterocyclyl moiety of the $R^6$ substituent (19) is unsubstituted,
(11) substituents wherein the alkylene moiety in the $R^6$ substituent (19) is unsubstituted and the heterocyclyl moiety of the $R^6$ substituent (19) is substituted, and
(12) substituents wherein the alkylene moiety in the $R^6$ substituent (19) is substituted and the heterocyclyl moiety of the $R^6$ substituent (19) is substituted, wherein the substituents on the substituted cyclyl and alkylene moieties are independently selected, and
(B) said substituted alkyl $R^6$ substituent (12) is substituted with 1 to 3 substituents independently selected from the group consisting of: (a) haloalkyl, (b) alkenyl, (c) alkynyl, (d) aryl, (e) heteroaryl, (f) aralkyl, (g) alkylaryl, (h) heteroaralkyl, (i) heteroarylalkenyl, (j) heteroarylalkynyl, (k) alkylheteroaryl, (l) hydroxy, (m) hydroxyalkyl, (n) alkoxy, (o) aryloxy, (p) aralkoxy, (q) acyl, (r) aroyl, (s) halo, (t) nitro, (u) cyano, (v) carboxy, (w) alkoxycarbonyl, (x) aryloxycarbonyl, (y) aralkoxycarbonyl, (z) alkylsulfonyl, (aa) arylsulfonyl, (ab) heteroarylsulfonyl, (ac) alkylthio, (ad) arylthio, (ae) heteroarylthio, (af) aralkylthio, (ag) heteroaralkylthio, (ah) cycloalkyl, (ai) heterocyclyl, (aj) —C(=N—CN)—NH$_2$, (ak) —C(=NH)—NH$_2$, (al) —C(=NH)—NH(alkyl), (am) $Y_1Y_2N$—, (an) $Y_1Y_2N$-alkyl-, (ao) $Y_1Y_2NC(O)$—, (ap) $Y_1Y_2NSO_2$—, (aq) —SO$_2NY_1Y_2$, (ar) a moiety that simultaneously replaces one H on each of two adjacent carbon atoms (e.g., methylene dioxy, ethylene dioxy, —C(CH$_3$)$_2$—), and (as) a moiety that forms a four to seven-membered cycloalkyl, cycloalkenyl, heterocyclyl, aryl or heteroaryl ring when: (i) taken together with two adjacent carbon atoms (i.e., a fused ring is formed), or (ii) taken together with a carbon atom and an adjacent heteroatom (i.e., a fused ring is formed), or (iii) taken together with a single carbon atom (i.e., a spiro ring is formed), and wherein $Y_1$ and $Y_2$ are the same or different and are independently selected from the group consisting of hydrogen, alkyl, aryl, cycloalkyl, and aralkyl; and preferably said substituted alkyl $R^6$ substituent is substituted with 1 to 3 substituents independently selected from the group consisting of: (a) alkoxy (e.g., $C_1$ to $C_6$ alkoxy, e.g., —OCH$_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieties independently selected from the group consisting of F, Cl and Br), and (d) CN;

$R^{20}$ and $R^{22}$ are each independently selected from the group consisting of:
(1) H,
(2) alkyl (e.g., $C_1$ to $C_6$alkyl, such as, for example, $C_1$ to $C_4$ alkyl, such as, for example, —CH$_3$),
(3) substituted alkyl (e.g., substituted $C_1$ to $C_6$ alkyl),
(4) arylalkylene- (e.g., aryl($C_1$ to $C_6$)alkylene-, such as, for example, aryl-CH$_2$—, such as, for example, phenyl-CH$_2$— (i.e., benzyl), and —CH$_2$-naphthyl),
(5) substituted arylalkylene- (e.g., substituted aryl($C_1$ to $C_6$)alkylene-, such as, for example, substituted benzyl, and substituted and —CH$_2$-naphthyl),
(6) heteroarylalkylene (e.g., heteroaryl($C_1$ to $C_6$)alkylene-, such as, for example, —CH$_2$-pyridyl, such as, —CH$_2$-p-pyridyl, and also, for example, —CH$_2$-quinolinyl),
(7) substituted heteroarylalkylene (e.g., substituted heteroaryl($C_1$ to $C_6$)alkylene- such as, for example, substituted —CH$_2$-pyridyl, such as, substituted —CH$_2$-p-pyridyl, and also, for example, substituted —CH$_2$-quinolinyl),
(8) aryl (e.g., phenyl),
(9) substituted aryl (e.g., substituted phenyl),
(10) heteroaryl,
(11) substituted heteroaryl,
(12) —S(O)$_2$-aryl (e.g., —S(O)$_2$-phenyl),
(13) substituted —S(O)$_2$-aryl (e.g., substituted —S(O)$_2$-phenyl),
(14) —S(O)$_2$-alkyl (e.g., —S(O)$_2$—CH$_3$),
(15) —S(O)$_2$-alkyl (e.g., substituted —S(O)$_2$—CH$_3$),
(16) —C(O)-aryl (e.g., —C(O)-phenyl),
(17) substituted —C(O)-aryl (e.g., substituted —C(O)-phenyl),
(18) —C(O)-alkyl (e.g., —C(O)—CH$_3$),
(19) substituted —C(O)-alkyl (e.g., substituted —C(O)—CH$_3$),
(20) —C(O)-alkylene-aryl (e.g., —C(O)—CH$_2$-phenyl),
(21) substituted —C(O)-alkylene-aryl (e.g., substituted —C(O)—CH$_2$-phenyl),
(22) -alkylene-O-alkyl (e.g., —(CH$_2$)$_2$—O—CH$_3$), and
(23) substituted -alkylene-O-alkyl (e.g., —(CH$_2$)$_2$—O—CH$_3$), and
wherein:
(A) said substituted $R^{20}$ and/or $R^{22}$ substituents (5), (7), (9), (11), (13), (17), (21) are independently substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieties independently selected from the group consisting of F, Cl and Br, such as, for example, —$CF_3$), (c) halo (e.g., F, Cl and Br), (d) alkoxy (e.g., $C_1$ to $C_6$ alkoxy, e.g., —$OCH_3$), (e) CN, and (f) aryl (e.g., phenyl), and wherein said substituted $R^{20}$ and/or $R^{22}$ substituents include, for example:
  (1) substituents wherein the alkylene moiety in the $R^{20}$ and/or $R^{22}$ substituent (5) is substituted and the aryl moiety of the $R^{20}$ and/or $R^{22}$ substituent (5) is unsubstituted,
  (2) substituents wherein the alkylene moiety in the $R^{20}$ and/or $R^{22}$ substituent (5) is unsubstituted and the aryl moiety of the $R^{20}$ and/or $R^{22}$ substituent (5) is substituted,
  (3) substituents wherein the alkylene moiety in the $R^{20}$ and/or $R^{22}$ substituent (5) is substituted and the aryl moiety of the $R^{20}$ and/or $R^{22}$ substituent (5) is substituted, wherein the substituents on the substituted aryl and alkylene moieties are independently selected,
  (4) substituents wherein the heteroaryl moiety in the $R^{20}$ and/or $R^{22}$ substituent (7) is substituted and the alkylene moiety of the $R^{20}$ and/or $R^{22}$ substituent (7) is unsubstituted,
  (5) substituents wherein the heteroaryl moiety in the $R^{20}$ and/or $R^{22}$ substituent (7) is unsubstituted and the alkylene moiety of the $R^{20}$ and/or $R^{22}$ substituent (7) is substituted, and
  (6) substituents wherein the heteroaryl moiety in the $R^{20}$ and/or $R^{22}$ substituent (7) is substituted and the alkylene moiety of the $R^{20}$ and/or $R^{22}$ substituent (7) is substituted, wherein the substituents on the substituted heteroaryl and alkylene moieties are independently selected,
  (7) substituents wherein the aryl moiety in the $R^{20}$ and/or $R^{22}$ substituent (21) is substituted and the alkylene moiety of the $R^{20}$ and/or $R^{22}$ substituent (21) is unsubstituted,
  (8) substituents wherein the aryl moiety in the $R^{20}$ and/or $R^{22}$ substituent (21) is unsubstituted and the alkylene moiety of the $R^{20}$ and/or $R^{22}$ substituent (21) is substituted, and
  (9) substituents wherein the aryl moiety in the $R^{20}$ and/or $R^{22}$ substituent (21) is substituted and the alkylene moiety of the $R^{20}$ and/or $R^{22}$ substituent (21) is substituted, wherein the substituents on the substituted aryl and alkylene moieties are independently selected,
  (10) substituents wherein in the $R^{20}$ and/or $R^{22}$ substituent (23), the alkylene moiety is substituted, or the alkyl moiety is substituted, or both the alkylene and the alkyl moiety are substituted, and
(B) said substituted alkyl moiety in the $R^{20}$ and/or $R^{22}$ (3), (15), (19) substituents are independently substituted with 1 to 3 substituents independently selected from the group consisting of: (a) alkoxy (e.g., $C_1$ to $C_6$ alkoxy, e.g., —$OCH_3$), (b) halo (e.g., F, Cl and Br), (c) haloalkyl (e.g., halo($C_1$ to $C_6$)alkyl, such as, for example, a halo($C_1$ to $C_6$)alkyl having one or more halo moieties independently selected from the group consisting of F, Cl and Br, such as, for example, —$CF_3$), (d) CN, and (e) aryl (e.g., phenyl);
$R^{26}$ is selected from the group consisting of:
(1) H,
(2) aryl (e.g., phenyl),
(3) substituted aryl (e.g., substituted phenyl),
(4) heteroaryl,
(5) substituted heteroaryl,
(6) cyclyl (i.e., cycloalkyl, such as $C_3$ to $C_{20}$ cycloalkyl, and preferably $C_3$ to $C_{10}$ cycloalkyl), said cyclyl (cycloalkyl) substituent comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine,
(7) substituted cyclyl (i.e., substituted cycloalkyl, such as substituted $C_3$ to $C_{20}$ cycloalkyl, and preferably substituted $C_3$ to $C_{10}$ cycloalkyl), said substituted cycylyl (substituted cycloalkyl) substituent comprising substituted monocyclic and substituted polycyclic (e.g., substituted bicyclic) rings, said substituted monocyclic rings generally comprising a $C_3$ to $C_8$ monocyclic ring (e.g., substituted cyclohexyl), and said substituted polycyclic (e.g., substituted bicyclic) rings generally comprising a $C_6$ to $C_{10}$ bicyclic ring, examples of said substituted polycyclic rings include, for example, substituted decaline and substituted adamantine,
(8) arylalkylene- (e.g., aryl($C_1$ to $C_6$)alkylene-, such as, for example, aryl-$CH_2$—, such as, for example, phenyl-$CH_2$— (i.e., benzyl)),
(9) substituted arylalkylene- (e.g., substituted aryl($C_1$ to $C_6$)alkylene-, such as, for example, substituted benzyl),
(10) heteroarylalkylene- (e.g., heteroaryl($C_1$ to $C_6$)alkylene-),
(11) substituted heteroarylalkylene- (e.g., substituted heteroaryl($C_1$ to $C_6$)alkylene-),
(12) heterocyclyl (i.e., heterocycloalkyl, such as a 3 to 10 membered ring), comprising at least one (e.g., 1 to 3, or 1 to 2, or 1) heteroatom selected from the group consisting of: O, S, and N, such as, for example, piperdinyl,
(13) substituted heterocyclyl (i.e., substituted heterocycloalkyl, such as a substituted 3 to 10 membered ring), comprising at least one (e.g., 1 to 3, or 1 to 2, or 1) heteroatom selected from the group consisting of: O, S, and N, such as, for example, substituted piperdinyl,
(14) heterocyclyl-alkylene- (i.e., heterocycloalkyl-alkylene-, such as (4 to 20 membered)heterocycloalkyl-($C_1$ to $C_8$)alkylene-, such as, for example, piperidinyl-$CH_2$—),
(15) substituted heterocyclyl-alkylene- (i.e., substituted heterocycloalkyl-alkylene-, such as substituted (4 to 20 membered)heterocycloalkyl-($C_1$ to $C_8$)-alkylene-, such as, for example, substituted piperidinyl-$CH_2$—),
(16) alkyl (e.g., $C_1$ to $C_6$ alkyl), and
(17) substituted alkyl (e.g., substituted $C_1$ to $C_6$ alkyl), and wherein:
  (A) said substituted $R^{26}$ substituents (3), (5), (7), (9), (11), (13), and (15) are substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieties independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN and wherein said substituted $R^{26}$ substituents include, for example:
    (1) substituents wherein the alkylene moiety in the $R^{26}$ substituent (9) is substituted and the aryl moiety of the $R^{26}$ substituent (9) is unsubstituted, (2) substituents wherein the alkylene moiety in the $R^{26}$ substituent (9) is unsubstituted and the aryl moiety of the $R^{26}$ substituent (9) is substituted, (3) substituents wherein the alkylene moiety in the $R^{26}$ substituent (9) is substituted and the aryl moiety of the $R^{26}$ substituent (9) is substituted, wherein the substituents on the substituted aryl and alkylene moieties are independently selected, (4) substituents wherein the heteroaryl moiety in the $R^{26}$ substituent (11) is substituted and the alkylene moiety of the $R^{26}$ substituent (11) is unsubstituted, (5) substituents wherein the heteroaryl moiety in the $R^{26}$ substituent (11) is unsubstituted and the alkylene moiety of the $R^{26}$ substituent (11) is substituted, (6) substituents wherein the heteroaryl moiety in the $R^{26}$ substituent (11) is substituted and the alkylene moiety of the $R^{26}$ substituent (11) is substituted, wherein the substituents on the substituted aryl and heterocyclenyl moieties are independently selected, (7) substituents wherein the alkylene moiety in the $R^{26}$ substituent (15) is substituted and the heterocyclyl moiety of the $R^{26}$ substituent (15) is unsubstituted, (8) substituents wherein the alkylene moiety in the $R^{26}$ substituent (15) is unsubstituted and the heterocyclyl moiety of the $R^{26}$ substituent (15) is substituted, and (9) substituents wherein the alkylene moiety in the $R^{26}$ substituent (15) is substituted and the heterocyclyl moiety of the $R^{26}$ substituent (15) is substituted, wherein the substituents on the substituted aryl and heterocyclyl moieties are independently selected, and (B) said substituted alkyl $R^{26}$ substituent (17) is substituted with 1 to 3 substituents independently selected from the group consisting of: (a) haloalkyl (e.g., halo ($C_1$ to $C_6$)alkyl, such as, for example, a halo($C_1$ to $C_6$)alkyl having one or more halo moieities independently selected from the group consisting of F, Cl and Br), (b) halo (e.g., F, Cl and Br), (c) alkoxy (e.g., $C_1$ to $C_6$ alkoxy, e.g., —$OCH_3$), and (d) CN;

$R^{28}$ is selected from the group consisting of:

(1) alkylene (such as $C_1$ to $C_8$ alkylene, or $C_1$ to $C_2$ alkylene); and (2) substituted alkylene (such as substituted $C_1$ to $C_8$ alkylene, or substituted $C_1$ to $C_2$ alkylene); and wherein said substituted alkylene is substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieities independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN; or $R^{28}$ is absent (e.g., when $R^{28}$ is absent the moiety —$R^{28}$—O—$R^{30}$ becomes the moiety —O—$R^{30}$); and $R^{30}$ is selected from the group consisting of:

(1) H, (2) aryl (e.g., phenyl), (3) substituted aryl (e.g., substituted phenyl), (4) heteroaryl, (5) substituted heteroaryl, (6) cyclyl (i.e., cycloalkyl, such as $C_3$ to $C_{20}$ cycloalkyl, and preferably $C_3$ to $C_{10}$ cycloalkyl), said cyclyl (cycloalkyl) substituent comprising monocyclic and polycyclic (e.g., bicyclic) rings, said monocyclic rings generally comprising a $C_3$ to $C_8$ monocyclic ring (e.g., cyclohexyl), and said polycyclic (e.g., bicyclic) rings generally comprising a $C_6$ to $C_{10}$ bicyclic ring, examples of said polycyclic rings include, for example, decaline and adamantine, (7) substituted cyclyl (i.e., substituted cycloalkyl, such as substituted $C_3$ to $C_{20}$ cycloalkyl, and preferably substituted $C_3$ to $C_{10}$ cycloalkyl), said substituted cycylyl (substituted cycloalkyl) substituent comprising substituted monocyclic and substituted polycyclic (e.g., substituted bicyclic) rings, said substituted monocyclic rings generally comprising a $C_3$ to $C_8$ monocyclic ring (e.g., substituted cyclohexyl), and said substituted polycyclic (e.g., substituted bicyclic) rings generally comprising a $C_6$ to $C_{10}$ bicyclic ring, examples of said substituted polycyclic rings include, for example, substituted decaline and substituted adamantine, (8) arylalkylene- (e.g., aryl($C_1$ to $C_6$)alkylene-, such as, for example, aryl-$CH_2$—, such as, for example, phenyl-$CH_2$— (i.e., benzyl)), (9) substituted arylalkylene- (e.g., substituted aryl($C_1$ to $C_6$)alkylene-, such as, for example, substituted benzyl),

(10) heteroarylalkylene- (e.g., heteroaryl($C_1$ to $C_6$)alkylene-),

(11) substituted heteroarylalkylene- (e.g., substituted heteroaryl($C_1$ to $C_6$)alkylene-),

(12) heterocyclyl (i.e., heterocycloalkyl, such as a 3 to 10 membered ring), comprising at least one (e.g., 1 to 3, or 1 to 2, or 1) heteroatom selected from the group consisting of: O, S, and N, such as, for example, piperdinyl,

(13) substituted heterocyclyl (i.e., substituted heterocycloalkyl, such as a substituted 3 to 10 membered ring), comprising at least one (e.g., 1 to 3, or 1 to 2, or 1) heteroatom selected from the group consisting of: O, S, and N, such as, for example, substituted piperdinyl,

(14) heterocyclyl-alkylene- (i.e., heterocycloalkyl-alkylene-, such as (4 to 20 membered)heterocycloalkyl-($C_1$ to $C_8$)alkylene-, such as, for example, piperidinyl-$CH_2$—),

(15) substituted heterocyclyl-alkylene- (i.e., substituted heterocycloalkyl-alkylene-, such as substituted (4 to 20 membered)heterocycloalkyl-($C_1$ to $C_8$)-alkylene-, such as, for example, substituted piperidinyl-$CH_2$—),

(16) alkyl (e.g., $C_1$ to $C_6$ alkyl), and

(17) substituted alkyl (e.g., substituted $C_1$ to $C_6$ alkyl), and wherein:

(A) said substituted $R^{30}$ substituents (3), (5), (7), (9), (11), (13), and (15) are substituted with 1 to 3 substituents independently selected from the group consisting of: (a) alkyl (e.g., $C_1$ to $C_6$ alkyl), (b) haloalkyl (e.g., halo($C_1$ to $C_6$)alkyl, such as, for example, a halo($C_1$ to $C_6$)alkyl having one or more halo moieities independently selected from the group consisting of F, Cl and Br), (c) halo (e.g., F, Cl and Br), (d) alkoxy (e.g., $C_1$ to $C_6$ alkoxy, e.g., —$OCH_3$), and (e) CN and wherein said substituted $R^{30}$ substituents include, for example:

(1) substituents wherein the alkylene moiety in the $R^{30}$ substituent (9) is substituted and the aryl moiety of the $R^{30}$ substituent (9) is unsubstituted, (2) substituents wherein the alkylene moiety in the $R^{30}$ substituent (9) is unsubstituted and the aryl moiety of the $R^{30}$ substituent (9) is substituted, (3) substituents wherein the alkylene moiety in the R³⁰ substituent (9) is substituted and the aryl moiety of the R³⁰ substituent (9) is substituted, wherein the substituents on the substituted aryl and alkylene moieties are independently selected,
(4) substituents wherein the heteroaryl moiety in the R³⁰ substituent (11) is substituted and the alkylene moiety of the R³⁰ substituent (11) is unsubstituted,
(5) substituents wherein the heteroaryl moiety in the R³⁰ substituent (11) is unsubstituted and the alkylene moiety of the R³⁰ substituent (11) is substituted,
(6) substituents wherein the heteroaryl moiety in the R³⁰ substituent (11) is substituted and the alkylene moiety of the R³⁰ substituent (11) is substituted, wherein the substituents on the substituted aryl and heterocyclenyl moieties are independently selected,
(7) substituents wherein the alkylene moiety in the R³⁰ substituent (15) is substituted and the heterocyclyl moiety of the R³⁰ substituent (15) is unsubstituted,
(8) substituents wherein the alkylene moiety in the R³⁰ substituent (15) is unsubstituted and the heterocyclyl moiety of the R³⁰ substituent (15) is substituted, and
(9) substituents wherein the alkylene moiety in the R³⁰ substituent (15) is substituted and the heterocyclyl moiety of the R³⁰ substituent (15) is substituted, wherein the substituents on the substituted aryl and heterocyclyl moieties are independently selected, and
(B) said substituted alkyl R³⁰ substituent (17) is substituted with 1 to 3 substituents independently selected from the group consisting of: (a) haloalkyl (e.g., halo($C_1$ to $C_6$)alkyl, such as, for example, a halo($C_1$ to $C_6$)alkyl having one or more halo moieties independently selected from the group consisting of F, Cl and Br), (b) halo (e.g., F, Cl and Br), (c) alkoxy (e.g., $C_1$ to $C_6$ alkoxy, e.g., —OCH₃), and (d) CN.

Examples of the cyclic moiety:

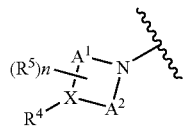

include, for example,

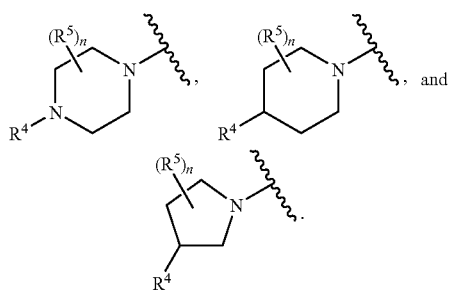

Preferably, the cyclic moiety:

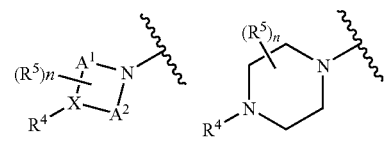

wherein R⁴, R⁵ and n are as described herein for the compounds of formula 1.0 and the embodiments and the examples thereof.

Those skilled in the art will appreciate that the cyclic moiety:

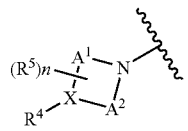

includes the moiety:

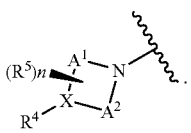

Those skilled in the art will also appreciate that the cyclic moiety:

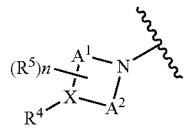

includes the moiety:

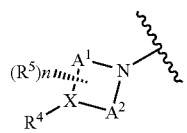

Thus, examples of the cyclic moiety described above, include:

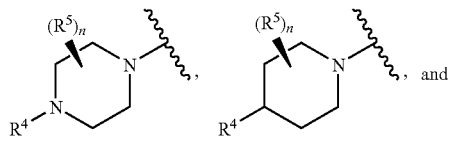

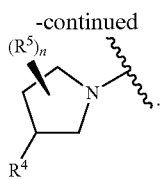

Examples of the cyclic moiety described above also include:

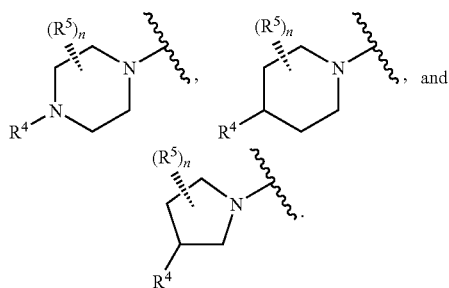

Thus, the preferred cyclic moiety:

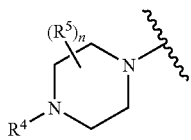

includes:

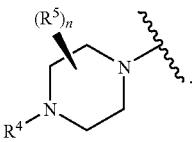

The preferred cyclic moiety also includes:

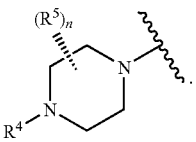

The cyclic moiety:

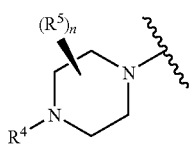

is preferred.

Examples of $R^1$ include, but are not limited to: H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Thus, examples of $R^1$ include, for example, H, $NH_2$, —$NH(CH_2C_6H_5)$ (i.e., —NH—$CH_2$-phenyl), —$NHCH_3$, and —$NH(CH_3)_2$.

Preferably $R^1$ is selected from the group consisting of: H, —$NH_2$ and —NH—$CH_2$-phenyl.

Preferably, $R^2$ is absent, i.e., preferably, m is 0.

Preferably, $R^3$ is alkyl, more preferably $C_1$ to $C_2$alkyl, and most preferably methyl.

Preferably $R^4$ is H.

Preferably X is N.

Preferably $A^1$ is a two carbon chain and $A^2$ is a two carbon chain.

Preferably, n is 1 and $R^5$ is selected from the group consisting of: (1) aralkyl- (e.g., aryl($C_1$ to $C_6$)alkyl-, such as, for example, aryl-$CH_2$—, such as, for example, phenyl-$CH_2$— (i.e., benzyl)), (2) heteroarylalkyl (e.g., aryl($C_1$ to $C_6$)alkyl-, such as, for example, heteroaryl-$CH_2$—, such as, for example, —$CH_2$-indolyl, (for example, wherein the —$CH_2$— moiety is bonded to the 3-position of the 1H-indolyl ring), (3) aryl (e.g., phenyl), (4) —$C(O)OR^{26}$ (e.g., —$C(O)OCH_3$), (5) —$R^{28}$—O—$R^{30}$ (e.g., —$CH_2$—O—$CH_2$-phenyl), (6) alkyl (e.g., $C_1$ to $C_6$alkyl, such as, for example, $C_1$ to $C_4$ alkyl, such as, for example, i-propyl and i-butyl).

Examples of preferred $R^5$ groups, wherein n is 1, are: benzyl, phenyl, —$C(O)OCH_3$, —$CH_2$—O—$CH_2$-phenyl, i-propyl, i-butyl and —$CH_2$indolyl (such as, for example,

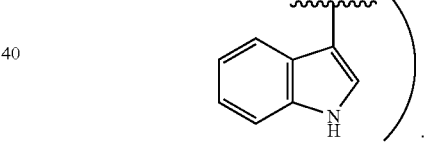

A more preferred $R^5$ group, wherein n is 1, is benzyl (i.e., —$CH_2$-phenyl).

In one embodiment of this invention $R^1$ is H and $R^5$, wherein n is 1, is —$CH_2$-phenyl.

In another embodiment of this invention $R^1$ is H and $R^5$, wherein n is 1, is i-butyl.

In another embodiment of this invention $R^1$ is —NH($CH_2$phenyl) and $R^5$, wherein n is 1, is i-propyl.

In another embodiment of this invention $R^1$ is —$NH_2$ and $R^5$, wherein n is 1, is i-propyl.

Preferably, $A^1$ represents a two carbon chain, and $A^2$ represents a two carbon chain (i.e., a 6 membered ring is formed by -$A^1$-X-$A^2$-being bonded to the N).

Preferably, X is N.

Preferably, X is N, and $A^1$ represents a two carbon chain, and $A^2$ represents a two carbon chain (i.e., a piperazine ring is formed by -$A^1$-X-$A^2$-being bonded to the N).

In another embodiment of this invention, for the compounds of formula 1.0, $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. The remaining substituents are as defined for formula 1.0. In this embodiment, $R^1$ is preferably selected from the group consisting of: H, —$NH_2$, and —NH—$CH_2$phenyl.

In another embodiment of this invention, for the compounds of formula 1.0, $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), and (2) $R^3$ is selected from the group consisting of: halo and alkyl (e.g., $C_1$ to $C_6$ alkyl, preferably $C_1$ to $C_2$ alkyl, and more preferably methyl).

In another embodiment of this invention, for the compounds of formula 1.0, $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), (2) $R^3$ is selected from the group consisting of: halo and alkyl (e.g., $C_1$ to $C_6$ alkyl, preferably $C_1$ to $C_2$ alkyl, and more preferably methyl), and (3) $A^1$ is a two carbon chain and $A^2$ is a two carbon chain.

In another embodiment of this invention, for the compounds of formula 1.0, $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), (2) $R^3$ is selected from the group consisting of: halo and alkyl (e.g., $C_1$ to $C_6$ alkyl, preferably $C_1$ to $C_2$ alkyl, and more preferably methyl), (3) $A^1$ is a two carbon chain and $A^2$ is a two carbon chain, and (4) X is N.

In another embodiment of this invention, for the compounds of formula 1.0, $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., ($C_1$ to $C_6$)$_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), (2) $R^3$ is selected from the group consisting of: halo and alkyl (e.g., $C_1$ to $C_6$ alkyl, preferably $C_1$ to $C_2$ alkyl, and more preferably methyl), (3) $A^1$ is a two carbon chain and $A^2$ is a two carbon chain, (4) X is N, (5) n is 1, and (6) $R^5$ is selected from the group consisting of: (a) aralkyl- (e.g., aryl($C_1$ to $C_6$)alkyl-, such as, for example, aryl-$CH_2$—, such as, for example, phenyl-$CH_2$— (i.e., benzyl)), (b) heteroarylalkyl (e.g., aryl($C_1$ to $C_6$)alkyl-, such as, for example, heteroaryl-$CH_2$—, such as, for example, —$CH_2$-indolyl, (for example, wherein the —$CH_2$— moiety is bonded to the 3-position of the 1H-indolyl ring), (c) aryl (e.g., phenyl), (d) —$C(O)OR^{26}$ (e.g., —$C(O)OCH_3$), (e) —$R^{28}$—O—$R^{30}$ (e.g., —$CH_2$—O—$CH_2$-phenyl), (f) alkyl (e.g., $C_1$ to $C_6$alkyl, such as, for example, $C_1$ to $C_4$ alkyl, such as, for example, i-propyl and i-butyl). In this embodiment, $R^5$ is preferably benzyl, phenyl, —$C(O)OCH_3$, —$CH_2$—O—$CH_2$-phenyl, i-propyl, i-butyl and —$CH_2$indolyl (such as, for example,

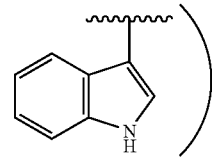

Also, in this embodiment, a preferred $R^5$ group is benzyl (i.e., —$CH_2$-phenyl). This embodiment includes compounds wherein: $R^1$ is H and $R^5$ is —$CH_2$-phenyl. This embodiment also includes compounds wherein $R^1$ is H and $R^5$ is i-butyl. This embodiment also includes compounds wherein $R^1$ is —$NH(CH_2phenyl)$ and $R^5$ is i-propyl. This embodiment also includes compounds wherein $R^1$ is —$NH_2$ and $R^5$ is i-propyl.

Another embodiment of the compounds of formula 1.0 is directed to the compounds of formula 1.1:

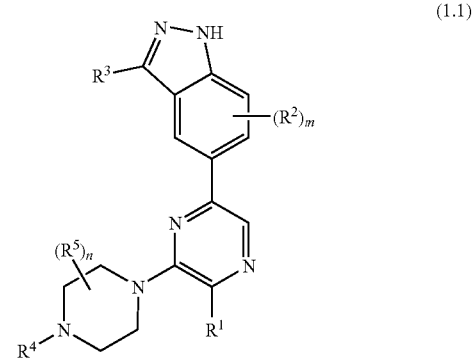

(1.1)

or the pharmaceutically acceptable salts thereof; wherein $R^1$, $R^2$, $R^3$, $R^4$, $R^5$, m and n are as defined for the compounds of formula 1.0 and the embodiments, and the examples thereof.

Thus, another embodiment of this invention is directed to the compounds of formula 1.1 wherein: $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., $(C_1$ to $C_6)_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. The remaining substituents are as defined for formula 1.0. In this embodiment, $R^1$ is preferably selected from the group consisting of: H, —$NH_2$, and —NH—$CH_2$phenyl.

Another embodiment of this invention is directed to the compounds of formula 1.1 wherein: $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., $(C_1$ to $C6)_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), and (2) $R^3$ is selected from the group consisting of: halo and alkyl (e.g., $C_1$ to $C_6$ alkyl, preferably $C_1$ to $C_2$ alkyl, and more preferably methyl).

Another embodiment of this invention is directed to the compounds of formula 1.1 wherein: $R^1$ is selected from the group consisting of: H, H, alkylamino- (e.g., $C_1$ to $C_6$alkyl-NH—, i.e., in the $R^1$ moiety —$NR^{20}R^{22}$, $R^{20}$ is H and $R^{22}$ is an alkyl group (e.g., a $C_1$ to $C_6$alkyl group)), and dialkylamino- wherein each alkyl moiety is independently selected (e.g., $(C_1$ to $C_6)_2$alkyl-NH—, wherein each alkyl is independently selected, i.e., in the $R^1$ moiety —$NR^{20}R^{22}$, $R^{20}$ and $R^{22}$ are independently selected an alkyl groups (e.g., independently selected $C_1$ to $C_6$alkyl groups)). Examples of $R^1$ include, for example, H, $NH_2$, —$NH(CH_2C_6H_5)$ (i.e., —NH—$CH_2$-phenyl), —$NHCH_3$, and —$NH(CH_3)_2$. In this embodiment, $R^1$ is preferably selected from the group consisting of: H, —$NH_2$, and —NH—$CH_2$phenyl. Also, in this embodiment: (1) $R^2$ is absent (i.e. m is 0), (2) $R^3$ is selected from the group consisting of: halo and alkyl (e.g., $C_1$ to $C_6$ alkyl, preferably $C_1$ to $C_2$ alkyl, and more preferably methyl), (3) n is 1, and (4) $R^5$ is selected from the group consisting of: (a) aralkyl- (e.g., aryl($C_1$ to $C_6$)alkyl-, such as, for example, aryl-$CH_2$—, such as, for example, phenyl-$CH_2$— (i.e., benzyl)), (b) heteroarylalkyl (e.g., aryl($C_1$ to $C_6$)alkyl-, such as, for example, heteroaryl-$CH_2$—, such as, for example, —$CH_2$-indolyl, (for example, wherein the —$CH_2$— moiety is bonded to the 3-position of the 1H-indolyl ring), (c) aryl (e.g., phenyl), (d) —$C(O)OR^{26}$ (e.g., —$C(O)OCH_3$), (e) —$R^{28}$—O—$R^{30}$ (e.g., —$CH_2$—O—$CH_2$-phenyl), (f) alkyl (e.g., $C_1$ to $C_6$alkyl, such as, for example, $C_1$ to $C_4$ alkyl, such as, for example, i-propyl and i-butyl). In this embodiment, $R^5$ is preferably benzyl, phenyl, —$C(O)OCH_3$, —$CH_2$—O—$CH_2$-phenyl, i-propyl, i-butyl and —$CH_2$indolyl (such as, for example,

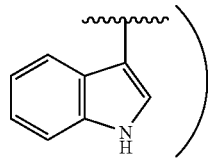

.

Also, in this embodiment, a preferred $R^5$ group is benzyl (i.e., —$CH_2$-phenyl). This embodiment includes compounds wherein: $R^1$ is H and $R^5$ is —$CH_2$-phenyl. This embodiment also includes compounds wherein $R^1$ is H and $R^5$ is i-butyl. This embodiment also includes compounds wherein $R^1$ is —$NH(CH_2$phenyl) and $R^5$ is i-propyl. This embodiment also includes compounds wherein $R^1$ is —$NH_2$ and $R^5$ is i-propyl.

The compounds of Formula 1.0 are preferably purified to a degree suitable for use as a pharmaceutically active substance. That is, the compounds of Formula 1.0 can have a purity of 95 wt % or more (excluding adjuvants such as pharmaceutically acceptable carriers, solvents, etc., which are used in formulating the compound of Formula 1.0 into a conventional form, such as a pill, capsule, IV solution, etc. suitable for administration into a patient). More preferably, the purity can be 97 wt % or more, even more preferably, 99 wt % or more. A purified compound of Formula 1.0 includes a single isomer having a purity, as discussed above, of 95 wt % or more, 97 wt % or more, or 99 wt % or more, as discussed above. For example, the purified compound of Formula 1.0 can include a compound of Structure A (above) having a purity of 95 wt % or more, 97 wt % or more, or 99 wt % or more.

Alternatively, the purified compound of Formula 1.0 can include a mixture of isomers, each having a structure according to Formula 1.0, where the amount of impurity (i.e., compounds or other contaminants, exclusive of adjuvants as discussed above) is 5 wt % or less, 3 wt % or less, or 1 wt % or less. For example, the purified compound of Formula 1.0 can be an isomeric mixture of compounds of formula 1.0 where the ratio of the amounts of the two isomers is approximately 1:1, and the combined amount of the two isomers is 95 wt % or more, 97 wt % or more, or 99 wt % or more.

The compounds of formula 1.0, or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of formula 1.0, or pharmaceutically acceptable salts, solvates, or esters thereof, can be administered orally or parenterally, including intravenous, intramuscular, interperitoneal, subcutaneous, rectal, or topical routes of administration.

Pharmaceutical compositions comprising at least one compound of formula 1.0, or a pharmaceutically acceptable salt, solvate, or ester thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of formula 1.0, or a pharmaceutically acceptable salt, solvate, or ester thereof, administered to a patient can be determined by a physician based on the age, weight, and response of the patient, as well as by the severity of the condition treated. For example, the amount of compound of formula 1.0, or a pharmaceutically acceptable salt, solvate, or ester thereof, administered to the patient can range from about 0.1 mg/kg body weight per day to about 60 mg/kg/d, preferably about 0.5 mg/kg/d to about 40 mg/kg/d.

The compounds of formula 1.0, or pharmaceutically acceptable salts, solvates, or esters thereof, can also be administered in combination with other therapeutic agents. For example one or more compounds of formula 1.0, or pharmaceutically acceptable salts, solvates, or esters thereof, can be administered with one or more additional active ingredients selected from the group consisting of a second kinase inhibitor, an estrogen receptor modulator, an androgen receptor modulator, a retinoid receptor modulator, a cyctotoxic agent, a prenyl-protein transferase inhibitor, an HMG-CoA reductase inhibitor, an HIV protease inhibitor, a reverse transcriptase inhibitor, an angiogenesis inhibitor, an inhibitor of inherent multidrug resistance, an anti-emetic agent, an agent useful in the treatment of anemia, an agent useful in the treatment of neutropenia, and an immunologic-enhancing drug. Examples of such additional active ingredients may be found in *Cancer Principles and Practice of Oncology*, V. T. Devita and S. Hellman (Eds.), $6^{th}$ Ed. (Feb. 15, 2001), Lippincott Williams & Wilkins, Publ.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include but are not limited to finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include but are not limited to bexarotene, tretinoin, 13-cis-retinoic acid, 9-cis-retinoic acid, α-difluoromethylornithine, ILX23-7553,trans-N-(4'-hydroxyphenyl) retinamide, and N-4-carboxyphenylretinamide.

"Cytotoxic/cytostatic agents" refer to compounds which cause cell death or inhibit cell proliferation primarily by interfering directly with the cell's functioning or inhibit or interfere with cell myosis, including but not limited to alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors. Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro (2-methyl-pyridine) platinum, benzylguanine, glufosfamide, GPX100, (trans,trans,trans)-bis-mu-(hexane-1,6-diamine)-mu-[diamine-platinum(H)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Antiproliferative agents" include but are not limited to antisense RNA and DNA oligonucleotides such as G3139, ODN698, RVASKRAS, GEM231, and INX3001, and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine,N-[5-(2,3-dihydro-benzofuryl)sulfonyl]-N'-(3,4-dichlorophenyl) urea,N6-[4-deoxy-4-[N2-[2(E),4(E)-tetradecadienoyl] glycylamino]-L-glycero-B-L-manno-heptopyranosyl] adenine, aplidine, ecteinascidin, troxacitabine, 4-[2-amino-4-oxo-4, 6,7,8-tetrahydro-3H-pyrimidino[5,4-b][1,4] thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabinofuranosyl cytosine, 3-aminopyridine-2-carboxaldehydethiosemicarbazone and trastuzumab.

"Prenyl-protein transferase inhibitor" refers to a compound which inhibits any one or any combination of the prenyl-protein transferase enzymes, including but not limited to farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (+)-6-[amino(4-chlorophenyl)(1-methyl-IH-imidazol-5-yl)methyl]-4-(3-chlorophenyl)-I-methyl-2(1H )-quinolinone, (–)-6-[amino(4-chlorophenyl)(1-methyl-(IH)-imidazol-5-yl)methyl]-4-(3-chlorophenyl)-1-methyl-2(1H)-quinolinone, (+)-6-[amino(4-chlorophenyl) (1-methyl-IH-imidazol-5-yl)methyl]-4-(3-chlorophenyl)-I-methyl-2(IH)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-IH-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-15-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin-6,10-metheno-22H-benzo[d]imidazo[4,3-k][1,6,9,12] oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and ( )-19,20-dihydro-3-methyl-19-oxo-5H,18, 21-ethano-12,14-etheno-6,10-metheno-22H-benzo[d] imidazo[4,3-k][1,6,9,12]oxa-triazacyclooctadecine-9-carbonitrile. Other examples of prenyl-protein transferase inhibitors can be found in the following publications and patents: WO 96/30343, WO 97/18813, WO 97/21701, WO 97/23478, WO97/38665, WO98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO95/25086, WO96/05529, WO 96/06138, WO 96/06193, WO 96/16443, WO96/21701, WO 96/21456, WO96/22278, WO 96/24611, WO 96/24612, WO 96/05168, WO 96/05169, WO 96/00736, U.S. Pat. No. 5,571,792, WO 96/17861, WO96/33159, WO96/34850, WO 96/34851, WO 96/30017, WO 96/30018, WO 96/30362, WO 96/30363, WO 96/31111, WO 96/31477, WO 96/31478, WO 96/31501, WO 97/00252, WO97/03047, WO97/03050, WO97/04785, WO97/02920, WO97/17070, WO97/23478, WO97/26246, WO97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-COA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-COA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention. In HMG-CoA reductase inhibitors where an open-acid form can exist, salt and ester forms may preferably be formed from the open-acid and all such forms are included within the meaning of the term "HMG-CoA reductase inhibitor".

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-I/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475(1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105: 141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186). Other therapeutic agents that modulate or inhibit angiogenesis and may also be used in combination with the compounds of the instant invention include agents that modulate or inhibit the coagulation and fibrinolysis systems (see review in Clin. Chem. La. Med. 38: 679-692 (2000)). Examples of such agents that modulate or inhibit the coagulation and fibrinolysis pathways include, but are not limited to, heparin (see Thromb. Haemost. 80:10-23 (1998)), low molecular weight heparin and carboxypeptidase U inhibitors (also known as inhibitors of active thrombin activatable fibrinolysis inhibitor [TAFIa]) (see Thrombosis Res. 101: 329-354 (2001)). TAFIa inhibitors have been described in U.S. Ser. No. 60/310,927 (filed Aug. 8, 2001) and 60/349,925 (filed Jan. 18, 2002).

An "inhibitor of inherent multidrug resistance" (MDR), in particular MDR associated with high levels of expression of transporter proteins. Can include, for example, inhibitors of p-glycoprotein (P-gp), such as LY335979, XR9576, OC144-093, R101922, VX853 and PSC833 (valspodar).

"Anti-emetic agents" may include, for example, neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an anti-dopaminergic, such as the phenothiazines (for example prochlorperazine, fluphenazine, thioridazine and mesoridazine), metoclopramide or dronabinol.

"Anemia treatment agents" include, for example, a continuous erythropoiesis receptor activator (such as epoetin alfa).

An "agent useful in the treatment of neutropenia" can include, for example, a hematopoietic growth factor which regulates the production and function of neutrophils such as a human granulocyte colony stimulating factor, (G-CSF). Examples of a G-CSF include filgrastim.

An "immunologic-enhancing drug" can include, for example, levamisole, isoprinosine and Zadaxin.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough. Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

The compounds of the invention can be made according to the processes described below. The Compounds of this invention are also exemplified in the examples below, which examples should not be construed as limiting the scope of the disclosure. Alternative mechanistic pathways and analogous structures within the scope of the invention may be apparent to those skilled in the art.

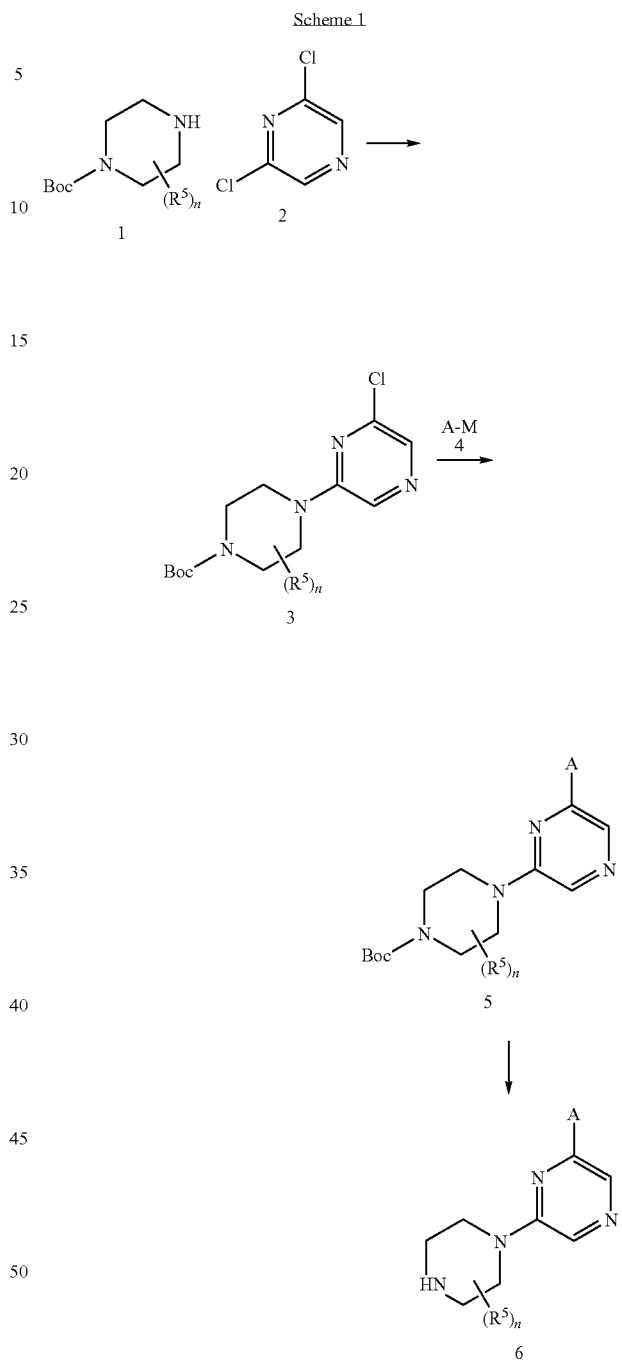

Compounds of formula 1 can be converted to compounds of formula 3 by treatment with 2,5-dichloropyrazine 2 in the presence of a base, such as diisopropylethylamine. Compounds of formula 3 can be converted to compounds of formula 5 by treatment with compounds of formula 4 (A is indazolyl; M is selected from $B(OH)_2$, B(pinacolyl), $SnMe_3$ and $SnBu_3$) in the presence of a palladium catalyst, such as $Pd(dppf)Cl_2$, $Pd(PPh_3)_4$ and $Pd(dba)3/P(o-Tol)_3$, and additive, such as potassium carbonate and triethylamine. Compounds of formula 5 can be converted to compounds of formula 6 by treatment with trifluoroacetic acid.

Scheme 2

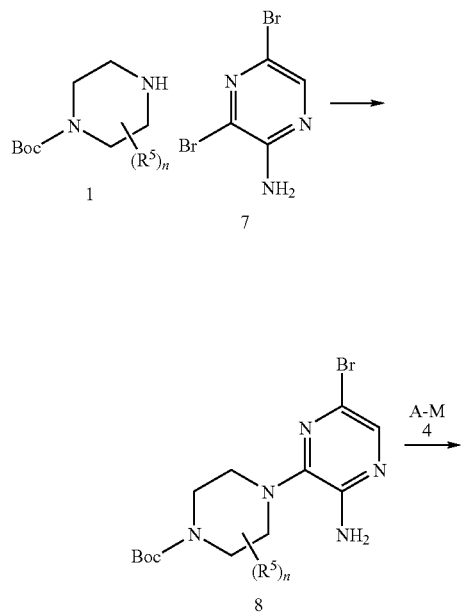

Scheme 3

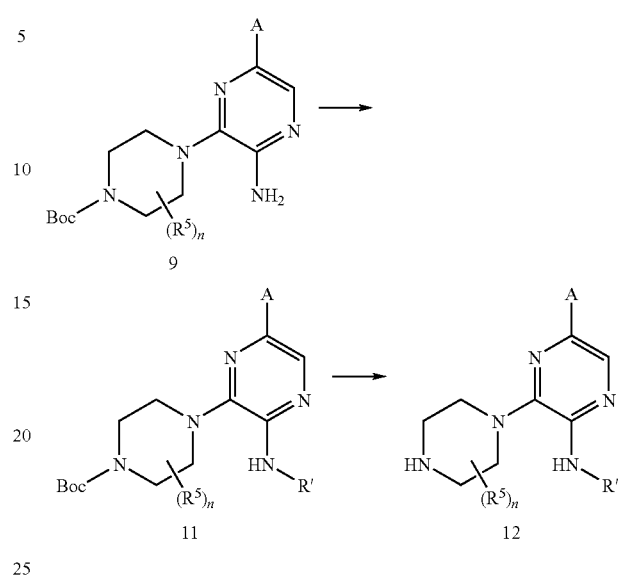

Compounds of formula 9 can be converted to compounds of formula 11 by treatment with R'—Br in the presence of a base, such as LiHMDS. Compounds of formula 11 can be converted to compounds of formula 12 by treatment with trifluoroacetic acid. In Scheme 3, R' is selected from the group consisting of: alkyl, (carbocyclyl)alkyl (i.e., cycloalkyl), (aryl)alkyl (i.e., arylalky-), (heterocyclyl)alkyl (i.e., heterocycloalkyl) and (heteroaryl)alkyl (i.e., heteroarylalkyl-).

Scheme 4

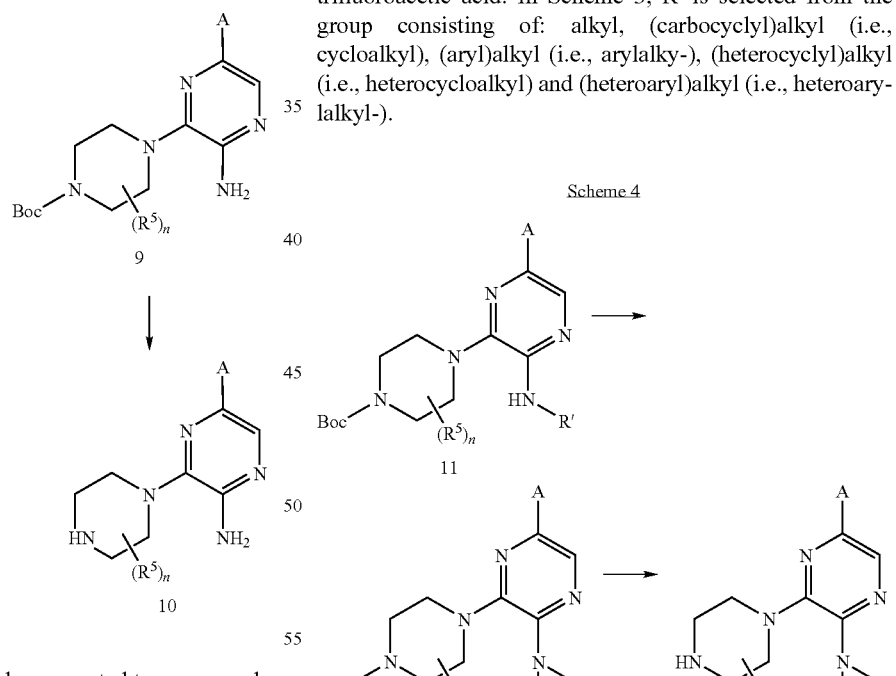

Compounds of formula 1 can be converted to compounds of formula 8 by treatment with 2-amino-3,5-dibromopyrazine 7 in the presence of a base, such as diisopropylethylamine. Compounds of formula 8 can be converted to compounds of formula 9 by treatment with compounds of formula 4 (A is indazolyl; M is selected from $B(OH)_2$, B(pinacolyl), $SnMe_3$ and $SnBu_3$) in the presence of a palladium catalyst, such as $Pd(dppf)Cl_2$, $Pd(PPh_3)_4$ and $Pd_2(dba)_3/P(o\text{-}Tol)_3$, and additive, such as potassium carbonate and triethylamine. Compounds of formula 9 can be converted to compounds of formula 10 by treatment with trifluoroacetic acid.

Compounds of formula 11 can be converted to compounds of formula 13 by treatment with R"—Br in the presence of a base, such as LiHMDS. Compounds of formula 13 can be converted to compounds of formula 14 by treatment with trifluoroacetic acid. In Scheme 4, R" is selected from the group consisting of: alkyl, (carbocyclyl)alkyl (i.e., cycloalkyl), (aryl)alkyl (i.e., arylalky-), (heterocyclyl)alkyl (i.e., heterocycloalkyl) and (heteroaryl)alkyl (i.e., heteroarylalkyl-).

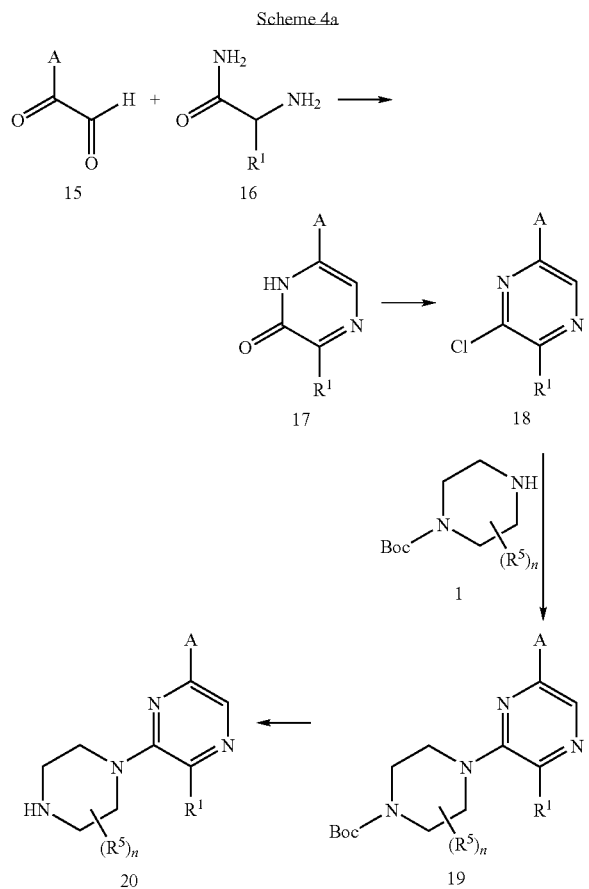

Compounds of formula 15 can be converted to compounds of formula 17 by treatment with compounds of formula 16 (for examples see *Heterocycles* (1990), 31(9), 1647-1653 and *J. Chem. Soc.* (1956), 2131-2135). Compounds of formula 17 can be converted to compounds of formula 18 by the treatment with phosphorus oxychloride. Compounds of formula 18 can be converted to compounds of formula 19 by the treatment with compounds of formula 1 in the presence of a base, such as diisopropylethylamine. Compounds of formula 19 can be converted to compounds of formula 20 by the treatment with trifluoroacetic acid.

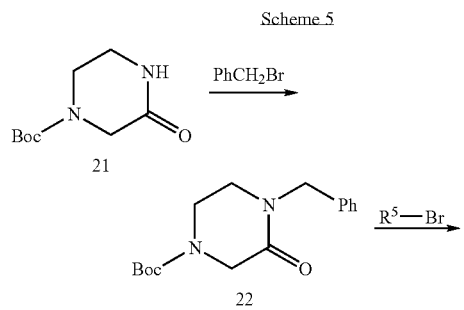

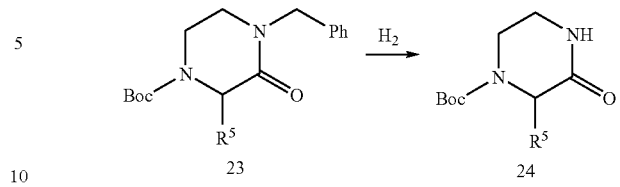

Compound of formula 21 can be converted to compound of formula 22 by treatment with benzyl bromide in the presence of sodium hydride. Compound of formula 22 can be converted to compounds of formula 23 by treatment with $R^5$—Br in the presence of a base such as LDA. Compounds of formula 23 can be converted to compounds of formula 24 by hydrogenation in the presence of Pd/C catalyst. In Scheme 5, $R^5$ is selected from the group consisting of: alkyl, (carbocyclyl)alkyl (i.e., cycloalkyl), (aryl)alkyl (i.e., arylalky-), (heterocyclyl)alkyl (i.e., heterocycloalkyl) and (heteroaryl)alkyl (i.e., heteroarylalkyl-).

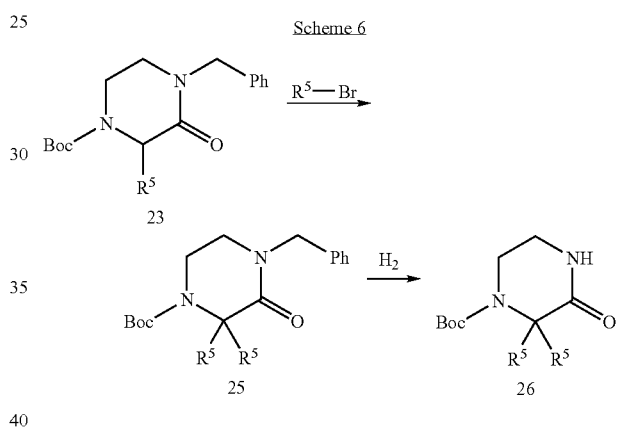

Compounds of formula 23 can be converted to compounds of formula 25 by treatment with $R^5$—Br (R' is selected from alkyl, (carbocylyl)alkyl, (aryl)alkyl, (heterocyclyl)alkyl and (heteroaryl)alkyl group) in the presence of a base such as LDA. Compounds of formula 25 can be converted to compounds of formula 26 by hydrogenation in the presence of Pd/C catalyst. Scheme 6, $R^5$ of the $R^5$—Br moiety is selected from the group consisting of: alkyl, (carbocyclyl)alkyl (i.e., cycloalkyl), (aryl)alkyl (i.e., arylalky-), (heterocyclyl)alkyl (i.e., heterocycloalkyl) and (heteroaryl)alkyl (i.e., heteroarylalkyl-).

Preparative Example 1

Preparation of 5-bromo-3-methyl-1H-indazole 104

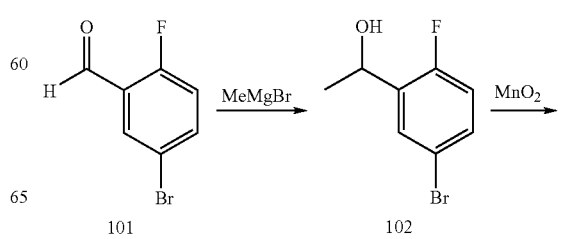

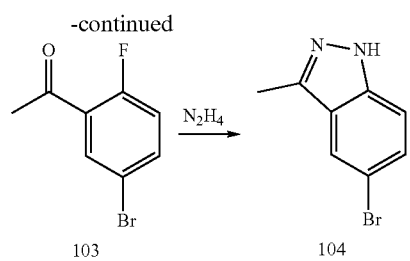

Step A

To a solution of 5-bromo-2-fluorobenzaldehyde 101 (100 g, 0.492 mol) in ether (500 mL), cooled in an ice bath, was added a 3 M solution of methyl magnesium bromide in ether (173 mL, 0.516 mol) in a dropwise manner. The reaction mixture was stirred for 30 minutes in the ice bath. The reaction mixture was allowed to warm to room temperature and was stirred for 15 minutes. The reaction mixture was cooled in an ice bath and the reaction was quenched by addition of water in a dropwise manner. The reaction mixture was acidified with dilute hydrochloric acid. The organic layer was separated. The aqueous layer was extracted with ether for two times. The combined organic layer was dried over magnesium sulfate and evaporated under reduced pressure to afford 1-(5-Bromo-2-fluoro-phenyl)-ethanol 102 (106 g, 0.484 mol) which was used in the next step without further purification.

Step B

To a solution of 1-(5-Bromo-2-fluoro-phenyl)-ethanol 102 (105 g, 0.479 mol) in dioxane (2 L) was added manganese dioxide (203 g, 2.35 mol). The reaction mixture was heated under reflux for 5 hours. The reaction mixture was allowed to cool to room temperature. The reaction mixture was filtered through Celite and the solid was washed with ether (1 L). The combined filtrate was evaporated under reduced pressure to afford the 1-(5-Bromo-2-fluoro-phenyl)-ethanone 103 (95.7 g, 0.441 mol) which was used in the next step without further purification.

Step C

To 1-(5-Bromo-2-fluoro-phenyl)-ethanone 103 (95.7 g, 0.441 mol) was added anhydrous hydrazine (240 mL, 7.65 mol). The reaction mixture was heated under reflux for 10 hours. The reaction mixture was allowed to cool to room temperature and was stirred for 16 hours. The reaction mixture was added to ice (1.4 L). The reaction mixture was stirred for 30 minutes. The reaction mixture was filtered and the white solid product was washed with water. The white solid was dried in a vacuum oven to afford the desired 5-bromo-3-methyl-1H-indazole 104 (86.1 g, 0.408 mol) which was used without further purification.

Preparative Example 2
Preparation of 3-methyl-5-trimethylstannanyl-1H-indazole 105

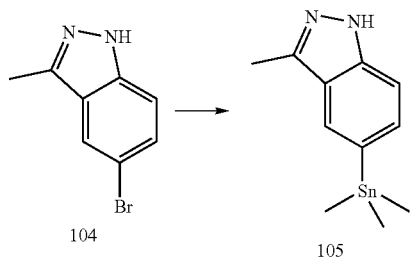

To a solution of 5-bromo-3-methyl-1H-indazole 104 (20 g, 0.095 mol) in anhydrous toluene (200 mL) was added tetrakis(triphenylphosphine)palladium (11 g, 0.0095 mol) and hex- amethylditin (36 g, 0.11 mol). The reaction mixture was heated at 95° C. for 6 hours. The organic solvent was evaporated under reduced pressure. Ethyl acetate (300 mL) was added and filtered. The filtrate was washed with sodium bicarbonate solution, water and brine. The organic layer was dried over magnesium sulfate. The organic solvent was evaporated under reduced pressure. The crude product was purified by flash column chromatography to yield the desired 3-methyl-5-trimethylstannanyl-1H-indazole 105 (17.7 g, 0.06 mol).

Example 1
Step A: Amination of Halopyrazine
Preparation of 2-amino-5-bromo-3-[(S)-4-Boc-3-benzylpiperazinyl]pyrazine 108

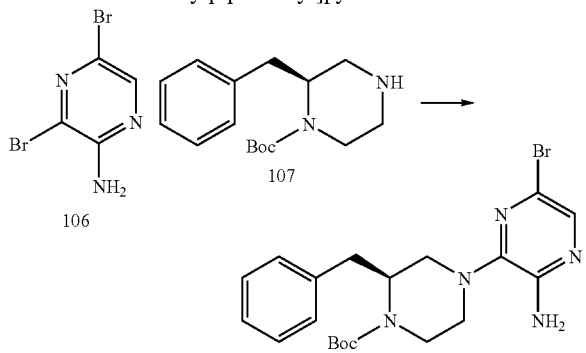

To a solution of 2-amino-3,5-dibromopyrazine 106 (0.2 g, 0.79 mmol.) and (S)-1-Boc-2-benzylpiperazine 107 (0.44 g, 1.59 mmol) in dioxane (2 mL) and trifluoromethylbenzene (2 mL) was added diisopropylethylamine (0.31 g, 2.4 mmol). The reaction mixture was heated in a microwave reactor at 210° C. for 20 minutes. Ethyl acetate (100 mL) was added. The organic layer was washed with water and brine. The organic layer was dried over sodium sulfate. The organic solvent was evaporated under reduced pressure. The crude product was purified by RP-HPLC to yield the desired 2-amino-5-bromo-3-[(S)-4-Boc-3-benzylpiperazinyl]pyrazine 108 (0.24 g, 0.536 mmol).

Step B: Stille Coupling Reaction of Halopyrazine

Preparation of 2-amino-3-[(S)-4-Boc-3-benzylpiperazinyl]-5-(3-methyl-1H-indazol-5-yl)pyrazine 109

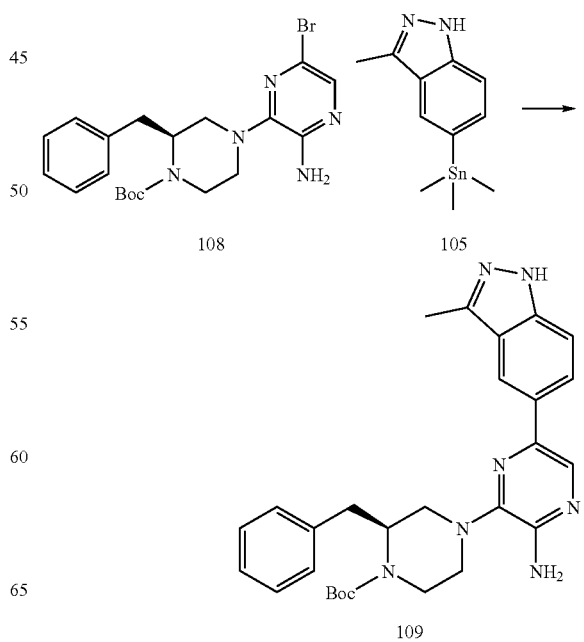

To a solution of -amino-5-bromo-3-[(S)-4-Boc-3-benzylpiperazinyl]pyrazine 108 (100 mg, 0.223 mmol) and 3-methyl-5-trimethylstannanyl-1H-indazole 105 (66 mg, 0.223 mmol.) in DMF (3.5 mL) was added tris(dibenzylideneacetone)bipalladium (10 mg, 0.011 mmol), tri-o-tolylphosphine (7 mg, 0.023 mmol) and triethylamine (23 mg, 0.23 mmol). The reaction mixture was heated in a microwave reactor at 120° C. for 10 minutes. Ethyl acetate (100 mL) was added. The organic layer was washed with water and brine. The organic layer was dried over sodium sulfate and filtered through Celite. The organic solvent was evaporated under reduced pressure. The crude product was purified by RP-HPLC to yield the desired 2-amino-3-[(S)-4-Boc-3-benzylpiperazinyl]-5-(3-methyl-1H-indazol-5-yl)pyrazine 109 (79 mg, 0.158 mmol).

Step C: Removal of the Boc Protecting Group

Preparation of 2-amino-3-[(S)-3-benzylpiperazinyl]-5-(3-methyl-1H-indazol-5-yl)pyrazine 110

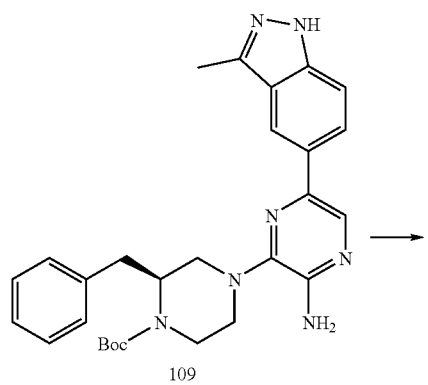

To a solution of 2-amino-3-[(S)-4-Boc-3-benzylpiperazinyl]-5-(3-methyl-1H-indazol-5-yl)pyrazine 109 (20 mg, 0.04 mmol) in dichloromethane (2 mL) was added a 4 M solution of HCl in dioxane (2 mL). The reaction mixture was stirred at room temperature for 1 hour. The organic solvent was evaporated under reduced pressure. The crude product was purified by RP-HPLC to yield the desired 2-amino-3-[(S)-3-benzylpiperazinyl]-5-(3-methyl-1H-indazol-5-yl)pyrazine 110 (12 mg, 0.03 mmol).

Preparative Example 3

Alkylation of 2-aminopyrazine

Preparation of 3-[(S)4-Boc-3-benzylpiperazinyl]-5-bromo-2-methylaminopyrazine 111

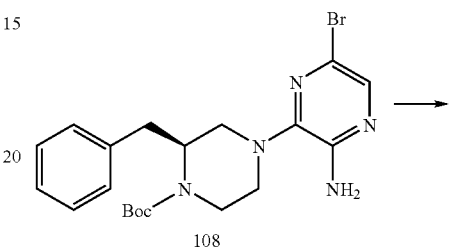

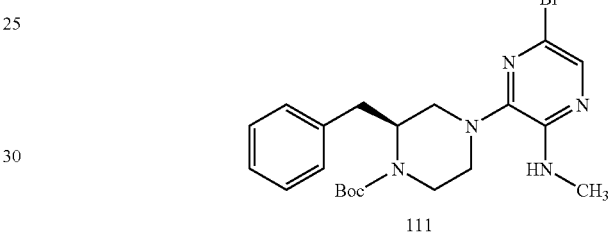

To a solution of 2-amino-5-bromo-3-[(S)4-Boc-3-benzylpiperazinyl]pyrazine 108 (140 mg, 0.313 mmol) in anhydrous dioxane (3 mL) was added a 1 M solution of potassium t-butoxide (0.34 mL, 0.34 mmol). The reaction mixture was stirred at room temperature for 10 minutes and iodomethane (89 mg, 0.627 mmol) was added. The reaction mixture was stirred at room temperature for 2 hours. Ethyl acetate (100 mL) was added. The organic layer was washed with water and brine. The organic layer was dried over sodium sulfate. The organic solvent was evaporated under reduced pressure. The crude product was purified by RP-HPLC to yield the desired 3-[(S)-4-Boc-3-benzylpiperazinyl]-5-bromo-2-methylaminopyrazine 111 (45 mg, 0.97 mmol).

Preparative Example 4

Preparation of 2-benzylamino-3-[(S)-4-Boc-3-benzylpiperazinyl]-5-bromopyrazine 112

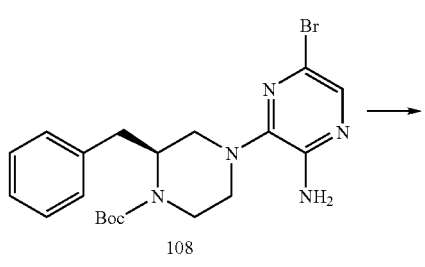

-continued

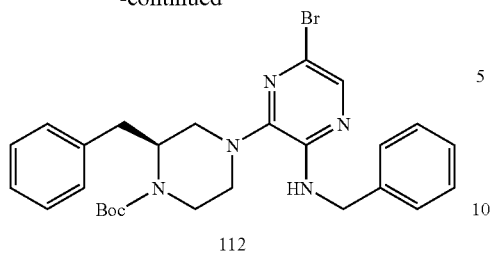

112

To a solution of 2-amino-5-bromo-3-[(S)-4-Boc-3-benzylpiperazinyl]pyrazine 108 (170 mg, 0.379 mmol) in anhydrous dioxane (3 mL) was added a 1 M solution of potassium t-butoxide (0.42 mL, 0.42 mmol). The reaction mixture was stirred at room temperature for 10 minutes and benzyl bromide (130 mg, 0.76 mmol) was added. The reaction mixture was stirred at room temperature for 2 hours. Ethyl acetate (100 mL) was added. The organic layer was washed with water and brine. The organic layer was dried over sodium sulfate. The organic solvent was evaporated under reduced pressure. The crude product was purified by flash column chromatography to yield the desired 2-benzylamino-3-[(S)-4-Boc-3-benzylpiperazinyl]-5-bromopyrazine 112 (165 mg, 0.307 mmol).

Preparative Example 5

Preparation of 3-[(S)-4-Boc-3-benzylpiperazinyl]-5-bromo-2-dimethylaminopyrazine 113

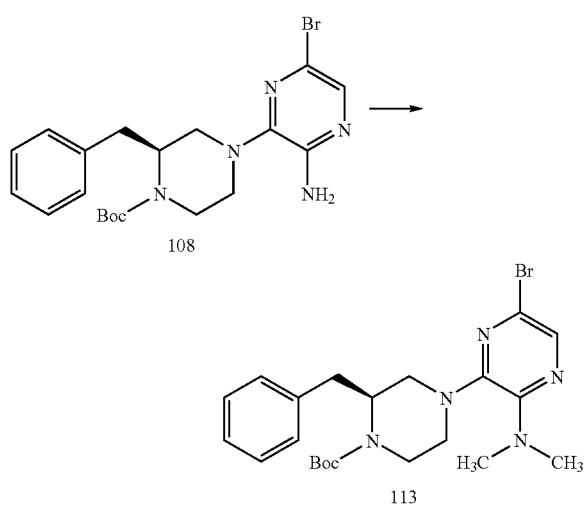

To a solution of 2-amino-5-bromo-3-[(S)-4-Boc-3-benzylpiperazinyl]pyrazine 108 (170 mg, 0.379 mmol) in anhydrous dioxane (4 mL) was added a 1 M solution of potassium t-butoxide (0.95 mL, 0.95 mmol). The reaction mixture was stirred at room temperature for 10 minutes and iodomethane (269 mg, 1.89 mmol) was added. The reaction mixture was heated in a microwave reactor at 180° C. for 30 minutes. Ethyl acetate (100 mL) was added. The organic layer was washed with water and brine. The organic layer was dried over sodium sulfate. The organic solvent was evaporated under reduced pressure. The crude product was purified by RP-HPLC to yield the desired 3-[(S)-4-Boc-3-benzylpiperazinyl]-5-bromo-2-dimethylaminopyrazine 113 (19 mg, 0.04 mmol).

Preparative Example 6

Preparation of 2-[(S)-4-Boc-3-benzylpiperazinyl]-6-chloropyrazine 115

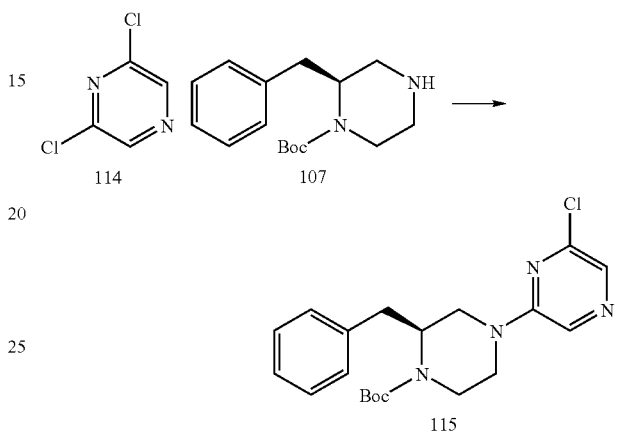

To a solution of 2,6-dichloropyrazine 114 (0.1 g, 0.67 mmol.) and (S)-1-Boc-2-benzylpiperazine 107 (0.37 g, 1.34 mmol) in dioxane (2 mL) and trifluoromethylbenzene (2 mL) was added diisopropylethylamine (0.26 g, 2.0 mmol). The reaction mixture was heated in a microwave reactor at 180° C. for 20 minutes. Ethyl acetate (100 mL) was added. The organic layer was washed with saturated ammonium chloride solution, water and brine. The organic layer was dried over sodium sulfate. The organic solvent was evaporated under reduced pressure. The crude product was purified by flash column chromatography to yield the desired 2-[(S)-4-Boc-3-benzylpiperazinyl]-6-chloropyrazine 115 (0.234 g, 0.6 mmol).

Preparative Example 7

Preparation of 5-bromo-3-methyl-1-(trimethylsilyl)ethoxymethyl-1H-indazole 116

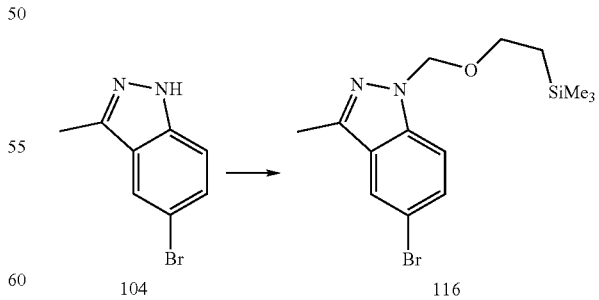

To a solution of 5-bromo-3-methyl-1H-indazole 104 (0.4 g, 1.89 mmol) in anhydrous DMF (4 mL) at 0° C. was added sodium hydride (0.068 g, 2.85 mmol) and 2-(trimethylsilyl)ethoxymethyl chloride (0.377 g, 2.26 mmol). The reaction mixture was stirred at 0° C. fro 1 hour. Ethyl acetate (100 mL)

was added. The organic layer was washed with saturated ammonium chloride solution, water and brine. The organic layer was dried over sodium sulfate. The organic solvent was evaporated under reduced pressure. The crude product was purified by flash column chromatography to yield the desired 5-bromo-3-methyl-1-(trimethylsilyl)ethoxymethyl-1H-indazole 116 (0.369 g, 1.08 mmol).

Preparative Example 8

Preparation of [3-methyl-1-(trimethylsilyl)ethoxymethy-1H-indazol-5-yl]boronic acid pinacol ester 117

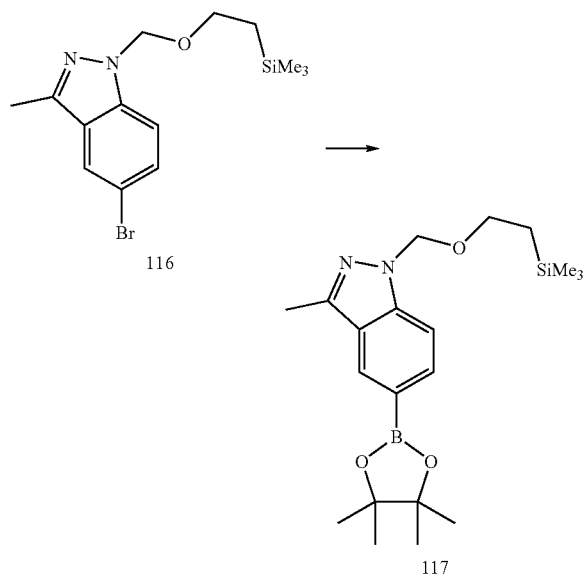

To a solution of 5-bromo-3-methyl-1-(trimethylsilyl) ethoxymethyl-1H-indazole 116 (0.369 g, 1.08 mmol) in DMSO (6 mL) was added potassium acetate (0.318 g, 3.24 mmol), Pd(dppf)Cl$_2$ (0.04 g, 0.055 mmol) and bis(pinacolato)diboron (0.33 g, 1.30 mmol). The reaction mixture was heated at 80° C. for 1 hour. Ethyl acetate (100 mL) was added. The organic layer was washed with water and brine. The organic layer was dried over sodium sulfate. The organic solvent was evaporated under reduced pressure. The crude product was purified by flash column chromatography to yield the desired [3-methyl-1-(trimethylsilyl)ethoxymethy-1H-indazol-5-yl]boronic acid pinacol ester 117 (0.317 g, 0.817 mmol).

Example 2

Step A: Suzuki Coupling Reaction of Halopyrazine

Preparation of 2-[(S)-4-Boc-3-benzylpiperazinyl]-6-[3-methyl-1-(trimethylsilyl)ethoxymethyl-1H-indazol-5-yl]pyrazine 118

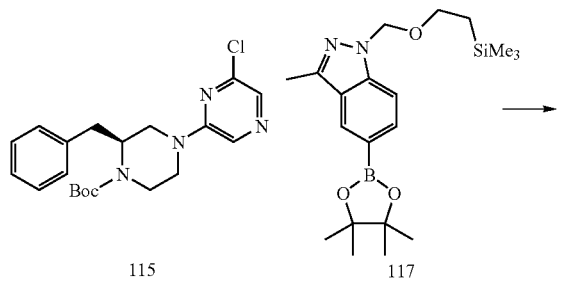

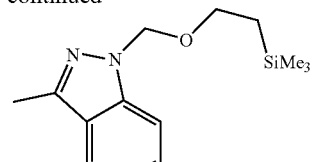

To a solution of 2-[(S)-4-Boc-3-benzylpiperazinyl]-6-chloropyrazine 115 (0.10 g, 0.258 mmol) and [3-methyl-1-(trimethylsilyl)ethoxymethy-1H-indazol-5-yl]boronic acid pinacol ester 117 (0.10 g, 0.258 mmol) in 1,2-dimethoxyethane (5 mL) was added saturated sodium carbonate solution (0.5 mL) and Pd(dppf)Cl$_2$ (0.019 g, 0.026 mmol). The reaction mixture was heated in a microwave reactor at 140° C. for 15 minutes. Ethyl acetate (100 mL) was added. The organic layer was washed with water and brine. The organic layer was dried over sodium sulfate. The organic solvent was evaporated under reduced pressure. The crude product was purified by RP-HPLC to yield the desired 2-[(S)-4-Boc-3-benzylpiperazinyl]-6-[3-methyl-1-(trimethylsilyl)ethoxymethyl-1 H-indazol-5-yl]pyrazine 118 (0.115 g, 0.187 mmol).

Step B: Removal of the (Trimethysilyl)Ethoxymethyl Protecting Group

Preparation of 2-[(S)-3-benzylpiperazinyl]-6-[3-methyl-1H-indazol-5-yl]pyrazine 119

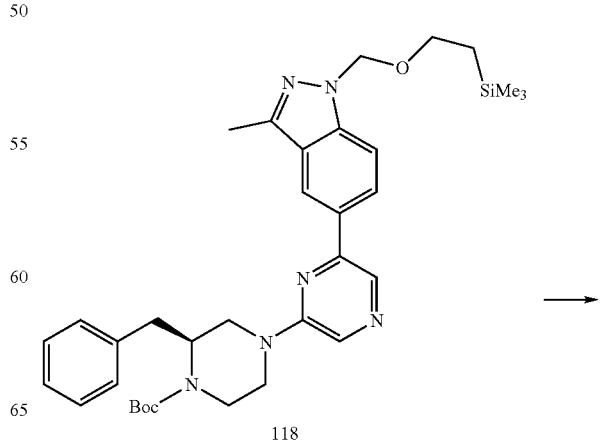

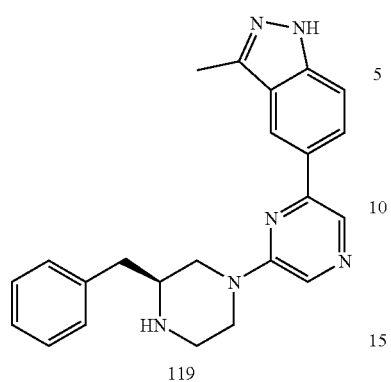

2-[(S)-4-Boc-3-benzylpiperazinyl]-6-[3-methyl-1-(trimethylsilyl)ethoxymethyl-1H-indazol-5-yl]pyrazine 118 (0.115 g, 0.187 mmol) was dissolved in a 90% aqueous trifloroacetic acid solution (10 mL). The reaction mixture was stirred at room temperature for 16 hours. The solvent was evaporated under reduced pressure. The crude product was purified by RP-HPLC to yield the desired 2-[(S)-3-benzylpiperazinyl]-6-[3-methyl-1H-indazol-5-yl]pyrazine 119 (0.072 g, 0.187 mmol).

Examples 3 to 9

Following procedures similar to those in Examples 1 and 2, the compounds in Table 1 were prepared.

TABLE 1-continued
| Example No. | Compound |
|---|---|
| 9 | 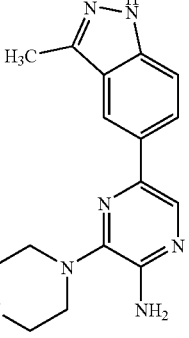 |
| 10 | 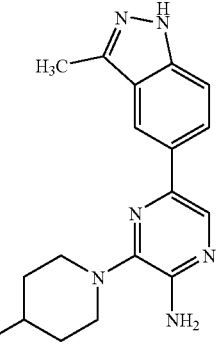 |
| 11 | 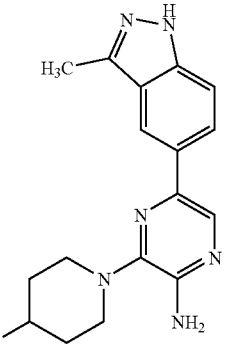 |
| 12 | 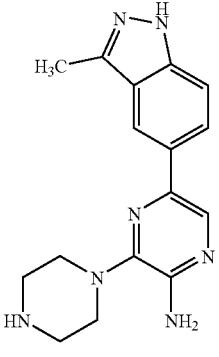 |
| 13 | 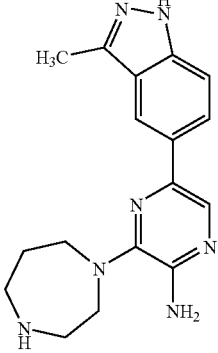 |
| 14 | 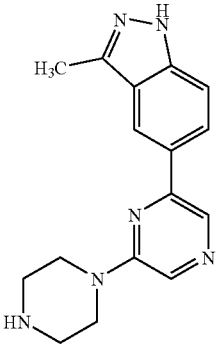 |
| 15 | 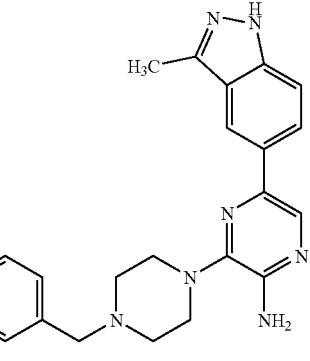 |
| 16 | 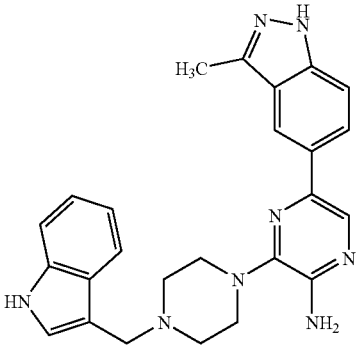 |

TABLE 1-continued
| Example No. | Compound |
|---|---|
| 17 | 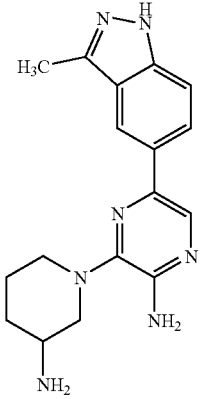 |
| 18 | |
| 19 | |
TABLE 1-continued
| Example No. | Compound |
|---|---|
| 20 | 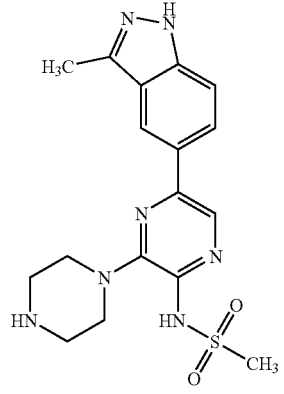 |
| 21 | |
| 22 | |

TABLE 1-continued

| Example No. | Compound |
|---|---|
| 23 | (3-methyl-1H-indazol-5-yl)-pyrazine with piperazine and N-H-C(O)-CH2-phenyl |
| 24 | (3-methyl-1H-indazol-5-yl)-pyrazine with piperazine and HN-CH2CH2-O-CH3 |
| 25 | (3-methyl-1H-indazol-5-yl)-pyrazine with piperazine and HN-CH3 |
| 26 | (3-methyl-1H-indazol-5-yl)-pyrazine with piperazine and HN-CH2CH3 |
| 27 | (3-methyl-1H-indazol-5-yl)-pyrazine with piperazine and N(CH3)(CH2-phenyl) |
| 28 | (3-methyl-1H-indazol-5-yl)-pyrazine with piperazine and N(CH2-phenyl)2 |
| 29 | (3-methyl-1H-indazol-5-yl)-pyrazine with piperazine and HN-CH2-(4-chlorophenyl) |
| 30 | (3-methyl-1H-indazol-5-yl)-pyrazine with piperazine and HN-CH2-(3-chlorophenyl) |

TABLE 1-continued
| Example No. | Compound |
|---|---|
| 31 | 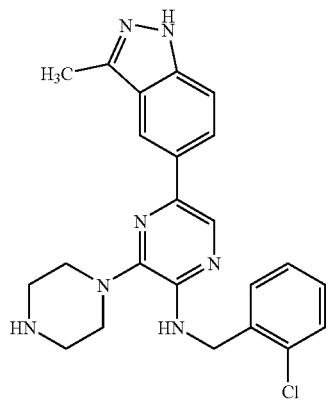 |
| 32 | 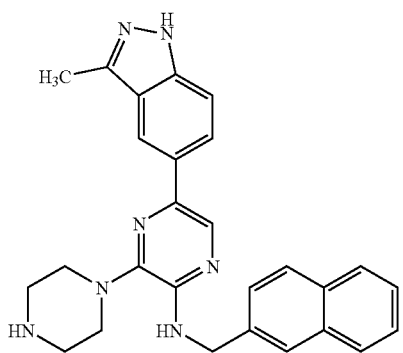 |
| 33 | 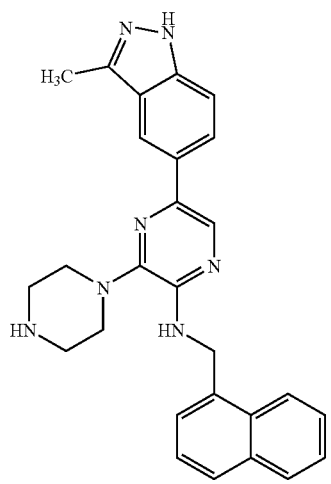 |
TABLE 1-continued
| Example No. | Compound |
|---|---|
| 34 | 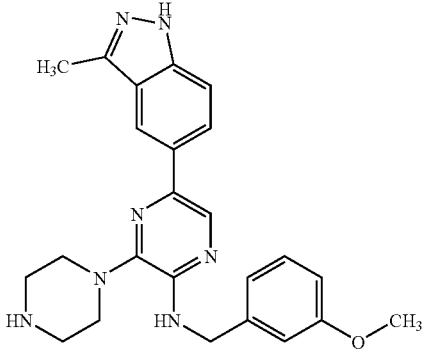 |
| 35 | 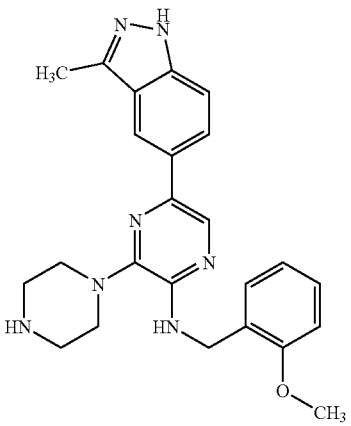 |
| 36 | 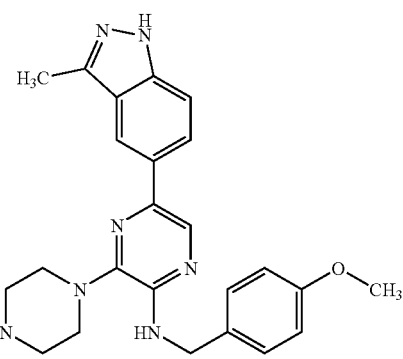 |
| 37 | 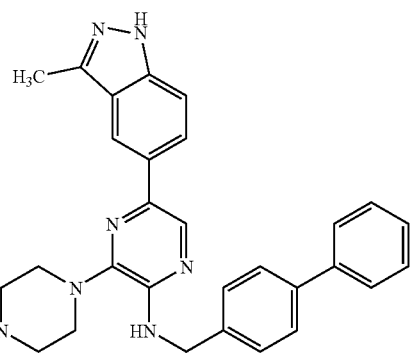 |

TABLE 1-continued

| Example No. | Compound |
|---|---|
| 38 | 3-methyl-1H-indazol-5-yl pyrazine with piperazine and N-(2-methylbenzyl)amine substituents |
| 39 | 3-methyl-1H-indazol-5-yl pyrazine with piperazine and N-(4-methylbenzyl)amine substituents |
| 40 | 3-methyl-1H-indazol-5-yl pyrazine with piperazine and N-(3-methylbenzyl)amine substituents |
| 41 | 3-methyl-1H-indazol-5-yl pyrazine with piperazine and N-(2-fluorobenzyl)amine substituents |
| 42 | 3-methyl-1H-indazol-5-yl pyrazine with piperazine and N-(3-fluorobenzyl)amine substituents |
| 43 | 3-methyl-1H-indazol-5-yl pyrazine with piperazine and N-(4-fluorobenzyl)amine substituents |
| 44 | 3-methyl-1H-indazol-5-yl pyrazine with piperazine and N-(pyridin-4-ylmethyl)amine substituents |
| 45 | 3-methyl-1H-indazol-5-yl pyrazine with piperazine and N-(quinolin-2-ylmethyl)amine substituents |

TABLE 1-continued

| Example No. | Compound |
|---|---|
| 46 | (structure) |
| 47 | (structure) |
| 48 | (structure) |
| 49 | (structure) |
| 50 | (structure) |

Akt1 Kinase Assay

The assay described below measures the phosphorylation of a biotinylated peptide by active recombinant Akt1 and other kinase isoforms. The biotinylated peptide contains a consensus sequence derived from Akt substrate Gsk3 (Glycogen synthase kinase 3). The $^{33}$P-labeled peptide substrate was captured by streptavidin-coated Flash plates.

Enzyme and Substrate

Active recombinant Akt1 was expressed in Sf9 insect cells and purified as described by Kumar et al., *Biochim. Biophys. Acta*. Jun. 15, 2001, 1526(3), 257-268. Biotinylated peptide of the sequence Bio-ahx-RPRAASF was purchased from Syn Pep (Dublin, Calif., USA).

Cloning and Expression of Human Akt1 Sf9 Cells

Human Akt1 cDNA was amplified from a marathon-ready human lung cDNA library (Clonetech) using nested oligo primers as described below. The first round of amplification was carried out using the following primers; Akt1F1 (ATCA-GAGGCTGTGGCCAGGCCAGCTGG) (SEQ ID NO: 1 and Akt1R1 (TCCATC CCTCCAAGCGACGTGGCTATTG) (SEQ ID NO: 2) and for the second round amplification, the primers of the following sequence were used; Akt1F2 (GGATCCTCGG GCACCATGAGCGACGTGGCTATTG)

(SEQ ID NO: 3) and AKT1R2 (GGTACCATCGTC CAGC-CAGTCCACCGCCGCCTCA) (SEQ ID NO: 4). The PCR product was subcloned into pCRScript plasmid as a BamHI/KpnI fragment and the sequence of the cDNA was confirmed by DNA sequencing. This plasmid was used as a template for reamplification of Akt1 using appropriate primers for subcloning into pBlueBaHis2B into BamH1/EcoRI sites to generate an in frame fusion to $(His)_6$ tag and an anti-Xpress antibody epitope tag at the N-terminus. This construct was sequenced to verify the junction sequences and used for generating a recombinant baculovirus. Growth of the recombinant virus, amplification and determination of viral titer were carried out according to the instructions from the manufacturer (InVitrogen, Calif.).

Purification of Akt1 from Sf9 Cells

Viral stocks were used to infect large scale Sf9 cells at a multiplicity of infection (MOI) of 2.5. Cells were maintained at 27° C. for 60 h and okadaic acid was added to the cultures to a concentration of 50 nM. Cells were harvested 4 h hours later by centrifugation at 1200 rpm for 30 min followed by freezing at −80° C. until further use. All purification steps were carried out at 4° C. Whole cell pellets were suspended in buffer A (20 mM sodium phosphate buffer pH 7.8, 500 mM NaCl, 1 mM sodium vanadate, 5 mM sodium fluoride, 40 mM β-glycerophosphate, 10 mM imidazole and protease inhibitor cocktail) and lysed using a microfluidizer. The cell extract was centrifuged at 16,000×g for 10 min to remove the debris and directly loaded onto Ni-NTA Superflow resin using a FPLC pump operated at 1 ml/min. The column was washed once with buffer A, once with wash buffer B (20 mM sodium phosphate pH 6.0, 1 mM sodium vanadate, 5 mM sodium fluoride and protease cocktail) and once with wash buffer B containing 0.05% Tween-20 followed by washing with buffer A until $OD_{260}$ returned to basal level. Proteins were eluted with buffer A containing 200 mM imidazole. Fractions were analyzed by electrophoresis on 10% denaturing polyacrylamide gels and fractions containing 85% pure protein band at 60 KDa were pooled and dialyzed against buffer C (20 mM Tris-HCl pH 7.5, 0.5 mM EDTA, 2 mM DTT, 145 mM NaCl, 0.1 mM sodium vanadate, 5 mM sodium fluoride, 10 mM β-glycerophosphate and 20% glycerol). Purified protein was stored as aliquots at −80° C. Protein concentrations were determined using BCA protein assay reagent A (Catalog #23228). To examine the identity of the proteins, 2 μg of purified protein was electrophoresed on SDS-polyacrylamide gels and stained with coomassie blue dye or transferred to nitrocellulose membrane and probed with anti-Akt and anti-phospho-specific Akt antibodies using enhanced chemiluminescence (ECL) reagent according to the protocol described by the manufacturer (Amersham).

Kinase Assays

The kinase assay was performed in 96 well plates at room temperature. Assay solutions and plates were preincubated at room temperature for 5 min. To each well, we added 10 μL of peptide solution (5 μM) in kinase buffer (50 mM Tris-HCl pH 7.5, 10 mM $MgCl_2$, 1 mM Tris [2-Carboxyethyl]phosphine hydrochloride (TCEP) and 0.1 mM sodium ortho vanadate, 0.02% bovine serum albumin). The kinase buffer (10 μL) was dispensed to each well of a 96 well plate. Purified Akt1 was diluted to the proper concentration in kinase buffer and 10 μL of the diluted enzyme was dispensed to each well. Compounds diluted appropriately in reaction buffer containing 10% $Me_2SO$ were also dispensed in 10 μL aliquots. The reactions were started by adding 10 μL of ATP solution containing 5 μM ATP and 0.25 μCi of [γ-$^{33}$P]ATP in kinase buffer. The final concentrations of the components are, 1 μM biotinylated peptide, 200 ng of Akt1 enzyme, 0.25 μCi of [γ-$^{33}$P]-ATP, 2 μM cold ATP, 50 mM Tris-HCl pH 7.5, 10 mM $MgCl_2$, 1 mM TCEP, 0.02% bovine serum albumin, 2% $Me_2SO$ and 0.1 mM sodium vanadate. The plates were incubated at room temperature for 2 hr and at the end of the incubation, reactions were stopped by adding 200 μL of stop solution containing 1 mM ATP, 5 mM EDTA in phosphate buffered saline followed by transferring of 200 μL of the mixture to streptavidin-coated flash plates. Biotinylated peptides were allowed to bind to the flash plates for one hour at room temperature followed by two rinses with wash buffer. Plates were counted using a Top Count instrument.

The compounds of Examples 1 to 50 had an AKT1 $IC_{50}$ within the range of 0.00098 to 8.1 μM. The compounds of Examples 1, 2, 5, 8, 12, 18, 27, 29, 30, 31, 34, 35, 38, 41, 42, 43, and 50 had an AKT1 $IC_{50}$ within the range of 0.00098 to 0.24 μM. The compounds of Examples 2, 18 and 42 had an AKT1 $IC_{50}$ within the range of 0.00098 to 0.046 μM. The compound of Example 2 had an AKT1 $IC_{50}$ of 0.00098 μM.

AKT1 $IC_{50}$ data is given in Table 2 for compounds of this invention.

TABLE 2

| Structure | AKT1 IC50 (nM) |
|---|---|
| (3-methyl-1H-indazol-5-yl pyrazine piperazine benzyl structure) | 1 |
| (3-methyl-1H-indazol-5-yl pyrazine piperazine benzylamino structure) | 46 |

TABLE 2-continued

| Structure | AKT1 IC50 (nM) |
|---|---|
| (3-methyl-indazol-5-yl)-pyrazine with H2N-CH2CH2-NH and N-benzyl substituents | 79 |
| (3-methyl-indazol-5-yl)-pyrazine with piperazine and N-(3-fluorobenzyl) substituents | 44 |
| (3-methyl-indazol-5-yl)-pyrazine with (R)-2-benzylpiperazine and N-benzyl substituents | 76 |
| (3-methyl-indazol-5-yl)-pyrazine with piperazine and N-(2-chlorobenzyl) substituents | 129 |

TABLE 2-continued

| Structure | AKT1 IC50 (nM) |
|---|---|
| (3-methyl-indazol-5-yl)-pyrazine with (S)-2-benzylpiperazine and NH2 substituents | 55 |
| (3-methyl-indazol-5-yl)-pyrazine with H2N-CH2CH2-NH and NH2 substituents | 74 |
| (3-methyl-indazol-5-yl)-pyrazine with piperazine and N-(2-methylbenzyl) substituents | 140 |
| (3-methyl-indazol-5-yl)-pyrazine with piperazine and N-(3-methoxybenzyl) substituents | 148 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

---

What is claimed is:

1. A compound of the formula:

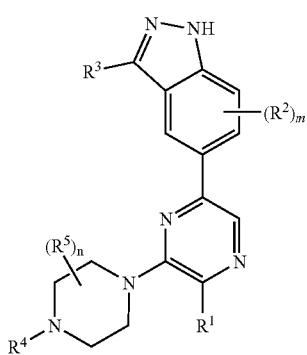

(1.1)

or the pharmaceutically acceptable salts thereof; wherein:

$R^1$ is —NH(CH$_2$C$_6$H$_5$);

m is 0;

$R^3$ is selected from the group consisting of: halo and alkyl;

$R^4$ is H;

n is 1;

$R^5$ is selected from the group consisting of: (a) aralkyl-, (b) heteroarylalkyl, (c) aryl, (d) —C(O)OR$^{26}$, (e) —R$^{28}$—O—R$^{30}$, and (f) alkyl;

$R^{26}$ is selected from the group consisting of:

(1) H,
(2) aryl,
(3) substituted aryl,
(4) heteroaryl,
(5) substituted heteroaryl,
(6) cyclyl,
(7) substituted cyclyl,
(8) arylalkylene-,
(9) substituted arylalkylene-,

(10) heteroarylalkylene-,
(11) substituted heteroarylalkylene-,
(12) heterocyclyl,
(13) substituted heterocyclyl,
(14) heterocyclyl-alkylene-,
(15) substituted heterocyclyl-alkylene-,
(16) alkyl, and
(17) substituted alkyl, and
wherein:
(A) said substituted $R^{26}$ substituents (3), (5), (7), (9), (11), (13), and (15) are substituted with 1 to 3 substituents independently selected from the group consisting of: (a) alkyl, (b) haloalkyl, (c) halo, (d) alkoxy, and (e) CN, and
(B) said substituted alkyl $R^{26}$ substituent (17) is substituted with 1 to 3 substituents independently selected from the group consisting of: (a) haloalkyl, (b) halo, (c) alkoxy, and (d) CN;
$R^{28}$ is selected from the group consisting of:
(1) alkylene; and
(2) substituted alkylene; and wherein said substituted alkylene is substituted with 1 to 3 substituents independently selected from the group consisting of: (a) alkyl, (b) haloalkyl, (c) halo, (d) alkoxy, and (e) CN; or
$R^{28}$ is absent; and
$R^{30}$ selected from the group consisting of:
(1) H,
(2) aryl,
(3) substituted aryl,
(4) heteroaryl,
(5) substituted heteroaryl,
(6) cyclyl,
(7) substituted cyclyl,
(8) arylalkylene-,
(9) substituted arylalkylene-,
(10) heteroarylalkylene-,
(11) substituted heteroarylalkylene-,
(12) heterocyclyl,
(13) substituted heterocyclyl,
(14) heterocyclyl-alkylene-,
(15) substituted heterocyclyl-alkylene-,
(16) alkyl, and
(17) substituted alkyl, and
wherein:
(A) said substituted $R^{30}$ substituents (3), (5), (7), (9), (11), (13), and (15) are substituted with 1 to 3 substituents independently selected from the group consisting of: (a) alkyl, (b) haloalkyl, (c) halo, (d) alkoxy, and (e) CN, and
(B) said substituted alkyl $R^{30}$ substituent (17) is substituted with 1 to 3 substituents independently selected from the group consisting of: (a) haloalkyl, (b) halo, (c) alkoxy, and (d) ON.

2. A compound of the formula:

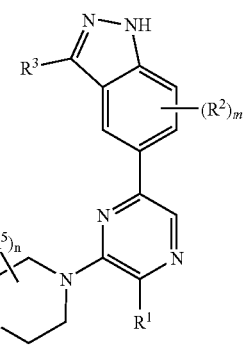

(1.1)

or the pharmaceutically acceptable salts thereof; wherein:
$R^1$ is $-NR^{20}R^{22}$ wherein $R^{20}$ and $R^{22}$ are independently selected from the group consisting of: H, alkyl, benzyl and substituted benzyl; and provided that at least one of $R^{20}$ or $R^{22}$ is benzyl or substituted benzyl; and wherein said substituted benzyl is substituted with 1 to 3 substituents independently selected from the group consisting of: (a) alkyl, (b) haloalkyl, (c) halo, (d) alkoxy, (e) CN, and (f) aryl;
m is 0;
$R^3$ is selected from the group consisting of: halo and alkyl;
$R^4$ is H; and
n is 0.

3. The compound of claim 1 wherein $R^5$ is selected from the group consisting of: benzyl, phenyl, $-C(O)OCH_3$, $-CH_2-O-CH_2$-phenyl, i-propyl, i-butyl and $-CH_2$indolyl.

4. The compound of claim 1 wherein $R^5$ is benzyl.

5. The compound of claim 2 wherein said substituted benzyl is substituted with 1 to 3 substituents independently selected from the group consisting of: $C_1$ to $C_6$ alkyl, $-CF_3$, F, Cl, Br, $-OCH_3$, CN, phenyl.

6. The compound of claim 2 wherein one of $R^{20}$ or $R^{22}$ is benzyl.

7. The compound of claim 2 wherein one of $R^{20}$ or $R^{22}$ is substituted benzyl.

8. The compound of claim 7 wherein said substituted benzyl is substituted with 1 to 3 substituents independently selected from the group consisting of: $C_1$ to $C_6$ alkyl, $-CF_3$, F, Cl, Br, $-OCH_3$, CN, phenyl.

9. A compound selected from the group consisting of:

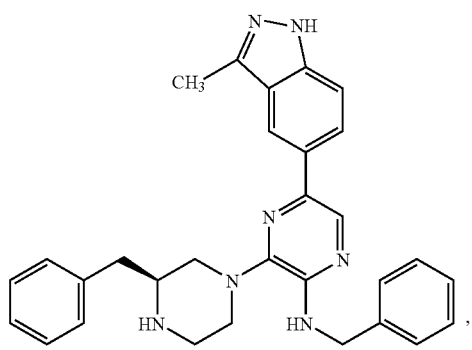

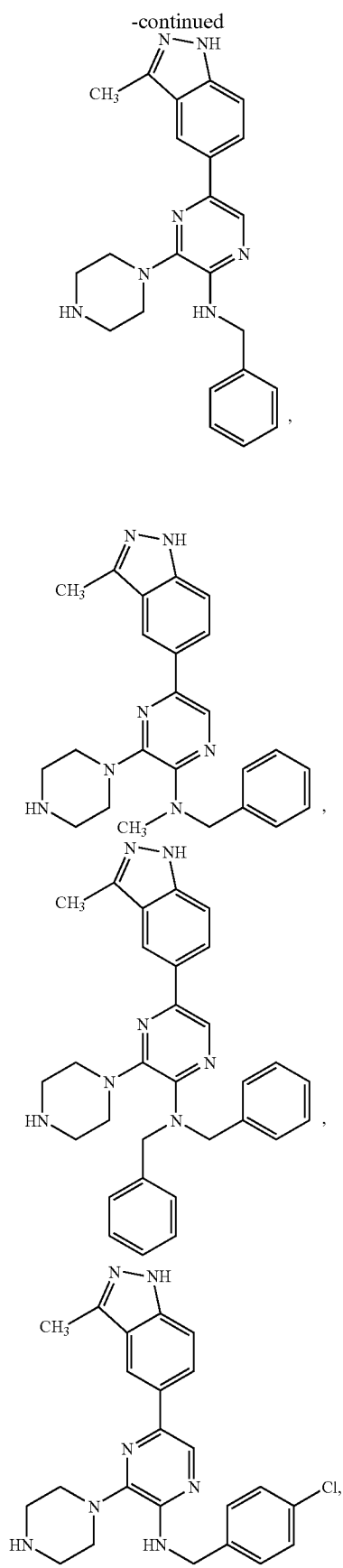
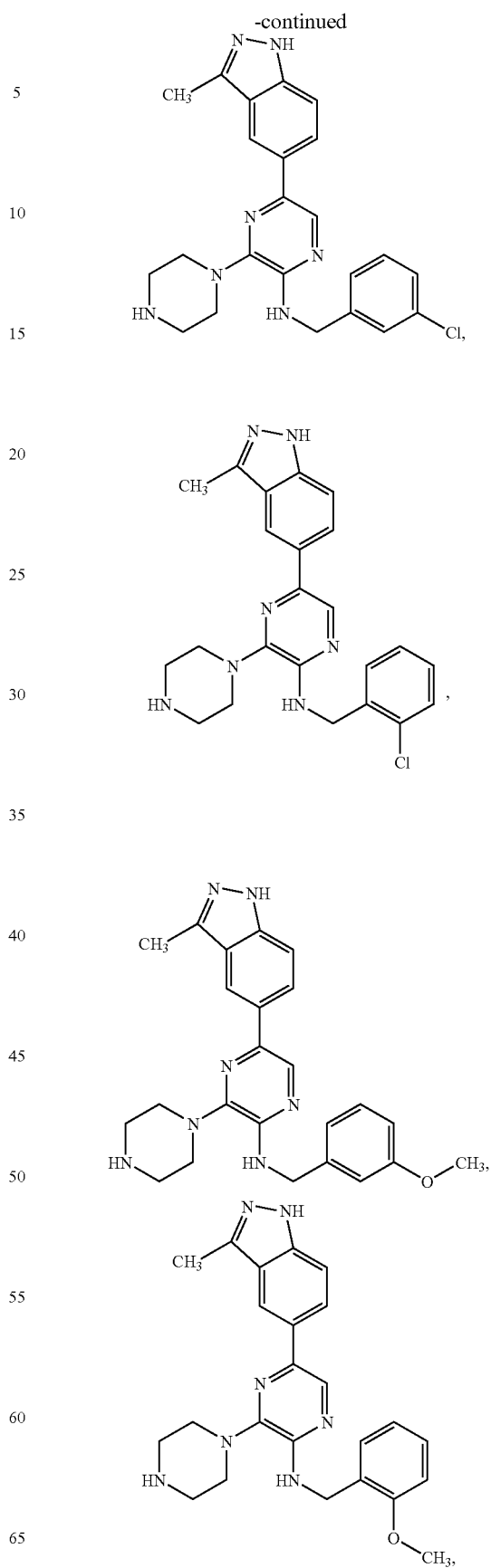

-continued
97
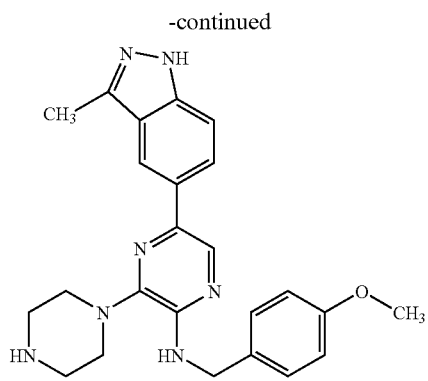
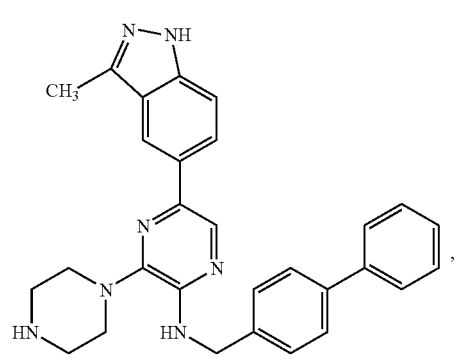
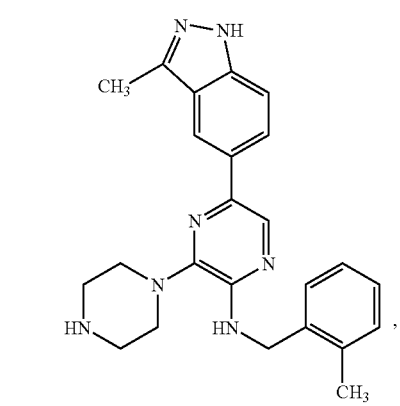
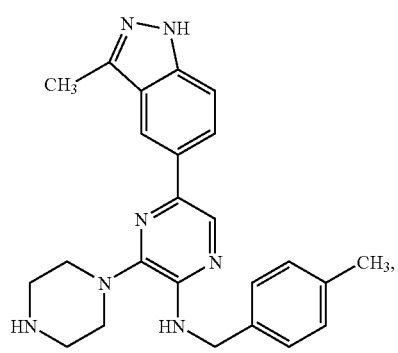
98
-continued
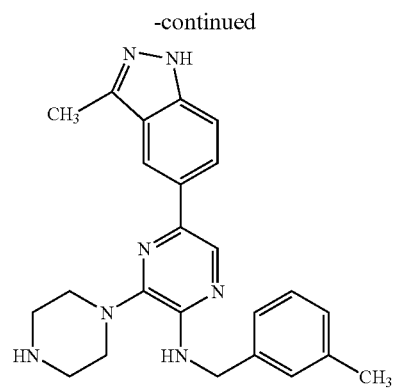
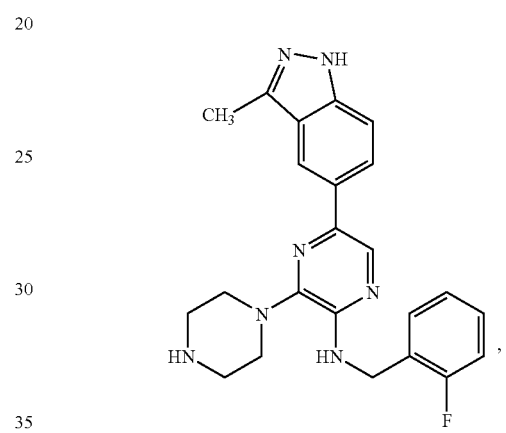
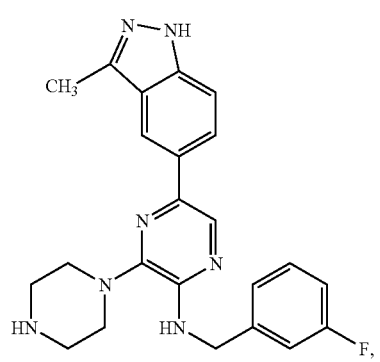
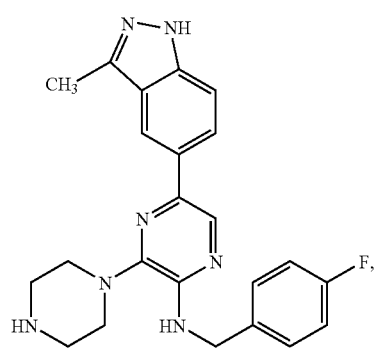

-continued

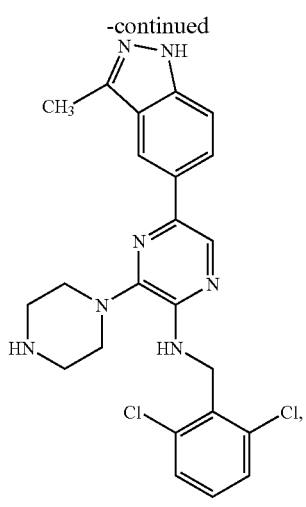

10. A compound of the formula:

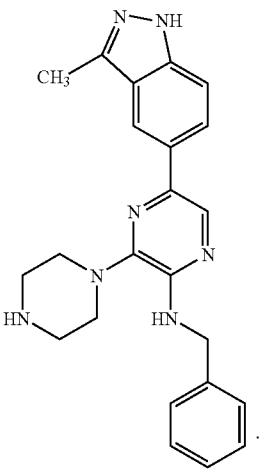

11. A compound of the formula:

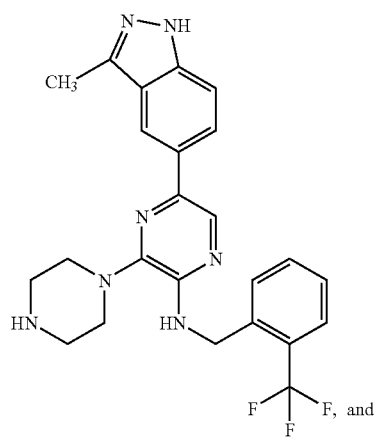

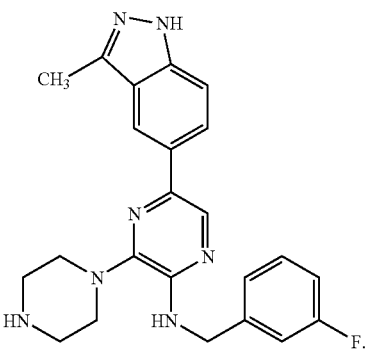

12. A pharmaceutical composition comprising at least one compound of claim 1 and a pharmaceutically acceptable carrier.

13. A pharmaceutical composition comprising at least one compound of claim 2 and a pharmaceutically acceptable carrier.

14. A pharmaceutical composition comprising at least one compound of claim 9 and a pharmaceutically acceptable carrier.

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Akt1F1 primer

<400> SEQUENCE: 1
atcagaggct gtggccaggc cagctgg                                    27

<210> SEQ ID NO 2
<211> LENGTH: 28
<212> TYPE: DNA
<213> ORGANISM: Artificial Sequence
<220> FEATURE:
<223> OTHER INFORMATION: Akt1R1 primer

<400> SEQUENCE: 2
tccatccctc caagcgacgt ggctattg                                   28

<210> SEQ ID NO 3
<211> LENGTH: 34
<212> TYPE: DNA
<213> ORGANISM: Artificial Sequence
<220> FEATURE:
<223> OTHER INFORMATION: Akt1F2 primer

<400> SEQUENCE: 3
ggatcctcgg gcaccatgag cgacgtggct attg                            34

<210> SEQ ID NO 4
<211> LENGTH: 34
<212> TYPE: DNA
<213> ORGANISM: Artificial Sequence
<220> FEATURE:
<223> OTHER INFORMATION: AKT1R2 primer

<400> SEQUENCE: 4
ggtaccatcg tccagccagt ccaccgccgc ctca                            34